United States Patent
Yan et al.

(10) Patent No.: US 6,773,904 B2
(45) Date of Patent: Aug. 10, 2004

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Chunhua Yan, Boyds, MD (US); Karen A. Ketchum, Germantown, MD (US); Ellen M. Beasley, Darnestown, MD (US)

(73) Assignee: Applera Corporation, Norwalk, CT (US)

(*) Notice: Subject to any disclaimer, the term of this patent is extended or adjusted under 35 U.S.C. 154(b) by 164 days.

(21) Appl. No.: 10/118,328

(22) Filed: Apr. 9, 2002

(65) Prior Publication Data

US 2002/0169289 A1 Nov. 14, 2002

Related U.S. Application Data

(60) Provisional application No. 60/282,460, filed on Apr. 10, 2001.

(51) Int. Cl.[7] ............... C07H 21/04; C12P 21/06; C12N 9/12; C12N 1/20; C12N 15/00

(52) U.S. Cl. ............... 435/194; 435/183; 435/194; 435/195; 435/196; 435/69.1; 435/252.3; 435/320.1; 536/23.2; 536/23.5

(58) Field of Search ............... 435/4, 69.1, 183.193, 435/194, 195, 196, 252.3, 320.1, 325; 536/23.2, 23.5

(56) References Cited

PUBLICATIONS

Results of Blast search of SEQ ID NO:2 against Derwent (FastAlert and GeneSeqP) and NCBI (pataa) protein patent databases on Sep. 12, 2003.

*Primary Examiner*—Manjunath Rao
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

9 Claims, 28 Drawing Sheets

```
   1 ATGGAGCGCA CAGCAGGCAA AGAGCTGGCC CTGGCACCGC TGCAGGACTG
  51 GGGTGAAGAG ACCGAGGACG GCGCGGTGTA CAGTGTCTCC CTGCGGCGGC
 101 AGCGCAGTCA GCGCAGGAGC CCGGCGGAGG GCCCCGGGGG CAGCCAGGCT
 151 CCCAGCCCCA TTGCCAATAC CTTCCTCCAC TATCGAACCA GCAAGGTGAG
 201 GGTGCTGAGG GCAGCGCGCC TGGAGCGGCT GGTGGGAGAG TTGGTGTTTG
 251 GAGACCGTGA GCAGGACCCC AGCTTCATGC CCGCCTTCCT GGCCACCTAC
 301 CGGACCTTTG TACCCACTGC CTGCCTGCTG GGCTTTCTGC TGCCACCAAT
 351 GCCACCGCCC CCACCTCCCG GGGTAGAGAT CAAGAAGACA GCGGTACAAG
 401 ATCTGAGCTT CAACAAGAAC CTGAGGGCTG TGGTGTCAGT GCTGGGCTCC
 451 TGGCTGCAGG ACCACCCTCA GGATTTCCGA GACCACCCTG TCCATTCGGA
 501 CCTGGGCAGT GTCCGAACCT TTCTGGGCTG GCGGCCCCA GGGAGTGCTG
 551 AGGCTCAAAA AGCAGAAGAAG CTTCTGGAAG ATTTTTTGGA GGAGGCTGAG
 601 CGAGAGCAGG AAGAGGAGCC GCCTCAGGTG TGGACAGGAC CTCCCAGAGT
 651 TGCCCAAACT TCTGACCCAG ACTCTTCAGA GGCCTGCGCG GAGGAAGAGG
 701 AAGGGCTCAT GCCTCAAGGT CCCCAGCTCC TGGACTTCAG CGTGGACGAG
 751 GTGGCCGAGC AGCTGACCCT CATAGACTTG GAGCTCTTCT CCAAGGTGAG
 801 GCTCTACGAG TGCTTGGGCT CCGTGTGGTC GCAGAGGGAC CGGCCGGGGG
 851 CTGCAGGCGC CTCCCCCACT GTGCGCGCCA CCGTGGCCCA GTTCAACACC
 901 GTGACCGGCT GTGTGCTGGG TTCCGTGCTC GGAGCACCGG GCTTGGCCGC
 951 CCCGCAGAGG GCGCAGCGGC TGGAGAAGTG GATCCGCATC GCCCAGCGCT
1001 GCCGAGAACT GCGGAACTTC TCCTCCTTGC GCGCCATCCT GTCCGCCCTG
1051 CAATCTAACC CCATCTACCG GCTCAAGCGC AGCTGGGGGG CAGTGAGCCG
1101 GAACCGCTA TCTACTTTCA GGAAACTTTC GCAGATTTTC TCCGATGAGA
1151 ACAACCACCT CAGCAGCAGA GAGATTCTTT TCCAGGAGGA GGCCACTGAG
1201 GGATCCCAAG AAGAGGACAA CACCCCAGGC AGCCTGCCCT CAAAACCACC
1251 CCCAGGCCCT GTCCCCTACC TTGGCACCTT CCTTACGGAC CTGGTTATGC
1301 TGGACACAGC CCTGCCGGAT ATGTTGGAGG GGGATCTCAT TAACTTTGAG
1351 AAGAGGAGGA AGGAGTGGGA GATCCTGGCC CGCATCCAGC AGCTGCAGAG
1401 GCGCTGTCAG AGCTACACCC TGAGCCCCCA CCCGCCCATC CTGGCTGCCC
1451 TGCATGCCCA GAACCAGCTC ACCGAGGAGC AGAGCTACCG GCTCTCCCGG
1501 GTCATTGAGC CACCAGCTGC CTCCTGCCCC AGCTCCCCAC GCATCCGACG
1551 GCGGATCAGC CTCACCAAGC GTCTCAGTGC GAAGCTTGCC CGAGAGAAAA
1601 GCTCATCACC TAGTGGGAGT CCCGGGGACC CCTCATCCCC CACCTCCAGT
1651 GTGTCCCCAG GGTCACCCCC CTCAAGTCCT AGAAGCAGAG ATGCTCCTGC
1701 TGGCAGTCCC CCGGCCTCTC CAGGGCCCCA GGGCCCCAGC ACCAAGCTGC
1751 CCCTGAGCCT GGACCTGCCC AGCCCCGGC CCTTCGCTTT GCCTCTGGGC
1801 AGCCCTCGAA TCCCCCTCCC GGCGCAGCAG AGCTCGGAGG CCCGTGTCAT
1851 CCGCGTCAGC ATCGACAATG ACCACGGGAA CCTGTATCGA AGCATCTTGC
1901 TGACCAGTCA GGACAAAGCC CCCAGCGTGG TCCGGCGAGC CTTGCAGAAG
1951 CACAATGTGC CCCAGCCCTG GCCTGTGAC TATCAGCTCT TTCAAGTCCT
2001 TCCTGGGGAC CGGGTGCTCC TGATTCCTGA CAATGCCAAC GTCTTCTATG
2051 CCATGAGTCC AGTCGCCCCC AGAGACTTCA TGCTGCGGCG GAAAGAGGGG
2101 ACCCGGAACA CTCTGTCTGT CTCCCCAAGC TGA   (SEQ ID NO:1)
```

FEATURES:
Start Codon: 1
Stop Codon: 2131

FIGURE 1A

Homologous proteins:
Top 10 BLAST Hits

```
                                                                Score    E
CRA|160000003781983 /altid=gi|8650435  /def=gb|AAF78208.1|AF2376...  1119  0.0
CRA|103000001517213 /altid=gi|7682471  /def=gb|AAF67280.1|AF1867...   448  e-125
CRA|18000005222968  /altid=gi|4589562  /def=dbj|BAA76803.1|  (AB02...  448  e-125
CRA|38000046964621  /altid=gi|10185686 /def=gb|AAG14400.1|AF1867...   448  e-125
CRA|18000004932640  /altid=gi|8394180  /def=ref|NP_058542.1| ral ...  442  e-123
CRA|18000005115144  /altid=gi|4758532  /def=ref|NP_004752.1| RAB2...  387  e-106
CRA|120000015982361 /altid=gi|9931302  /def=gb|AAG02122.1|AF2957...   385  e-105
CRA|18000004933686  /altid=gi|6677735  /def=ref|NP_033084.1| ral ...  372  e-102
CRA|18000005176024  /altid=gi|3811378  /def=gb|AAC69894.1|  (AF100... 369  e-101
CRA|18000005033177  /altid=gi|6677737  /def=ref|NP_033085.1| ral ...  368  e-100
```

BLAST dbEST hits:

```
                                             Score    E
gi|12067555 /dataset=dbest /taxon=96...       880   0.0
gi|11311915 /dataset=dbest /taxon=96...       767   0.0
gi|12067611 /dataset=dbest /taxon=96...       700   0.0
gi|843816   /dataset=dbest /taxon=9606 /...   597   e-168
gi|3331474  /dataset=dbest /taxon=9606 ...    591   e-166
gi|6660347  /dataset=dbest /taxon=9606 ...    460   e-127
gi|2322877  /dataset=dbest /taxon=9606 ...    424   e-116
gi|2348656  /dataset=dbest /taxon=9606 ...    422   e-115
gi|4189370  /dataset=dbest /taxon=9606 ...    353   1e-94
```

EXPRESSION INFORMATION FOR MODULATORY USE:
library source:
gi|12067555 bocio-tumor
gi|11311915 Head-neck
gi|12067611 bocio-tumor
gi|843816   Breast
gi|3331474  Parathyroid tumor
gi|6660347  Uterus papillary carcinoma
gi|2322877  Colon tumor
gi|2348656  Colon tumor
gi|4189370  Pooled human melanocyte, fetal heart, and pregnant uterus

FIGURE 1B

```
  1 MERTAGKELA  LAPLQDWGEE  TEDGAVYSVS  LRRQRSQRRS  PAEGPGGSQA
 51 PSPIANTFLH  YRTSKVRVLR  AARLERLVGE  LVFGDREQDP  SFMPAFLATY
101 RTFVPTACLL  GFLLPPMPPP  PPPGVEIKKT  AVQDLSFNKN  LRAVVSVLGS
151 WLQDHPQDFR  DHPVHSDLGS  VRTFLGWAAP  GSAEAQKAEK  LLEDFLEEAE
201 REQEEEPPQV  WTGPPRVAQT  SDPDSSEACA  EEEEGLMPQG  PQLLDFSVDE
251 VAEQLTLIDL  ELFSKVRLYE  CLGSVWSQRD  RPGAAGASPT  VRATVAQFNT
301 VTGCVLGSVL  GAPGLAAPQR  AQRLEKWIRI  AQRCRELRNF  SSLRAILSAL
351 QSNPIYRLKR  SWGAVSREPL  STFRKLSQIF  SDENNHLSSR  EILFQEEATE
401 GSQEEDNTPG  SLPSKPPPGP  VPYLGTFLTD  LVMLDTALPD  MLEGDLINFE
451 KRRKEWEILA  RIQQLQRRCQ  SYTLSPHPPI  LAALHAQNQL  TEEQSYRLSR
501 VIEPPAASCP  SSPRIRRRIS  LTKRLSAKLA  REKSSSPSGS  PGDPSSPTSS
551 VSPGSPPSSP  RSRDAPAGSP  PASPGPQGPS  TKLPLSLDLP  SPRPFALPLG
601 SPRIPLPAQQ  SSEARVIRVS  IDNDHGNLYR  SILLTSQDKA  PSVVRRALQK
651 HNVPQPWACD  YQLFQVLPGD  RVLLIPDNAN  VFYAMSPVAP  RDFMLRRKEG
701 TRNTLSVSPS   (SEQ ID NO:2)
```

FEATURES:
Functional domains and key regions:
[1] PDOC00001 PS00001 ASN_GLYCOSYLATION
N-glycosylation site 339-342 NFSS

[2] PDOC00004 PS00004 CAMP_PHOSPHO_SITE
cAMP- and cGMP-dependent protein kinase phosphorylation site Number of matches: 3
    1    374-377 RKLS
    2    517-520 RRIS
    3    523-526 KRLS

[3] PDOC00005 PS00005 PKC_PHOSPHO_SITE
Protein kinase C phosphorylation site

Number of matches: 18
    1    30-32 SLR
    2    342-344 SLR
    3    36-38 SQR
    4    277-279 SQR
    5    63-65 TSK
    6    99-101 TYR
    7    170-172 SVR
    8    36-38 SQR
    9    277-279 SQR
    10    290-292 TVR
    11    30-32 SLR
    12    342-344 SLR
    13    372-374 TFR
    14    388-390 SSR
    15    495-497 SYR
    16    512-514 SPR
    17    559-561 SPR
    18    591-593 SPR

FIGURE 2A

[4] PDOC00006 PS00006 CK2_PHOSPHO_SITE
Casein kinase II phosphorylation site

Number of matches: 9
1	40-43	SPAE
2	221-224	SDPD
3	247-250	SVDE
4	256-259	TLID
5	277-280	SQRD
6	388-391	SSRE
7	402-405	SQEE
8	540-543	SPGD
9	635-638	TSQD

[5] PDOC00008 PS00008 MYRISTYL
N-myristoylation site

Number of matches: 13
1	24-29	GAVYSV
2	169-174	GSVRTF
3	181-186	GSAEAQ
4	273-278	GSVWSQ
5	283-288	GAAGAS
6	286-291	GASPTV
7	303-308	GCVLGS
8	307-312	GSVLGA
9	410-415	GSLPSK
10	425-430	GTFLTD
11	554-559	GSPPSS
12	568-573	GSPPAS
13	700-705	GTRNTL Membrane spanning structure and domains:
Helix	Begin	End	Score	Certainty
1	102	122	1.600	Certain
2	298	318	1.509	Certain
3	416	436	0.748	Putative

FIGURE 2B

BLAST Alignment to Top Hits:
CRA|160000003781983 /altid=gi|8650435 /def=gb|AAF78208.1|AF237669_1
    (AF237669) RalGDS-like protein 3 [Mus musculus] /org=Mus
    musculus /taxon=10090 /dataset=nraa /length=709
    Length = 709

Score = 1119 bits (2862), Expect = 0.0
Identities = 570/714 (79%), Positives = 623/714 (86%), Gaps = 9/714 (1%)

```
Query:   1  MERTAGKELALAPLQDWGEETEDGAVYSVSLRRQRSQRRSPAEGPGGSQAPSPIANTFLH  60
            MERTAGKELALAPLQDWGEETEDGAVYSVSLRRQRSQR +P E  G  Q P P +TFLH
Sbjct:   1  MERTAGKELALAPLQDWGEETEDGAVYSVSLRRQRSQRSTP-ERSGEGQTPIPATDTFLH  59

Query:  61  YRTSKVRVLRAARLERLVGELVFGDREQDPSFMPAFLATYRTFVPTACLLGFLLPPMPPP  120
            YRTSKVR LRAARLERLV ELV GDREQDP F+PAFLAT+R FVPTA +LGFLLPP PPP
Sbjct:  60  YRTSKVRALRAARLERLVHELVSGDREQDPGFVPAFLATHRAFVPTARVLGFLLPPPPPP  119

Query: 121  PPP--GVEIKKTAVQDLSFNKNLRAVVSVLGSWLQDHPQDFRDHPVHSDLGSVRTFLGWA  178
            PPP  GV+ K+T QDL+F+KNLRAVVSVLGSWL++HPQDFRD P H +LG+VR FLGW
Sbjct: 120  PPPPAGVDSKRTEGQDLNFSKNLRAVVSVLGSWLRNHPQDFRDPPDHQNLGNVRIFLGWV  179

Query: 179  APGSAEAQKAEKLLEDFLEEAEREQ-EEEPPQVWTGPPRVAQTSDPDSSEACAEEEEGLM  237
            APG AEA++AEKLLEDFL+EA+ EQ EEE    W+GPPR+AQT   + +E C EEE G
Sbjct: 180  APGGAEAREAEKLLEDFLKEAKGEQTEEEKRLAWSGPPRIAQTPGSEFAEDCVEEE-GPS  238

Query: 238  PQGPQLLDFSVDEVAEQLTLIDLELFSKVRLYECLGSVWSQRDRPGAAGASPTVRATVAQ  297
            +GP+LLDFSVD+VAEQLTL+D+ELF +VR  ECLGS+WSQRDRPGAAG SPTVRATVAQ
Sbjct: 239  SEGPELLDFSVDDVAEQLTLMDVELFLRVRSCECLGSMWSQRDRPGAAGISPTVRATVAQ  298

Query: 298  FNTVTGCVLGSVLGAPGLAAPQRAQRLEKWIRIAQRCRELRNFSSLRAILSALQSNPIYR  357
            FNTVTGCVLGSVL APGLAA QRAQR+EKWIRIAQRCRELRNFSSLRAILSALQSNPIYR
Sbjct: 299  FNTVTGCVLGSVLAAPGLAASQRAQRIEKWIRIAQRCRELRNFSSLRAILSALQSNPIYR  358

Query: 358  LKRSWGAVSREPLSTFRKLSQIFSDENNHLSSREILFQEEATEGSQEEDNTPGSLPSKPP  417
            LKRSWGAVSREPLS FRKLSQIFSDE+NHLSSR IL QEE TE   ++D   GSLPSK P
Sbjct: 359  LKRSWGAVSREPLSVFRKLSQIFSDEDNHLSSRAILSQEETTE---DDDCPSGSLPSKLP  415

Query: 418  PGPVPYLGTFLTDLVMLDTALPDMLEGDLINFEKRRKEWEILARIQQLQRRCQSYTLSPH  477
            PGPVPYLGTFLTDLVMLDTALPD L+G+LINFEKRRKEWEILARIQQLQ+RCQ Y+LSP
Sbjct: 416  PGPVPYLGTFLTDLVMLDTALPDTLKGNLINFEKRRKEWEILARIQQLQQRCQRYSLSPR  475

Query: 478  PPILAALHAQNQLTEEQSYRLSRVIEPPAASCPSSPRIRRRISLTKRLSAKLAREKSSSP  537
            PPILAAL AQ QL+EEQSYR+SRVIEPPAASCPSSPRIRRRISLTKRLSAKL+REK+SSP
Sbjct: 476  PPILAALRAQRQLSEEQSYRVSRVIEPPAASCPSSPRIRRRISLTKRLSAKLSREKNSSP  535

Query: 538  SGSPGDPSSPTSSVSPGSPPSSPRSRD-APAGSPPASPGPQGPSTKLPLSLDLPSPRPFA  596
             GSPGDPSSPTSSVSPGSPPSSPR+R+  P GSPPASPGPQ PSTKL L++D P P P
Sbjct: 536  GGSPGDPSSPTSSVSPGSPPSSPRNREPPPPGSPPASPGPQSPSTKLSLTMDPPGPWPVT  595

Query: 597  LPLGSPRIPLPAQQSSEARVIRVSIDNDHGNLYRSILLTSQDKAPSVVRRALQKHNVPQP  656
            L   S R+PL  QQ+SEARVIRVSI+N+HGNLYRSILLT QDKAPSVV+RAL+KHNVPQP
Sbjct: 596  LTPSSSRVPLLGQQTSEARVIRVSINNNHGNLYRSILLTCQDKAPSVVQRALEKHNVPQP  655

Query: 657  WACDYQLFQVLPGDRVLLIPDNANVFYAMSPVAPRDFMLRRKEGTRNTLSVSPS  710
            WA DYQLFQVLPGDR LLIPD ANVFYAMSP AP DF+LRRKEGT +TLS SP+
Sbjct: 656  WARDYQLFQVLPGDRELLIPDGANVFYAMSPAAPGDFLLRRKEGTGHTLSASPT  709  (SEQ ID NO:4)
```

FIGURE 2C

>CRA|103000001517213 /altid=gi|7682471 /def=gb|AAF67280.1|AF186779_1
    (AF186779) RGL protein [Homo sapiens] /org=Homo sapiens
    /taxon=9606 /dataset=nraa /length=768
    Length = 768

Score = 448 bits (1141), Expect = e-125
Identities = 291/744 (39%), Positives = 409/744 (54%), Gaps = 75/744 (10%)

```
Query:  11  LAPLQDWGEETEDGAVYSVSLRRQRSQRRSPAE----GPGGSQAPSPIANTFLHYRTSKV 66
            ++ +QDWGEE E+GAVY V+L+R + Q+ +      G  GQ P   +T    Y T K+
Sbjct:   9  MSSIQDWGEEVEEGAVYHVTLKRVQIQQAANKGARWLGVEGDQLPP--GHTVSQYETCKI 66

Query:  67  RVLRAARLERLVGELVFGDREQDPSFMPAFLATYRTFVPTACLLGFLLPPMPPPPPPGVE 126
            R ++A LE+LV L+    + D +++  FL+TYR F T +L LL        P E
Sbjct:  67  RTIKAGTLEKLVENLLTAFGDNDFTYISIFLSTYRGFASTKEVLELLLDRYGNLTSPNCE 126

Query: 127  IKKTAVQDLSFNKNLRAVVSVLGSWLQDHPQDFRDHPVHSDLGSVRTFLGWAAPGSAEAQ 186
                    +    S        A+ S+L +WL    +DFR+ P    L + +L   PGS   +
Sbjct: 127  EDGSQSSSESKMVIRNAIASILRAWLDQCAEDFREPPHFPCLQKLLDYLTRMMPGSDPER 186

Query: 187  KAEKLLEDFLEEAEREQEEEPPQVWTGPPRVAQTSDPDSSEACAEEEEGLMPQGPQLLDF 246
            +A+ LLE F    ++QE E     G P    S           EEEE   +   +   F
Sbjct: 187  RAQNLLEQF-----QKQEVETDN---GLPNTISFS-------LEEEEELEGGESAEFTCF 231

Query: 247  SVDEVAEQLTLIDLELFSKVRLYECLGSVWSQRDRPGAAGASPTVRATVAQFNTVTGCVL 306
            S D  VAEQLT +D +LF KV + CLG +WS+RD+        +PT+RAT++QFNT+T CV+
Sbjct: 232  SEDLVAEQLTYMDAQLFKKVVPHHCLGCIWSRRDKKENKHLAPTIRATISQFNLTKCVV 291

Query: 307  GSVLGAPGLAAPQRAQRLEKWIRIAQRCRELRNFSSLRAILSALQSNPIYRLKRSWGAVS 366
              +LG  L    QRA+ +EKWI IA  CR L+NFSSLRAI+SALQSN IYRLK++W AV
Sbjct: 292  STILGGKELKTQQRAKIIEKWINIAHECRLLKNFSSLRAIVSALQSNSIYRLKKTWAAVP 351

Query: 367  REPLSTFRKLSQIFSDENNHLSSREILFQEEATEGS-------QEEDNTPGSLPSKPP-- 417
            R+ +   F +LS IFSD NNHL+SRE+L +E ++ +            + + T  L  +
Sbjct: 352  RDRMLMFEELSDIFSDHNNHLTSRELLMKEGTSKFANLDSSVKENQKRTQRRLQLQKDMG 411

Query: 418  --PGPVPYLGTFLTDLVMLDTALPDMLEGDLINFEKRRKEWEILARIQQLQRRCQSYTLS 475
              G VPYLGTFLTDL MLDTAL D +EG LINFEKRR+E+E++A+I+  LQ  C SY ++
Sbjct: 412  VMQGTVPYLGTFLTDLTMLDTALQDYIEGGLINFEKRRREFEVIAQIKLLQSACNSYCMT 471

Query: 476  PHPPILAALHAQNQLTEEQSYRLSRVIEPPAASCPSSPRIRRRISLTKRLSAK-LAREKS 534
            P    +    Q LTEE+SY LS   IE A +  +SP+ R+    S+ KRLS    L +
Sbjct: 472  PDQKFIQWFQRQQLLTEEESYALSCEIEAAADASTTSPKPRK--SMVKRLSLLFLGSDMI 529

Query: 535  SSPSGSPGDPSSPTSSVSPGSPPS------SPRSRDAPAGSPPASPGPQGPSTKLP---- 584
            +SP+ +   P S   S S S S         +A  GS       P   P  KL
Sbjct: 530  TSPTPTKEQPKSTASGSSGESMDSVSVSSCESNHSEAEEGSITPMDTPDEPQKKLSESSS 589

Query: 585  -----LSLDLPSPRPFAL--PLGSPRI---------------------PLPAQQSSEA 614
                  S+D S    +L  PL SP                          P+ QQ+ +
Sbjct: 590  SCSSIHSMDTNSSGMSSLINPLSSPPSCNNNPKIHKRSVSVTSITSTVLPPVYNQQNEDT 649

Query: 615  RVIRVSIDNDHGNLYRSILLTSQDKAPSVVRRALQKHNVPQPWACDYQLFQVLPGDRVLL 674
            +IR+S+++++ GN+Y+SI+LTSQDK P+V++RA+ KHN+    A +Y+L QV+  D +L+
Sbjct: 650  CIIRISVEDNNGNMYKSIMLTSQDKTPAVIQRAMLKHNLDSDPAEEYELVQVISEDKELV 709
```

FIGURE 2D

```
Query: 675 IPDNANVFYAMSPVAPRDFMLRRK 698
            IPD+ANVFYAM+      DF+LR+K
Sbjct: 710 IPDSANVFYAMNSQVNFDFILRKK 733  (SEQ ID NO:5)
```

Hmmer search results (Pfam):

| Model | Description | Score | E-value | N |
|---|---|---|---|---|
| PF00617 | RasGEF domain | 226.4 | 4.3e-64 | 1 |
| PF00788 | Ras association (RalGDS/AF-6) domain | 60.6 | 3.8e-15 | 1 |
| PF00618 | Guanine nucleotide exchange factor for Ras-1 | 12.0 | 0.079 | 1 |

Parsed for domains:

| Model | Domain | seq-f | seq-t | hmm-f | hmm-t | score | E-value |
|---|---|---|---|---|---|---|---|
| PF00618 | 1/1 | 63 | 113 .. | 1 | 60 [. | 12.0 | 0.079 |
| PF00617 | 1/1 | 244 | 454 .. | 1 | 227 [] | 226.4 | 4.3e-64 |
| PF00788 | 1/1 | 613 | 700 .. | 1 | 112 [] | 60.6 | 3.8e-15 |

FIGURE 2E

```
   1 GTCCCCGCCC CACCTCCCTG GGGAAGCTCT CACTCCCCAA GGAAGCCCAA
  51 GACGTCAGAG ACCCTGTCCC GTCTCAAGCT CCGCCTCCAA GGGAAAGAAG
 101 TCCCACCCTG TCCCCGAAAA GCTCGGAGAC CTATCTGCAG TTCTGGAGCA
 151 GCCCGAGACA GAAGACCTAT CCTGCCCGCA GCAGAGGGCC ATTTCTTCAG
 201 GAGGCCATCC CACAATGGCC TCCCTCGAAT CCTTACTGTT CCCAAGAGGC
 251 CTCCCCGAAA CCTTTACATA TAGAGTTAGA GTTCAGAGGC TCCCCCATCA
 301 CAGACGTGGC CTTGACCTAA GTCCCCGCCC CCAATGGCTA GGATCGACCC
 351 TGCAGGTGGG CCCTTACCTC CTAGGCCCCG CCCCCGAAAG AAAAGCCCCG
 401 CCCCTGGGTG GAGCCTTCCA AGAGGCCCCA CCCCTCTCGG CTGACCCGGC
 451 TCTACCCTGG CCGCAGGAGG ACGGCCGCTT CGCGGGAAAG GAGCTGGATC
 501 CCCAGGCAGA TAACTATGTG CCAAACCTGC TGGGCCTCGT GGAGGAAAAG
 551 CTGCTGAAAC TGCAGGCGCA GCTCCAGGGC CACGACGTGC AGGAGATGCT
 601 GTGCCACATC GCTAACCGCG AGGTGCCCTG CAGCCATGGG GCAGAGCTCC
 651 AGAGATCTAG GAGTAGGGCT GGGTCGGAAA ACCAGGGAAC CGGGGGCAAC
 701 TTCGGGAGAC CAGATTGCAG GCTGATCAGC CAGGAAGGGG TCTCGGGGAC
 751 AACGGGCGAG GTTTGACGAG CCAGGGGTGA GCCCGAGCCA CGAGGGAAGA
 801 AACCAGAAGA GGTGCAGGCG GGTCCTGTGA GGCTAGAGGA CGCGGCTGGG
 851 GTATCCGGAT GGGGAGAGGC CTAGTGGCAG GGCCCCAGAG ACCAGGGGCG
 901 GACCTGAGTG ATGAGGGGGT GAAGCTGGGT ATCAAGGTGC CTGCTTAAGG
 951 AGGGATGGGA GTGGGCAGTG GTCTCCAGTT GGAACTAGGG CATATCTCGG
1001 AATGGGGTAG GGAGGAGGGG GAACGTGACT TCTCGGTGGC CCCTGGCCCC
1051 GCCCACCTTC CTCTCTCGCT TCCCATCCCC GCTTAGTTCC TCGCCAGCTT
1101 AGAGGGAAGG CTGCCCGAAT ACAACACCCG CATCGCCCTG CCCCTTGCCA
1151 CTTCCAAGGA CAAGTTTTTT GGTCAGTATG GGTGGGGGGA TGAAGGGGTG
1201 CGGTTGGGGC CCCAAGCTGG GTAGCAGGAG GTTGTCAGAT ACCCTGTTCA
1251 GGGCCAAGGT GGGGGTGGAG TGGGGTGGTA AAGGGAAGGG GAGCCAGGGA
1301 TGGGGACCTG GATCCCACAT CGCTCCCTGC TCATCCCCCC ACCCCCCTTA
1351 GACGAAGAGA GTGAGGAGGA GGACAACGAG GTAGTGACCC GCGCATCACT
1401 CAAGATCCGT TCCCAGAAAT TAATCGAAAG TCACAAGAAG CACCGTCGCT
1451 CTCGGAGGTC CTAGACTCGT CCTGACACCG ACCAGGCGGC CCCTTCGGAG
1501 CCCCCGAATC TCCGGGTCTA GCGCACGCCA CGGGCGCTTC AGGGGCTGAA
1551 CGCGGCCGGA CCGGGAACGG AGGCGGCCAG CGGCGCCCGG AGGGGAGGAA
1601 GGGGCCGGGC CAGACGTTCC CACAGTAAAT CTCCCCAGCT GGGTCCGCCC
1651 CGGCCTCAGA GTTGCGCAAT AAATGTTACC GACCATGCCC CTGGGTATTC
1701 ATCTGTTTTT GACCCTGCAC CACCCAAGAG ACGGCTGTCC CTGAAAACCC
1751 AGGGCCACAG ACTGCCTCCT CCAACCTGGG TCATGATGAC TCCCATCAGC
1801 TAGTGACGCA GATGGAGCTT AAAAATGGGA GATGGCCCGA TGTAGTGGTT
1851 TTATGCCTGT AATCCCAGTA TTTTGGGAGG CTGAGTTGGG AGGATCACTT
1901 GAGTCCAGGA GCTCCAGGCT GCAGTGAGCT ATGATCGTGC TACTGCACTC
1951 CAGCCTGGGC CACAGAGCCA GACCCTGTCT CAATAAATAA AATAAGGGCG
2001 GGGTGCAGTG GCTCATTCAT ACCTATATTC CCAGCACTTT GGGAGGCTGA
2051 GCTGGGTGTG TCGCTTGAGC CCAGGGGTTC CAGACTAGCC TGGGCAACAT
2101 GGTGAAAACC AGTTTTTACC AAAAAAAAAA AAAAAAAAAA AAGCTGAGCA
2151 TGGTGGCATA TGCCTGTAGT CCCAGCTACT GGGAGACTG AGGCAGGAGA
2201 ATGGATTGAA CCCAGGAGGC GGAGATTGCA GTGAGCCAAG ATCAAGCCAC
2251 TGCACTGCAG CCTTGGCAAC AGGAGTGAGA CCCTGTCTCT AAAAAATAAT
2301 AAGGCTGGGC GCCGTGGTTC ATGCCTGTAA TCCCAGCATT TTGGGAGGCT
2351 GAGGTGGGCG AATCTCTTGA GGCCAGGAGT TTGAGACCAG CCTGGCAAGT
2401 ATGGCAAAAC CCCGCCTCTA CAAAAAATAC AAAAATTAGC TGAGCATGGT
2451 GGCGGCACCT GTAATCCTAG CTACTTGGGA GGCTGAGGCA CAAGAATCCT
2501 TTGAATCTGG GAGGCGGAGG TTGCAGTGAG TTAAGATCAA GCCACTGTAC
2551 TCCAGCATGG GTGACAGAAC GAGACTCCAT CTCAAAATAA TAGCAATAAT
2601 AATAAAAAGT GGAAGATGCC CCCACACTTG ATCAAGCTAG CCCCTTCCAC
2651 TGGAGGACAG AGGACTCTGG TCTGGGGACA CACACATGCC CCCACACAGG
2701 AGCTCCCCCA CATCTGGGGA TACAAAAAAG ACCCCTTGGG GACAGATATG
2751 TCCTTTCTTC TGGGACAGA TTGATAGGCA CCCAGCGGAA GAGCCAGGAC
2801 CTCTCCTGGG CTGGCGCTGG GTCGGCTGG AGGCACCCAG AGGCTGGGTC
2851 CGGCCTGCCC TGCCCCGCCC CGCCCCAGCA GCTCGGCCGC TCCGCCCCTC
2901 TGGCCTCAGC GCCCGGCCAC TGCCCGCCGC CCGCCACCCG CCACCCGCCG
```

FIGURE 3A

```
2951 GCCCTTCCGC CTCACTCAGC GGCGCCACTG AGAGGGACGG GCGCCGGCCA
3001 TGGAGCGCAC AGCAGGCAAA GAGCTGGCCC TGGTAAGGGG ACAAGGGATC
3051 CCCGGACCCC GCATCCCTGG TGACCCGCAG GTCCAGAAAC TCCAAGCGCC
3101 CGCCCGTCGG ACGGTATCTG CTCCCAATCT GAACTTGCCC TGGAGTCCCC
3151 TCCTGGGGAC TCGCGGCCCT TGACCCAGTG AAGCGACTGG TTCCTCTTAG
3201 GGATGGGGGC GCGAGTCTCT GAGCGCAGTC GGCAGAAAGA GCTAGAGACA
3251 GGTTCTATTA GACTGGGCCC TGGGACATCC CCAAATGCCA CCCCATGTCC
3301 TCAGGACCTG GGAGGAGGGG ACCCGCAGCG AGGAGGGGAC TAGCCTGGGA
3351 CCCCAGCCCT AGTCTCGCAG CTTCTGGCCG GAAGGGGCG TGGGGATGCA
3401 GCAGGAGGAC TCGGCCCGAG TCCGAGCGGC CAAGGAGGCT GAGGCCCCAG
3451 GACCTGTGCC CCTTTGGTGC CCTGAGTCCG CCTGTGCGTC CAGGCACCGC
3501 TGCAGGACTG GGGTGAAGAG ACCGAGGACG GCGCGGTGTA CAGTGTCTCC
3551 CTGCGGCGGC AGCGCAGTCA GCGCAGGAGC CCGGCGGAGG GCCCCGGGGG
3601 CAGCCAGGTG AGGAGGGGGT TTGGTGGGTG GCGCGGGGCC GGAAGCGACC
3651 AGTTGAGGGC GGAGCTGGAG AGCCGAGCAC AGGCCGCCAG GTGCAGTGGG
3701 CGGAAGGAAG GGAGGGGCTC GGAGGCGACC AGATGAGGCG ACCAGGTAGA
3751 AAGGGGACTG GGGGCGGCCA GGTAAGTGGG GGGAGATCCA GGGAATGGGG
3801 TGGGGCCAGG CGATGCCGC GCAGTTCCCG AGAGGAGCCT AGGGACAACT
3851 TGGTAAGGAC AGAACTGGAC GGCAGAGTTG GGAAAGGCAG GTTTAGAGGG
3901 CCGGGGCTGG AAGGTGGAAT GGGGTTGGTT TAGCAAGTGG CTAGGTGAGG
3951 GCGGATGGGG CAGCCAGTGA AGCGCGACAG GAGGGCTGAG GGAAGCCCTG
4001 GGTGGAAAAG AGTGTGTGGG GCGGGGGCGG GGGGGTGGGG GGAGGGGACG
4051 GGAGGGGAG GGGACGGGAG AGGGAGTAGG GGACAGGGCA TGGAGAGGG
4101 AGGGTTTCCA GGGCAAGTTG CAGGAGCTAT TTGTGGATGG GGAGGAACAA
4151 TAACTTCAAG CGGGCAGGGA GTGGGCACA CACCTATAAT CCCTGCGCTT
4201 CGAGAGACCA AGGCAGAAGG CCAGGAATTG GAGACCAGCC TGGACAACAC
4251 AGCAAGATTC TCTCTAATAA AAATAAAAAT TAAAAAACTA GCTGTGCGTG
4301 ATGATGCCCA GCAGTGGTCC CAGCTACTCA GGAGGCTGGG GCAGAGGGAC
4351 CGCTTGAGTC TAGGACTTGG AGGCTGCAGT GAGCTATGAT TGTGCCACTG
4401 CACCCCAGCC TGGGCAACAA AACAAGACCT GTTTCTAAAA AAAACAAACC
4451 AAAACAATAA CTCCAAGAAG CCGGGAGACA GAGGAATCAC ATGAAAGAAT
4501 GGTGCTACAG GCGGGGCGAG GTGGCTCACG CCTGTAATCC CAGCACTTTG
4551 GGAGGCCGAG GCAAGTGGAT CATCAGGTCA GGAGTTCAAG ACCAACCTGG
4601 CCAAGACGGT GAAACACCGT CTCTACTAAA AATACGAAAA AACTAGCTGG
4651 GCTTGGTGGC GGGTGCCTGT AATCCCAGAT ACTTGGGAGG CTGAGGCAGA
4701 GAATTGCTTG AACCCAGGAG GCGGAGGTTG CAGTGAGCCA AGATCACGCC
4751 ACTGAACTCC AGCCTAGGTG ACAGAGTGAG ATTCTGTCTC AAAAAAAAAA
4801 AAAAAAAAGT GGTGCTAGGG GCTGGGCACG GTGGTTCACG CCTGTAATCC
4851 TAGCCCTTTG GGAGACTTTG GGAGGCCAAG GGGGGCAGAT TACTTGAGGT
4901 CAGGAGTTCG AGACCAGTCT GACCAACATG GTGAAACCCT ATCTCTACAA
4951 AAATACAAAA ATTAGCTGGG CTTGGTGGTG TGCGCCTGTA GTTTCAGCTA
5001 CTTGGAGGCT GAGGAAGGAG GATTGCTTGA ACCCAGGAGG CAGAAGTTGA
5051 AGTGACCCAA GATCGTGCCA CTGCACTCCA GCCTGGGCAA CAGAGTGAGA
5101 CTCTGTCTCA AAAAAAAAAA CAAAAAAAAA AAGAGTGGTG CTAGTGATGA
5151 ATGTGACTAG AGAAGGGGTG CTGTGAGGAC CACTCCTGCT CTCTCATGGC
5201 CACCTCTCCC CTCCTGCAGG CTCCCAGCCC CATTGCCAAT ACCTTCCTCC
5251 ACTATCGAAC CAGCAAGGTG AGGGTGCTGA GGGCAGCGCG CCTGGAGCGG
5301 CTGGTGGGAG AGTTGGTGTT TGGAGACCGT GAGCAGGACC CCAGCTTCAT
5351 GCCCGCCTTC CTGGCCACCT ACCGGACCTT TGTACCCACT GCCTGCCTGC
5401 TGGGCTTTCT GCTGCCACCA ATGCCACCGC CCCCACCTCC CGGGTCAGTA
5451 GCGAACCATA ACCTCCGTAT TCTCCACCCT AGAACCCCAA CTGGGCACCC
5501 CCCTCCACCT CCTCAGGTGT GGAACCTGGA AACACCTCCC AGACCAGAG
5551 CCCTCTTCCT AAGCCCCCTC TAGGTTCCCC CTTCTTCACC TGCTGGGGGG
5601 CCTCTTCCCA GGGTAGAGAT CAAGAAGACA GCGGTACAAG ATCTGAGCTT
5651 CAACAAGAAC CTGAGGTGGG TCCTTCATCC AGATAGGGGA GTGCGGGGAG
5701 GGAAATCCAA GAGGTCAAAG GTTAGCAGTC GGACTGGGGT TTTGAAAATT
5751 GCAGGTTGGG TAATAAGAGA CTGGGAGTCA GGTGGGGCGT GGTGGCTCAT
5801 GCCTGTAATC CCAACACTTT GGGAGGCCGA GGCAGGTGGA TCACTGGAGG
5851 TCAGGAGTTA GAGACCATCC TGGCCAATAT GGCGAAACCC TGTCTCTACT
```

FIGURE 3B

```
5901 AAAAATACAA CAACAACAAA AAAAGGTAGC TGGGTGTGGT GGCGCATGCC
5951 TGTAGTCCCA GCTACTCGGG AGGCTGAGGT TGCAGTGAGT CAAGATCAGG
6001 CCATTGCACT GCAGCCTTGG TGACACAGTA AGACTCTATC TCAAAAAAAA
6051 AAAAAAAAAA AAGGTACCAG GAGTCATATT CTATGTCCCC CACTCTGGAC
6101 CCAGCTCTGA GACCCTGCCT CTCTGGCCAG GGCTGTGGTG TCAGTGCTGG
6151 GCTCCTGGCT GCAGGACCAC CCTCAGGATT TCCGAGACCA CCCTGTCCAT
6201 TCGGACCTGG GCAGTGTCCG AACCTTTCTG GGCTGGGCGG CCCCAGGGAG
6251 TGCTGAGGCT CAAAAAGCAG AGAAGCTTCT GGAAGATTTT TTGGAGGAGG
6301 CTGAGCGAGA GCAGGAAGAG GAGCCGCCTC AGGTGTGGAC AGGTGAGGGG
6351 TTTTCAGATC CAGTCGTGTT CTGAGAAGGC CTTTCCTGTC TGCTTCTTCC
6401 CACACAGGCT TTCTCTCCCC TCTCAGAGCT ACAAAACTTA AGCAAGATTT
6451 TAAACTCTAA GCCTCAATTT CTTCATCTTT ACAATGGGGA TAATAATTCT
6501 TTGTCAGCCG GGCGTGGTGG CTCACGCCTG TATCCCAGCA GTTTGGGAGG
6551 CCAAGGATGG TGTATCACCT GAGGTCAGGA GTTTGAGACC AGTCTGACAA
6601 ACATGGAGAA ACCCCATCCC TACTAAAAAT ACAAAATTAG CCGGGCGTGG
6651 TGGGGCATGT CTATAATCCC AGCTATTCGG GAGGCTGAGG CAGGAGAATC
6701 GTTTGAACCC GGGAGGCGGA GGTTGCGGTG AGTCGAGATC GTGCCATTGC
6751 ACTCTCGCCT GGACAACCAG AGCGAAACTC CGTCTAAAAA AAAAAACAAA
6801 TTCTTTGTCT GAAGTATTAG CATGTGTCTA ATACTTTTCC CTCCTTGGTG
6851 CCGTTGGGTC AGGATGCTCT GTGTTTCTAG CTACAAACCA TTGCCTTGAT
6901 ACTTGTCTTT ATTTTCTTTT TTTTGAGTCA GGGTCTTGCT CCGTTGCTCA
6951 GGCTGGAGTG CAGTGTCTCC ATCATGGCTC AGTGCAGGCT CAACATCCTG
7001 GACTCAGGTG ATCCTCCCGC CTGGGTCTCC AAAACTGCTG GCATTACAGG
7051 CGCGAGCCAC TATACCTAGC CTGTAAAATT TTTCTTATTT TTGAATTTCT
7101 TTTTAAATTT AATTTAATTT AATTTTATTT TTTTATCTAT TTTTTTTTTT
7151 AGACAGAGTC TCGCACTGTT ACCCAGGCTG GAGTGCAGTG CACAATCTT
7201 GGCTCACTGC AACCTCCACC TCCTGGGCTC AAGCCATTCT CCTGTCTCAG
7251 CCTCCTGAGT AGCTGGGACC ACAGGCGCAT GTCACCACGC CCGGCTAATT
7301 TTTTTGTAAA GGTGAGGTTG TGCCATGTTG CCCAGGCTGG TCTCAAACTC
7351 CTGAACTCAA GTGATCTGCC TGCCTTGGCC TCCCAAAATG CTGGGATTAC
7401 AGCCATAAGC CATTGTGCAT GCGTAGCCTC CTTACTTGAT TATTGGCTTT
7451 TGCTCATCTC ATAGGCTGTG AGTGCATGAG AGGAGGACCT GTTGTTCTTG
7501 CTCCCAGCTC TGTCCCCAGG GGCAGGAACA ACACAGATTA GTTTGCTGAA
7551 TAATTGCATC CTGCTTAGGA AGTATCATCT TTCACCCATC TGTATTTGAT
7601 CTGATCCACA TCACAAAAGC ATCTCTATCC CTAATCCCCA TCGCTTAATC
7651 TCCAGATTAT AGAGGCCACC TTCCTGTCCA ATTTACAAAG TAGCAGCCAC
7701 TTCTCTATCC CTGGTGACAA AGTCTCAGTT ATTTATATAT ATATAAAGGT
7751 ATATATATAT ATATATATAT ATATATATAT ATATACATGA AGGTGTATAT
7801 ATATATATAT ATATGAAGGT ATATATATAT ATGTATATAT ATGAAGGTAT
7851 ATATATATAA AGGTATATAT ATATAAAGGT ATATATCTAA AGGTATATAT
7901 ATATATAAAG GTATATATAA GGGTATATAT ATATAAAGGT ATATATATAT
7951 ATATGAAGGT ATATATATAT ATGTATATAT ATGAAGGTAT ATATATATAA
8001 AGGTATATAT ATATAAAGGT ATATATATAA AGGTATATAT ATATATAAAG
8051 GTATATATAT ATAAAGGTAT ATATATATAT AAAGGTATAT ATATATAGGT
8101 GTATATATAT ATATATATAT ATATATATAT ATATATATAT ATATGATTTC
8151 TCCAGCTGAT TCCAAGTCAT TAGAGCTCCA TAGTTCACTG TGGTATCCAC
8201 TAGCACCTGT CGCTATTTAA ATTAATTAAA ATTGGCTGGG CGCGGCGGCT
8251 CATGCCTATA ATCCCAGCAC TTTGGGAGGC CGACGGGGGC GGATCCCAAG
8301 GTTCGGAGAT CGAGACCATC CTGGCTAACA TGGTGAAACC CCGTCTCTAC
8351 TAAAAATACA AAAAAATATT AGCCGGGCGT GGTGGCGAGC GCCTGTAGTC
8401 CCAGCTACTC GGGAGGCTGA GGCAGGAGAA TGGCGCGAAC CTGGGAGGCG
8451 GAGCTTGCAG TGAGCTGAGA TCAAGCCACT GAACTCCAAC CTGGGTGACA
8501 CAGCGAGACT CTGCCTAAAA AAAAAAACC AAAAAACAAA ATTATAATAA
8551 TAATTAATTA ATTAATTAAA ATTAAATAAA ATTCAGGTCT TTTCTTTTTA
8601 GAGATGGGGT CTTGCCATGT TGCCCAGGCT GGTCTCGAAC TCCTGGGCTT
8651 AAGCAATCCT CCAGCATCAA CCTCTCAGAG TGCTGGGATT GTAAGTGTGA
8701 GCTACTGTGC CTGACCCTGC CTTTTTTTTT TTTTTTTTTT TTTTGAGACG
8751 GAGCCTCGCT CTGTCACCCA GGCTGGAGTG CAGTGGCGCC ATCTCGGCAC
8801 ACTGCAACCT CCTCCTCCCA GGTTCAAAAG ATTCTCCTGC CTTAGCCTCC
```

FIGURE 3C

```
 8851 CAAGTAGCTG GGATTATAGG CACCTGCCAC CACACCCAGC TAATTTTGTA
 8901 TTTTTATTAG AGACAGCGTT TCACTATGTT GGTCAGTCTG GTCTTGAACT
 8951 CCTGACCTCA GGTGATCCAC CCACCTCGGT CTCCCAAAGT GCTGGGATTA
 9001 CAGGCGTGAG CTACCATGCC TGGCCCGCTT TTTTTTTTTT TTTTTTTCTT
 9051 TTTCAAAATC CAGTCAAGCA AAGGCAAAAA TTCAGGTCTT CAATCCCACT
 9101 ACCCACATTT TGAGTGCTCA GCCACCACAC TGGACATAGC AGATAGATAA
 9151 TTTTTCCACC ATTGCAGAGA ATTATATGGA AAGTGCTGCC CTAGTTTCTT
 9201 TGAGGTCAGA GGAGAAAATT AACATTTGTT TAAGACCTTC TATGTGCTAG
 9251 GCCCTGGGAC ACACTTTATT TCATTTTATT TTATTTTATT TATTTTTACT
 9301 TTTATTTTAT TTTGAGACAG AGTCTCGCTC TGTCGCCTAG GCTGGAGTGC
 9351 AATGGCGCGA TCTTGGCTTA CTGCAACCTC CACCTCCTGG GTTCAAGTGA
 9401 TTCTCCTGCC TCAGCCTCCT GAGTAGCTGG TACTACAGGC GCCCGCCACC
 9451 AGGCCCAGCT AATTTTTTGT AGTTTTAGTA GAGACGGGGT TTCACCGTGC
 9501 TAGCCAAGAT GGTCTCGATC TCCTGATCTC GTGATCCGCT TGCCTCGGTC
 9551 TCCCAAAGTG CTGGGATTAC AGGCGTGAGC CACCGCACCC GACTATGAAT
 9601 TTTATTTTTA GATACAGGGT CTTGCTCTGT TGCCCAGGCT GGACTCGAAC
 9651 TCCTGGGCTC AAGTGAGCCT CCTACCTCAG CCTCCTGAGT AGCTAAGACT
 9701 ACACTTGCAC CATGTAGTTT AGAAGAAAGT AGATGACCAC CATGCTCATC
 9751 TATTTTATTT TAACAACTTT ATTTTGGGTT CACTTTTTGC TATGGAAAAT
 9801 TTCAGACATA TACAAAAGTA GAGAGAATAG TATGAAGAAC ATTCAGACAT
 9851 CCATCACCTA TCATCAACGA TGATCAATTT CACAAAAAAA TATTTTCAGG
 9901 ATGATTTTAA AACAAATCCC GGGCTTATGT CAATTCATAC ATAAATGTTT
 9951 TGGGTACACA TGTCTGACAA CAGGCTTACT TTTTTTTTTT TTTTTTTTGA
10001 GACGGAGTTT CGCTCTTGTT GCCCAGGCTG GAGTGCAATG GCAGGATCTC
10051 AGCTCACCTC AACCTCTGCC TCCTGGGTTC AAGTGATTCT CCTGCCTCAG
10101 CCTCCCGAGT AGCTGGGATT ACAGGCGTGC ACCACCACAC CCGGCTAATT
10151 TTCTATTTTT AGTAGAGAGG GGGGTTTCTC CATGTTTGTC AGGCTGGTCT
10201 CGAACTCCTG ACCTCAGGTG ATCCGCCCAC CTTGGCCTCC CAAAGTGTTG
10251 GTATTACAGG CGTGAGCCAT GGCGCCCGGC CCTTTTATTT TTATTTTTTA
10301 ATAACCTTCA TGTTCATACT TAAAAAAAAA TCAGAAATAT TTGATATAAA
10351 AAAAATCCAA TCCAGGCCAG ATGCAGAGGC TCCTGCTGGC GATCCCAGCA
10401 TTTTGGGAGG CCAAGGCAGG TGGATGGGCT TTGAGCCCAG GAGATTGAGA
10451 CTAGCCTGGG CAACATGTTG AAACTTTGTG TCTACAAATA ATTAGCTGGG
10501 CATGGTGGTG ACTGCCTATA GTCCCAGCTG CTTGGGAGGC TGAGGCAAGA
10551 GGATCATTTT AGCCTGGGAT GGTCAAGGCT GCAGTGAGCC GTGATTATGC
10601 CACTGTACTC CAGCCTAGGT GACAGAGCGA GACCCTGCCT CAAAAACAGA
10651 AAAAATACCC AGTCTATATT CAAATATTCA AATCCCCTGT TTGTGCCTGA
10701 ACCTTTTTTT GGACACTGGG TTTTCCTATT TTGCCTGGGC TGGGCTTGAA
10751 CTCCTGACCC TCCCACCTCA GCCTCCTGAG TAGCTGGGAC CACAGGTGCC
10801 CACCATGGCA CCCAGCCCTA AATTTTCTTT TGACAGTTGT TTCTGGCCAG
10851 GTGTTGTGGC ACATGCCTAT AGTCCCAGCT ACTTAGGATG CTGAGATGGG
10901 AGGATCTCTT GACTCCGGGA AATCAAAAGC TGCCGTGAGC TGTGAGCATG
10951 CCCCTGCACT CCAGGCGATA GAGCTGGGGG AAGGAGGAAT AGTTGTTTCT
11001 TCAAATTGAA ATCCAAAGAT CTACTCAAGG TATTTGGTTG TTTGCTTCTC
11051 TTTTTTTTTT TTTTTTTTTT TTTGAGATGG AGTCTCACTC TGTTGTCCAG
11101 GCTGGAGGGT AGTGGCGTGA TCTTGGCTCA CTGCAACCTC CGCCTCCTGG
11151 GTTCAAGCGA TTCTCCTGGC TCAGCCTCCT GAGTAGCTGA GTTACAGGT
11201 GCCCACCAAC ACGCCCAGCT AATTTTTGTA TTTTTAGTAG TGAGGGGGTT
11251 TCACCATGTT GGCCAGGCTG GTCTTGAACT CCTAACCTTT AGTGATCTGC
11301 CCACATCGGC CTCCCGAAGT GTCGGGATTA CAGACATGAG TCACCACGCC
11351 CTACCGGTCG TTTGTTCATA AGTCTCTTTT ATTCTGTAAC AGATCCCCCT
11401 TGCCTCTTGT TTGAAGCCAT TAGAGGGCAA AAAAAATGGG TCATTTTTCC
11451 TGAGGTATGT CTCACATTCT TTTCGACTTA CCTCATGGTT TCATGCAGCA
11501 TGTTTCTCTA TCCCCATAAT TGCTGTAAGA TTTAAAGGTT TGATTAGATG
11551 TAGGGCATTT TTTTTTCCAG GGCCCACTTT TTTTTGGGGT GGGGGGAGGA
11601 GAGACAGTTT CTTGCTCTGT CACCCAGGCT GGAGTGCTAT GGCATGATCA
11651 CAGCTCACTG CAGCCTTGAC CTCCTGGGCT CAAGAGATCC TCCCTCCTAA
11701 GCCTCTTGAG TAGGTGGGAC AGCAGGTGTG CATCAGGATG CGCAACTTTA
11751 AAAATTTTTT TATGTAGACA TGGGGTCTCA CTACGCCGCC CAGGCTGGTC
```

FIGURE 3D

```
11801 TCAAACTCCT GGTCTCAAGC AATCCTCCTA CCTCAACCTC CAAAAGTGCT
11851 GGGACTATAG GTGTGCCCAG CCCAGTACCC ACTTCTAAAA ACTAATATTT
11901 TGCAATGCCA CCTGTCCTAA TTCAAGATGA AAGAGGTAAT TACACAGATT
11951 TACAAAGATT ATTTTAAAAT AATAGTATTG GGGCAGGGTG CTATGGCTCA
12001 TGCCTGTAAT CCCAGCACGT TGGGAAGCCG AGGCAGGAGG ATCACCTGAG
12051 GTCAGGAGTT CGAGACCAGT CCGGCCAACA TGGTGAAACC CCATCTCTAC
12101 TAAAAAAAAT AAAAAATAAA ATAAAATAAA ATAAAAAATA AATAAATAAT
12151 AAAAAAATAT ATATATATTT AAATTAGCTG GCTGGGCATA GTGGCACCTC
12201 CTGTAGTCCC AGTTGCTCAG GAGGCTGAGG CAGGAGAATT GCTTGAACCC
12251 TGGAGGCAGA GGTTGCAGTG AGCCGAGATC GAGCCACTGC ACTCCAGCCT
12301 GGGCGACAGA GCAAGACTCC ATCACAAAAT AAAAAAATAA AATAAAATAA
12351 TAGTATGATG CCATAACTAG TACAAAGGAG AAGGAAAGTG AGAGTAACTT
12401 ACACAGCAAT AAACCATGTT TTCAATGGGT AATGCTTGGG TATGCCCCAC
12451 TAGGACACAT GATGAGGTTG TCCCGTGTCT TTGCCTGTCC TAGCGTCACA
12501 GTAGAGTGTC ACGGTGCTGT TGTACTGACA GCAACAAGCA CCAACGAACG
12551 CACAGGAGGG CACTGGTGAG GCAAAGACAG CAACATAGGT TCTGGGGACA
12601 TCATTTTCCA AACTTGTGAA CAACATTTGC AATTTGCAAA CAAAACAAAG
12651 CCCAGACTTT CGTGGTCCTT GCATTCTTGG AGCCAAAAAA ATTTGTGTTT
12701 ATGAACAAAA TAGTCAGGTT CTAGGTGCAT ATTATTGCAA ACATGTTTTT
12751 CTTTTCTTTT TGTTTTTGTT TGTTTGTTTG TTTTGTTTTG TTTTGTTTTT
12801 TGAGATGGAG TCTCGCTCTG TCGCCCAGGC TGGAGTGCAG TGGCATGATC
12851 TCGGCTTACT GCAAGCTCCG CCTCGCCGGT TCACGCCATT CTCCTGCCTC
12901 AGCCTCCTGG GTAGCTGGGA CTACAGGCGC CCGCCACCAC GCCTGGCTAA
12951 TTTTTTCTAT TTTTTAGTAG AGACGGGGTT TCACCATGTT AGCCAGGATG
13001 GTCTCGATCT CCTGACCTCG TGATCTACCC GCCTTGGCCT CCCAAAGTGC
13051 TGGGATTACA GGCGTGAGCC ACTGCCCCG GCCTTCTTTT CTTTTCTTTT
13101 TTTTTTTTTT TTGAGACAAA GTCTCTGTCA CCCAGGCTAG AGTGCCGTGG
13151 CGTGGACCTG GCTCACTGCA ACCTCCACCT TCTAGGTTGA GGTGATTCTC
13201 TAGCCTTAGC CTCCCGAGCT GGGATTACAG GCACTTGCCA CCATGCTCAG
13251 CTGATTTTTG TATTTTTAGT AGAGACAGGG TTTCGCCATG TTGGCCCGAC
13301 TGGTCTCGAA CTCTTGACCT CAAGTGATTC GCCTGCCTTG GCCTCCCAAA
13351 GTGCTGGGAT TACATGTGTG AGCCACTGTG CCAGACCCCT TCTTCCTTTC
13401 TTAAAGACAA GTCAAGTGCA GTAGTGAGAA GGGGGGAAAG AGTAGAACAA
13451 GGAGTTCGAT CTGTAACTGT GAACAATCAA TTGAGATAAG TCACTACCTT
13501 GGGACCAGCC ACAAACAGGT TTTTCAAAGA CACAAATGTC TGGAGATACA
13551 TTTGGAGGCT AGAGGGCACA ATTCAGGATC CCAGTTTCCA AAGTTTCCCC
13601 TCCAGGGTGC CACCATCAAA ATCCACTAAA GTAAAATTAT TCATATTTGT
13651 TCAGCACTTT ATAGCAGTCT GGTAGCATGA TCTTTTTTTT TTTTTTTGAG
13701 ATGGAGTCTC GCTCTGTCGC CAGGCTGGAG TGCAGTGACA CGATGTCGGC
13751 TCACTGCAAG CTCCGTCTCC AGGGTTCAAG CGATTCTCCT GCCTCAGCCC
13801 CCCGAGTAGC TGGGATTACA GGCGCGTGCC ATCACGCCCG GCTAATTTTT
13851 GTATTTTTTT TTAGTAGAGA CGGGGTTTCA CCGTGTTGGC CACGCTGGTC
13901 TCGAACTCCT GACCTCAGGT GATCCACCCG CCTCGGCCTC CCAAAGTGCT
13951 GGGATTACAG GCGTGAGCCA CAGCGCCCGG CAGCATGATC TTAAACGAAA
14001 ACAAAAACGA AATCCACAGC CAGGCGCACT GGCTCACACC CGCAATCCCA
14051 AAACTTTGGG AAGCCAAGAG GGAGGATCGC TTGAGCCCAG GTGTTTGAGA
14101 CCAGCCTGGC AACATAATGA GACCCTGTCT CTACAAAAAA TAAAAAATTA
14151 GCTGGGCATG GTGGTGTGTG CCTATAGTCC CAGCAACTCA GGAGGCTGAG
14201 GCAGGAGGAT CACTGGAGCC CAAAAGGTTG AGGCTGCAGT GAACTGTGAT
14251 CACACCACTG TACTCCAGCC TGGGTGACCA AGGGAGAGCC TGTTTCAAAA
14301 AGAAGGCACA GCTTACCCCT GCAATCCCAG CACTTTGGGA AGTCGAGGCA
14351 GGCAGATCCC TTGAGGTCAG GAGTTCAAGA CCAGCCTGGC CGACATGGTG
14401 AAACCCTGTC TCTACAAAAA TACAAAAGTT AGCTGGGCGT GGTGGCTCAG
14451 TGCCTGTAAT CCCAGCTACT TGGGAGACTG AGGCAGGAGA ATTGGTTGAA
14501 ACCTGGAGGC GGAGGTTGCA GTGAGCCAAG ATCACGCCAT TGCATTCCAG
14551 CCTGGGCGAC AGAGTCAGAC TCCGTCTTAA AAAAAAAAAA AAAAAGGCAC
14601 AGAGAGGTTA AAATACATGC TCTACACAGC AAGCTAGTGG ACGAGTTTGC
14651 ATCTGAGTTT GAGACTTTCT GACAATAGCC TTCCCTGAAC CAGGAAGTCG
14701 TATCACCTCT TTCCAAAAAA AAGAGGTCAG ATTAATCTTA TCCTAATACA
```

FIGURE 3E

```
14751 TGTTAAAAAT CATAAAGCTC TATTTTCTTC TCTGGCCTTT GAGTACCCGG
14801 CTTCAAACCC CTGCCCTGCC ATTTACCAAA GGTGTGACAA ATTGTTCTTT
14851 GCCTCCCTTT CCTTAATTGT AAAAGGTGGA TAAATAATAG TACCTCCCTC
14901 ACTGGACTCA CAGTAACTCA GTGGTGAGTT ACTGAGTAAA TCCACACTAG
14951 CTGCTTAGTG AACATTACTG TTGCTGTTAC ATCCTTAAAA ACACTCAGGG
15001 CCAGGCGTGG TGGCTCACAC CTGTAATGCC AGCACTTTGG GAGGCCAAGG
15051 CGGGCAGATC ACTTGAGGTC AGGAGTTTGA GACCAGCCTG GCCAACATGG
15101 TGAAAGCCCG TCTCTATTAA AAATACAAAA ATTAGCCGGG CATGGTGGCA
15151 CATGCCTGTA ATCCCAGCTA CTCAGAAGGC TGAGGCAGGA GAATCACTTG
15201 AACCCAGGAG GCGGAGGTTG TGGTCAGCTG AGATTGCGCC ATTGTACTCC
15251 AGCTTGGGCA ACAGAGTAAG ACTGTCTCAA AAAAAAAAAA AAATTTAAGA
15301 GAGCTCTCCG TTTTACAAAT GAGGAAAGTG AGCCTCAGAG AGGGACAGGG
15351 ACTCACCCAA GGTCACACAG CCAGTCTTGG ATTCAAACTT GAGAGTTTGT
15401 AACCCTTTCT AATGATCAGG ACCTCCCAGA GTTGCCCAAA CTTCTGACCC
15451 AGACTCTTCA GAGGCCTGCG CGGAGGAAGA GGAAGGGCTC ATGCCTCAAG
15501 GTCCCCAGCT CCTGGACTTC AGCGTGGACG AGGTGGCCGA GCAGCTGACC
15551 CTCATAGACT TGGTGAGGAT CCCGGACAGG GTCGGGATGA GCCACAGTGA
15601 GGGGACAGGT TCTGCTAAGC ACCAATCCCA CACCCCTCCC CTGGCCCAGG
15651 AGCTCTTCTC CAAGGTGAGG CTCTACGAGT GCTTGGGCTC CGTGTGGTCG
15701 CAGAGGGACC GGCCGGGGGC TGCAGGCGCC TCCCCACTG TGCGCGCCAC
15751 CGTGGCCCAG TTCAACACCG TGACCGGCTG TGTGCTGGGT TCCGTGCTCG
15801 GAGCACCGGG CTTGGCCGCC CCGCAGAGGG CGCAGCGGCT GGAGAAGTGG
15851 ATCCGCATCG CCCAGGTGTG TTGCGGGCGC GGAGAGGGGA TGCGGGGGCG
15901 GGCCCTGGGG CAAGGGGAAA AAATGAGGGC TCCGGAGAGA GATAGGGGCG
15951 AGTCTAGGCG AGGGAGGGAA CGGGGTGGAA AGTTGATACC TAGGGTGAGA
16001 CTTGGGTTCA GGGAGGAGGG TCTGGGTCCT GCAGAGAGGC CGCGGGCACG
16051 ACTAGGTCCC AAGGGAGCTG GGAGAAGTAG GGAGCCCGGA CCGGAGAAGT
16101 CAAGGTCGGA GGCAGGGGCT GGAGGGGCAG CTGGGGAGGG GCTGGAGCCC
16151 GAGGGAGGAG GGAGGAAGGG AATCCTAGGG AATAAGTGGG AGTCTTGGTA
16201 GCTTGTCGGA TGTGAGACAA CACCCAGGGG TCCGACCTGG CGTCACAAGT
16251 CACGGGATCA GGCTGGGCGC AGTGACTCAC GCCTGTAATC CAGCACTTT
16301 GGGGAGAGGG AGGATCGCTT GAGCCCTTGA GTTTGAGACC AGCCTAGGCA
16351 ACATAGTGAG ACCAATGTTT CTAGAAAAAA AAAAAAAATT AAAAAAATTA
16401 AAAATGAGAC TTACAAAAAA ATTAGCCGGG TGTGGTGGTG TGCCCCTGTA
16451 ATTCCCAGCT ACTTGGGAGG CTGAGGCAGG ATAATCACTT GAACCCGGGA
16501 GGCGGAGGTT GCAGTGACTC GAGATCGGGC CACTGCATTC CAGCCTGGGG
16551 GATAAAGCGA GACTCTGTCC AAATAATTAA TAATAATAAT AATAATAAGC
16601 CATGCATGAT GGCGCGCGCC TGTAGTCCCA GCTACTGAGG CAGGAGGCTG
16651 AGGCATGTGG ATCGCTTAAG CCCAGGAATT CCAGGCAGCA AGTGAGCTAT
16701 GATCGAGCCC CTGCACTCCA GCCTGGGCCA CAGACCCTAT TTTTCAAAAA
16751 AAAAAAAAAA AAAAAAAAAA AAAAAAAAAA AAAAAAGAT GAAGAAGTTT
16801 CAGGATGAAA GGTGGATAAT GCCTGGGTCT GACCTGCGTC CCCACCGCCT
16851 GGCAGCGCTG CCGAGAACTG CGGAACTTCT CCTCCTTGCG CGCCATCCTG
16901 TCCGCCCTGC AATCTAACCC CATCTACCGG CTCAAGCGCA GCTGGGGGGC
16951 AGTGAGCCGG TGAGCTGGGG CGGGACCTGT TCCCCAGCCC ATCCCAGGTC
17001 TGACCCTCCC AAGCCACTGA CCCCTGACCA CCCTTCTCCT GTCCTTCCAG
17051 GGAACCGCTA TCTACTTTCA GGAAACTTTC GCAGATTTTC TCCGATGAGA
17101 ACAACCACCT CAGCAGCAGA GAGATTCTTT TCCAGGTAGA GATGGATGCA
17151 GACTCCAGGG ATTTTAGGCC CGGGAAGTCG GGGAGGGAC TTGGGGCCAG
17201 GCAGGGGTAA TCTCCCTGCT ATAGTCAGGA CACTCTGTCC TTCCCTACCG
17251 CTCAGCAATG ACCTTATCCT TGTCCCTGGC GGGTTGCACG TTTTTCTTTC
17301 CTCTACTTCC TGCGTTATAG TTGACTGTCA GTGACTGCCC TATTTATTCA
17351 CTCAGCAAAA CACAAGAAGT CACAAAGAAA AGGTTACTTA AGGCCAGAGT
17401 CATAGCACAG GGTGGGAACA AAAAAAATGT TCTGAGGACT TTACCTTGAT
17451 AAGCAAAACT AAAAAATGTG TGTCAAAAGT CTGGCTTATT TATAGGCAAG
17501 ATTTAGATTC TCATTGCAAT CAGGCGCTGG TTTTTAGAGT GAATCTAGAA
17551 TGGATCCCTG GGCCTGGAAC ATTCTCCACC CCTCCAGGTT TGCATGCAAC
17601 TTGCTCACTC ACCTCCTTCT GGTCTCTGAT TAAATGTCCC TGCCTCTGAG
17651 AGGCCTTCCC AGCCTCCATC ATCCCCAAAA CCACACATCT GGTTTTTTGT
```

FIGURE 3F

```
17701 TGTTGTTGTT GTTGTCGTCA TCATTTGTTT TTTTGTTTCT TTGTTTGTTT
17751 GTATTGAGAC AGAGTCTCGC TCTGTCACCC AGACTGGAGT GCAGTGGCAC
17801 GATCTTGGCT CACTGCAACC TCCACCTCCC AGGATCAAGC AATTCTCTCT
17851 GCCTCAGCCT CCCATGTAGC TGGGATTACA GGCACCCACC ACGACGCTTG
17901 GCTAATTTTT GTATTTGGTA GAGACGGGGT TTTGCCGTGT TGGCCAGGCT
17951 GGTCTCGAAT CCCTGACCTG AGGTGATCCA CCTGCCTTGG CTTCCCAAAG
18001 TGCTGGGATT ACAGGCGTGA GCCATCACTC CCAGCCAAAT TTCACCTGGC
18051 TAACAGAGTG AAACCCTGTT TTCCTGCCCA GCACCTAGAA CAGCACGTGA
18101 GCTGGGCTCA GTGACTCACG CCTATAATCC CAACACTTTG GGAGGCCAAG
18151 GTGAGAGGAT CACTTGAGCC CAGGAGTTCA AGACCAACCT GGGCAACATG
18201 GCAAAACCCC ATCTCTGCAA AAAATACAAC AATTAGCTGG GCGTTTGTGG
18251 TGCACGTCTG TAGTCCCAGC TATTCAGGAG GCTGAGGAGG GAGGATCGCT
18301 TGAACTTGGG CGGTCAAGCC TTCAGTGAGC CAAGATCAGG CCACTGCACT
18351 CCAGCCTGAG TGACAAAGTG AGACTCCATC TCAAAATAAA ATGAAATAAA
18401 AAGTAAGTAA ACAACAGCAA ATTCAGGATA CCCAGGAGAT CCCTGGCAGG
18451 CCTGTGCCAT CCAGCTGCGG ACAAGGATTC TCTCCTTGTT AAGGCCAGCC
18501 CTGGGGGCCA CTACCCACAA GCCCCACCTC TCATGGGGCC TGCTCCCTGC
18551 TGTTTATCTC CTCCCTACCC TCATCCAAGG TGGTCTGGCT TCTAGAGTGG
18601 GCCTTAACCC CTGGCTTCTT TTTTTTTTTT TTTTTTTTTT TGAGATGGAG
18651 TTTTGGTCTT GTTGCCCAAG CTGGAGTGCA ATGGTGCGAT CTTGGCTCAC
18701 TCCAACCTCC GCCTCCCGGG TTCAAGCGAT TCTTCTGCCT CAGCCTCCCG
18751 AGTAGCTGGG ATTACAGAAA TATGCTACCA TGCCCAGCTA GTTTTTTATA
18801 TTCTTAGTAG AAACAGAGTT TCACTCTGTT AGCCAGGCTG GTCTCAAACT
18851 CCTTACCTCA TGTGATCCAC CAGCCTCGGC CTCCCAAGTG CTGGGATTAC
18901 AGGCGTGAGC CATCGCACCT GGCCTACCAC TGACTTTTGA TTACTCAAAG
18951 CATGAAGGGT ATATATGATG GGTCTGCAGG CATCGTTCCT GAGGAATTGT
19001 CCAAGGAGAC CCCAGACCTG GCTCAGTTTT TCTCTTCCCT CAGGAGGAGG
19051 CCACTGAGGG ATCCCAAGAA GAGGACAACA CCCCAGGCAG CCTGCCCTCA
19101 GTGAGTGATT ACAGTTTGGG ATGGGACAA GTGGGACCTT CAGGGAGGGT
19151 TGTGGATGGT GATGGGGTCA GTAATGGCCC CAAGTGACTG GAGCTTTGGG
19201 GGCTGCAGAA ACCACCCCCA GGCCCTGTCC CCTACCTTGG CACCTTCCTT
19251 ACGGACCTGG TTATGCTGGA CACAGCCCTG CCGGATATGT TGGAGGTCTG
19301 ACCCCTGACC CTTGACCCCT GACCCCAGCT CCACTTGCCC CCAGCACAAT
19351 GGGCCTCCCA ATATCCACCC TTGATCCTAC CTGTACTCCT GACACCACCC
19401 CACACTCCCT TACTACAGTG GGGCTCCTGA CATCCCAGCC CCTGACCTTG
19451 ACCCTTGACC CTTGACCCTG GGTGCTGCAA TTCAGACACA CTTTGCCCCC
19501 AGGGGGATCT CATTAACTTT GAGAAGAGGA GGAAGGTGAG TGGAGGCTAC
19551 AGTGGGTGTG GTGGTGCCTG AGGGTGGGGG TGGGCAGGG GTAGGGTCTT
19601 AGAGGCTCGT CCTCCAGGAG TGGGAGATCC TGGCCCGCAT CCAGCAGCTG
19651 CAGAGGCGCT GTCAGAGCTA CACCCTGAGC CCCCACCCGC CCATCCTGGC
19701 TGCCCTGCAT GCCCAGAACC AGCTCACCGA GGAGCAGAGG TGACCACCCT
19751 GTAGCCTGTC CCAGCCCCAC CCCAGCTGAG CCTGGGTCAC CAACTGGATT
19801 CCACCCACTC CATACACACC TCCAGCTCCT CCCAAGACCC CCTCTTGAGC
19851 CCTGATCCCC CACTACAACC TGTGACCTTG CAGTATCTCC AGTCGAATCA
19901 AATAGACTGG GCCTGGTGGT TTACTCGTGT AATCCCAGCA CTTGGGAGGC
19951 CAAGGTGGGT GGATCACTTG AGCCCAGGAT TTCGAGACCA GCCTGGGCAA
20001 CATGGCGAAA CCCCATATCT ACAAAAAAAT ACAAAAATTA GCTGAACGTG
20051 GCTGGGCACG GTGGCTCACA CCTGTAATCC CAGCACTTTG GGAGGCCGAG
20101 GCGGGTGAAT CACATGAGGT AAGGAGTTTG AGACCAGCCT GGCTAACAGA
20151 GTGAAACCCC GTCTCTACTA AAAATACAAA AAAAAATTA GCCAGGTGTA
20201 GTGGCAGGCG CCTGTAGTCC CAGCTACTTG GGAGGCTGAG GCAGGAGAAT
20251 GGCGTGAACC CGGGAGGCAG AGCTTGCAGG GAGCCGAGAT GGTGCCACTG
20301 CACTCCAGCC TGGGCAACAG AGCGAGACTC CGTCTCAAAA AAAAAAAAA
20351 AAAATTAGCT GAATGTGGTG TTGAGTGCCG TTGGTCCCAA CTACTTGGGA
20401 GGCTGAGGTG GGAGGATTGC TGGAGCCTGG GAGGCAGAGG TTGGAGTGAG
20451 CCAAAATCAC GCCACTGCAG TTCAGTCTA GGTGACAGAG TGAGACCCTG
20501 TCTCAAAAAA AAAAAAAAAA AAATAGTCAC AATTGACCTC TGACCTCAAT
20551 TTCAACCCCA TCTGATTTTC TGACCTCAAC TTTAGCATTC AGCTGGCCAT
20601 TCAACTCAAC TGTCCCATCT GTTGACTTCC CCATCTTTGG TCCTATCTGA
```

FIGURE 3G

```
20651 CCCATGACCT TATTCATGAC CCCTCATCTG ACTCTCTGAC CCCAACCCTT
20701 GACCCTCAGT TCTGAGTAAC TGACTCCAAC TTTTATGTTT GACTGTCCAG
20751 CTTGACTATG ACAACTGTGT CCTTTCTTTC TATATAACTG TGACCCTAAC
20801 CATTGACCCC AATGGTGACC TGACCCCAGT CTGACCCTGA CTTTATTTTA
20851 TTTATTTATT TATTTATTTA TTTATTTATT TATTTATTTA TTTTTGAGAC
20901 AGAGTCTGGC TCTGTTTCCC AGGCTGGAGT GCAGTGGAGT GATCTCGGCT
20951 CACTGTAGCC CCCGCCTCCC AGGTTCAAGC AATTCTACTG CCTCAGCCTC
21001 CCCGGTAGCC GCAATTACAG GCGCGAGCTA CCACACCTGG CTAATTTTTT
21051 TTGTATTTTT AGTAGAGACG GGGTTTCACT ATATTGGCCA GGCTGGTTTC
21101 GAACTCTTGA CCCGAAGCAA TCCTCTCGCC TCAGCCTCCC AAAGTGCTAG
21151 GATTACAGGC GTGAGCCACT GCACCCAGTC CTGACCCTGA CTTTAATCCT
21201 GACCCAATTT GATTCCTTAG TGCCACCCTG TGAATCTCTT TGTGACCTCC
21251 TGACCAGCCA TCCTGTCCCA TCTCTGATAA GACCTTGATG CTCAATGACC
21301 CTCATTTACC ACCCTGACCC TGGCATGTGG GGTGCCACCT CTGGCTGCTC
21351 CCCCTTACAC CCCAAACCCA CCTCCCAACT GATTCCAACT CTTATCTCTC
21401 CATCCCCTGT ATTTCCTGCC CCCACCACCT CATCCACATA TTGACCCCTC
21451 AGCTACCGGC TCTCCCGGGT CATTGAGCCA CCAGCTGCCT CCTGCCCCAG
21501 CTCCCCACGC ATCCGACGGC GGATCAGCCT CACCAAGCGT CTCAGTGCGT
21551 GAGTCTCGGG GTGTGTGTAG GGGCGGTGAT GTGGGCAGAT ATCAGCAAGG
21601 GCTGCTCCTG CCTTAGCCTC ATCCCTGTC CCATCCTTA GGAAGCTTGC
21651 CCGAGAGAAA AGCTCATCAC CTAGTGGGAG TCCCGGGGAC CCCTCATCCC
21701 CCACCTCCAG GTGAGCATTC TGCTTGGTGA TGGGACTGGG GATCATGGGA
21751 TCAGGAGTCA GCACAGCCAC CCCACCTCAG CCTCTGCATC TCCCCCAGTG
21801 TGTCCCCAGG GTCACCCCCC TCAAGTCCTA GAAGCAGAGA TGCTCCTGCT
21851 GGCAGTCCCC CGGCCTCTCC AGGGCCCCAG GGCCCCAGCA CCAAGGTACC
21901 AAGACGGCTT GTGTGTGCAT GCGGGCCTGC GGGCACCCAG GCTCTGTGTG
21951 TGTGCACGTG TGTGTGCATG CACATGTGTA CACACAGGAT TGTGGGGCCA
22001 GGAGTGTATA CAGGAGGCAC ACTGAGCGCC CGGGGTATCC ATCCAGGGGA
22051 TTGCATGCAT CTGCACGGCC CTGTTTGGGT GATCACTCAT AAATCCGACT
22101 CGTGCTCAGA TTTGGACCTG TGTAACTGCT TGCCCATGGG TCATCTAGGG
22151 TGCAATCACA TCACACCCCT TTTTATTTGA AACAGGGTCT TCTTGCTCTG
22201 TCACCCAGGC TGAAGTGCAG CGGTGCAATC TCAGCTCACC GCAACTTCCA
22251 CCCCTCCCCC AGGCTCAAGC AATCCTTCCA CCTCAGCCTC CCAAGTAGCT
22301 AGGACCACAG GTGTGCACCA CCATGCCCTG CTATTTTTTT TATTTAGTAG
22351 AGATGAGGTT TCGCCATGTT GCCCAGGTGG GTTTCGAACT CCTGAGCTCA
22401 AACAATGCAC TCACCTCGGC CTCCCAAAGT GCTGGGATTA CAGGTGTGAG
22451 CCACCGCACC CAGCCTACAC TTTTTTGAGG ACATGTATGT CCCTAAGAAT
22501 CTGCATACCA TGGCAGACAC GGTGGCTATT GCCTGTGATC CCGGCACTTT
22551 GGGAAGCCAA AGTGGGAGGA TTGCTTGAGG CCGGGAGTTC AAGACCAGCC
22601 TGGGCAACAT AGTGAGACCC TATTTCTATT AAAAGTCAAA AAAATTAGCT
22651 GGGTGTAGTC CCAGCTACTC AGCAGGCTGA GGTGGAAGGA TCGCTTGAGT
22701 TTGAGGCTGC AGTGAGCTAC GATCATGCCA CGGCACTCTA GCCTGCATGA
22751 TAGAGCGAGA TCCTGTTTAT GAAGAAAAAG AGACTGGGCA CGGTGGCTCA
22801 CGCCTGTAAT CCCAGCACTC TGGGAGGCCG AGGTGGGCGG ATCACGAGGT
22851 CAAGAGATCG AGACCATCCT GGCCAACGTG GTGAAACCCT GTCTCTACTG
22901 AAAATAGAAA AATTAGCTGG GTATGGTCGC GCACACCTGT AGTCCCAGCT
22951 ACTTGGGAGG CTGAGGCAGG AGAATCACTT GAACCCAGGA GACGGAGGTT
23001 GCAGTGAGCT GAGATGGTGC CACTGCACTC CATCCAGCCT GGTGACAGAG
23051 CGAGGCTCCC TCTAAAAGAA AAACAAAAAA AGAAAAGGAA ATGAAGGAAA
23101 TGAAGGCTGG GCATGGTAGC TCATGCCTGT AATCCCAGCA CTTTGGGAGG
23151 CCGAGGCCAG TGGATCACTT GAGGCCAGGA ATTTGAGACC AGCCTAGCCA
23201 ACATGGTGAA ACCCCGTCTC TACTAAAAAT AAAAACATTA GCTGGGCATA
23251 GTGGCACAGG CCTGTAATCC CAGCTACTTG GGAGGGTGAG GCATGAGAAT
23301 TGCTTGAACC TGGGAGGCAG AGGTTGCAGT GAGCTGAGAT GGCACCACTG
23351 CATTCCAGCC TGGGTGACAG AGCAAGACTC TGTCTCAAAA AAAAAAGAAA
23401 AGAAAAAGAA AAGAATCTGT GTACCAGAAG AGGAAATGTG GGCCTGAGTA
23451 TTCATGAGAT CATGTGTGGG GTTGTTCATT GGCATGGGCT GTGGGTGTAT
23501 AACCGCTGTC AGCATATGTA TGTACACAGG ATTTCTTGTT TATGAGCATG
23551 GGTTGTGTGT ATATGGACAC TGTTCATGTC TGTTTCTATA ACAGGTAACC
```

FIGURE 3H

```
23601 AAAGTCTGTA TATGGTAGGG TGGTGTATAT GCAGGCTTGT GAATGTACTC
23651 CAGTTGCATG TCCCAGGCTC TGCATGTGTA GGGGGTAGTA GTATGTTTTC
23701 TTGAGATTTT ATTTTATTTT ATTATTTATT TATTTATTTT TGAGATGGAG
23751 TCTTGCTCTG TCACGCAGGC TGGAGTGCAG TAGCGTGATC TTGGCTCACT
23801 GCAACCTCTG CCTCTCAAGT TCAAGTGATT CTCCTGCCTC GGCCTCCCAA
23851 GTAGCTGGGA TTACAGGCAT GCGCCACCAG GCCCTGCTAA TTTTTGTATT
23901 TTTAGTAGAG ACGGAGTTTC ACCACGTTGG CCAGGCTGGT CTTGAACTCC
23951 CGACCTCAAG TGATCCGCCC ACCTCGGCCT CCCAAAATGC TGAGATTACA
24001 GGCATGAGCC ACTGCGCCCA GCCAATGTTT TCTTGAGATT TTAAATGTGG
24051 GGCTATTGAA TGCACCAGTG GTGGCTGGGG TGTTCGTGCT TTTCTAGCCC
24101 TCAGCATCTG CAGATGGGCC AAGCTGTAGC CTCCACCCCT TACTGCCTGC
24151 AGCTGCCCCT GAGCCTGGAC CTGCCCAGCC CCCGGCCCTT CGCTTTGCCT
24201 CTGGGCAGCC CTCGAATCCC CCTCCCGGCG CAGCAGAGCT CGGAGGCCCG
24251 TGTCATCCGC GTCAGCATCG ACAATGACCA CGGGAACCTG TATCGAAGCA
24301 TCTTGGTGAG GGGCTGGGCT GGGGGTCTGC TGGAGGCTGC CCTGCCCTTG
24351 GGGCCGGGGC CCTCACCTCA CCTCCCGCCC CTCTCTTCCA GCTGACCAGT
24401 CAGGACAAAG CCCCCAGCGT GGTCCGGCGA GCCTTGCAGA AGCACAATGT
24451 GCCCCAGCCC TGGGCCTGTG ACTATCAGCT CTTTCAAGTC CTTCCTGGGG
24501 ACCGGGGTGA GCAGGGATGG GTTGGAGCTC AGGATAGGGG GCAGCGGGGA
24551 GGCGAGCAGA CTGACCACGC CCAAGGATGG AGCCCAAGGT TACCCGGGTT
24601 CACAGGGCTG TGAGGTGCTT CAGGCAGAGA GTAGGGGTAA GATAATCAGT
24651 GGAGGTAAGA GGACATAAAA TACCTGTAAC CCAACGATGT AGGGTCATGA
24701 GATTGTCTTG GCTCAGTGTG AGAGAGAGGT ACCAAAGGTC ATCTTCCTAA
24751 AATTTAAAAG ACAATAAGAT TGTCCAGGGT CCGGCCAGGC GCAGTGGCTC
24801 ATGTCTGTAA TCCCAGCACT TTGGGAGGTC AAGCTGGGCG GATCACTTGA
24851 GGTCAGGAGT TTGAGACCAG GCTGACCAAC GTGGTGAAAC CCCGTCTCTA
24901 CGAAACATAC AAAAATTAGT CGGGTGTGGT GGCACACTCC TGTAGTCCCA
24951 GCTACTCAGG AGGCTGAGGC AGGAGAATAA TTGCTTGAAT CTGGGAGGCG
25001 GAGGTTGCAG TGAGCCGAGA TCATACCACT GCACTTCAGC CTGGGCAGCA
25051 GAGCGAGACT CTGTTTAAAA AAAAAAAAA AAAAAAAGAC TGTCCACGGA
25101 CAAGTGACAG AAGGGAGTGT TTCTGACCTT CAATTTGTAG GATGGGCTGG
25151 GCATGGTGGC TCACAACTGT AATCCCAGCA CTTTGGGAGG TCAAGGTGGG
25201 TGGATTGTCT GAGCTCAGGA GTTTGAGACC AGCCTGGGCA ACATGAGGAG
25251 ACCCCATCTA TACAAAAAAT AGAGAAATTG GCTGGGTGCG GTGGCTCAAC
25301 GCCTGTAATC CCGGCACTTT GGGAGGCCAA AGCGGGTGGA TCACTTGAGG
25351 TCAGGAGTTC GAGACCAGCC TGGCCAACAT GGTGAAGCCC CGTCTCTACT
25401 AAAAATACAA AAAATTAGC TGGGCATGGT GGCACATGCC TGTAGTCTCA
25451 GCTACTCGGG AGGCTGAGGC AGAAGAATCG CTTGAACCCA GGAGGCGGAG
25501 GTTGCAGTGA GCCGAGATCG CACCACTGCA CTCCAGCCTG GCGACTGAGC
25551 AAGACTCTGT CTCAAAAAAA AAAAAAAAAA AAAAAAAAAA AAAAGCCAAT
25601 ATATATATAT ATATATAGAG AGAGAGAGAG AGAGAGAGAG AGAGAGAGAG
25651 AGATTAGCTG AGCATGGTGG CATGTGCCTG TATTCCCAAC TCCAACTACT
25701 GGGGAGGCTG AGGTGGGAGG ATCACTTGAG CCTAGGAGGT GGAGGCTGCA
25751 GCGAGCTGAG ATCACGCCAC TGCACTCCAG CCTGGGTGAC AGAGCAAGAC
25801 CCTGTCTCAA TTAAAAAAAA AAAAGGGGGC CGGGCATGGT GGCTCACGCC
25851 TGTAATCCCA GCACTTTGGG AGGCCGAGGC GGGTGGATCA CGAAGTCAAG
25901 AGATCGAGAC CATCCTGGCC AACATGGTGA AGCCTCGTCT CTACTAAAAA
25951 TACAAAAAAT TAGCCAGGCA TGGTGGCAGG CGCCTATAGT CCCAGCTACT
26001 CAGGAGGCTG AGGCAGAAGA ATCACTTGAA CCCAGGAGGT GAAGGTTGCA
26051 GTGAGCCAAG ATTGCGCCAC TGCACTCCAG CCTGGCGACA GAGTGAGACT
26101 CCGTCTCAAA AAAAAGAAA AAATAGATTG TCTAGGGTCG AGTGAGAGAA
26151 GGGAGTGTAG AAGTTTGTCT GATCTTAAGT TTGTAGCATC ATGAGATTGT
26201 TCAGGCTCAA CCTGATGGGA TGGGAGACTA AAGGGCATCT GGGCTTAGAT
26251 TTGTGAGAAC TAAGTTTGTT CACCACTGGG ACCCTGAAGT TATCTGAACT
26301 TGGGACGGGA GAGAGGCAAA TGGATAGCCG CGGAAGCATG AGATTGTCCT
26351 GTCTGACAGG GAGAAGCAAG GGATTGACG TATTCACGCT GAAGTACATG
26401 GCATGAGGTT GGCTGGATAT TAGGAAAGGA TGCTTGTGGT TGTTCAGGTG
26451 TTGAGTGTGA GGCCACAAGC TCGTGCAGGC TGGAAGTGGG AAGTTATTCA
26501 AGTTCATGGT GACAGCAGCA TGGGATTGGC TGGGAGTGGT TGTGGGGGAG
```

FIGURE 3I

```
26551 GGGTAGGGTG AGCAGGAAGT TGTTTGGCGG GGGGTGGTCT AGGGTGGTCT
26601 AAGTTTGCCC AAACTTTTAC TGCAGGTTGT CGGTTTTGTT TGTTTTTGTT
26651 TTTTTTTTTT TGAGATGGAG TCTCGTGCTG TTGCCCAGGC TGGAGTGCAA
26701 TGGCAGGATC TCGGCTCACC GCAACATCCA CCTCCTGGGT TCAAGAGATT
26751 CTCCTGCCTC AGCCTTCCGA GTAGCTGGGA TTACAGGCAT GTGCCACCAT
26801 GCCTAGCTCA TTTTTTTTGGT ATTTTTAGTA AAGACGGGGT TTCACCATGT
26851 TGGCCAGACT GGTCTCGAAT TCCTGACCTC AAGTGATCCA CCCACTTCGG
26901 CCTCCCAAAG CGCTGGGATT ACAGGCACGA GGCATCGCGC CCGGCCAGTT
26951 TGCTCAAACT TTTACTGCAG GTTGCCTTGT CTCTATGGTG AGGGGGAGAA
27001 TATTAGGAGG TTGCCCAGGC TTATGATAAG GGAAGGCATG AGGTGGTGCA
27051 AGTTTTCAAG TGAGAAGTCG TCCAGGTTCC CAGTGACAGC AGAATGAGCT
27101 TGGCTTGGCA GTAGCTGCAG AGGGACCCAT GGCTGTTCAG GTTCGCGGGT
27151 GAGTGGCAGG AGGCTCCCGG GTCCTCTGTG GGGGTGACAC AAGGTTGTGA
27201 GGGCCTATTA CCACCATCTC CACTCCTGAC CAGTGCTCCT GATTCCTGAC
27251 AATGCCAACG TCTTCTATGC CATGAGTCCA GTCGCCCCCA GAGACTTCAT
27301 GCTGCGGCGG AAAGAGGGGA CCCGGAACAC TCTGTCTGTC TCCCCAAGCT
27351 GAGGCAGCCC TGTCCTCTCC ACAAGACACA AGTCCCACAG GCAAGCTTGC
27401 GACTCTTCTC CTGGAAAGCT GCCATCCCCC AGTAGAGGCC ACTGTGCTGT
27451 GTATCCCAGG ACCACCACCC AACTGTAGCC CATTGGACCC CATCTCTTTT
27501 TCTGACTCTG TTGGTACTAG ATCCATATTC CAAAGACATC AGCCCATGGG
27551 TGGCTGGTGG AGAGCTCAAT CCCATAAATG TAGAAAGAGG TGGGGCATGG
27601 ATACGTCAAA TCCCTCCCCA GAGAAATCTT ATAAATGTTA GAGACGCATC
27651 AGAAGTGACA GATGCGGATG AAAATAGTGA CCAGAGTTAT GAAACAGGTG
27701 TCAGTCTTGT TTATTTTGCG CCTGTGTGCC ATGTTCACCC TTTATCAAGA
27751 TAAAGGAAAA CAGCTACCAC ACACACACCC ACACACACAC ACACAAACAC
27801 ACAGAGAGAG AGAAACCTAA GAGCCAAGAC CAGCCCGGGC AACATAACGA
27851 GATCCTGTCT CTACAAAAAA TACAAAAATT TGGCTGGGCG TGGTGACTCA
27901 CGCCTGTAAT CCCAGCGTTT TGGGAGGCCA AGGCAGGCAG ATCGCCTGAG
27951 GTCAGGAGTT CGAGACCAGC CTGGCCGACA TGGCAAAACC CCATCTTCTA
28001 AAAGTACAAA AAATTAGCCG GGCGTGGTGT CATGCACCTG TAATCCCAGC
28051 TACTGGGGAG GCTGAGGCAG GAGAATTGCT TGAACCCGGA AGGTGGAGGT
28101 TGCAGTGAGT GGAAATCACA CCACTGTACT CCAGCCTGGG TGACAGAGCA
28151 AGACCCTATC TCAAAACAA ACAAACAAAC AAATGAACAA ACAAAAAATT
28201 TTCTGAGTGT GGTGATATGA GACTGTAATC CTACCTACTT GGGAGGCTGA
28251 GCTGGGAGAA TCACCAGAGC CCTGGGAGGT TGAAGCTGCA GTGAGCAGTG
28301 ACTGGGCCCC TGCACTCCAA CCTGGAGGAC AGAGGGAGAT CCTGTCTCAA
28351 AAACAAAAAA ACTAAGAGCC CTAAGAAAGG TGTTGAGTCG GGTATGACAC
28401 TCAACCCAGA TGCCAGAGAG GATCCTGTCT GGCCGGACAC AGTGGCTCAG
28451 GAGGGTAATC CCAGTACTTT GGGAGGCTGA GGTAAGAGGA TTGCTTAAGT
28501 TCAGGAGTCC GAGAGCAGCC TGGGCAATAC AGTGAGATCA CATCTCACTA
28551 AATAAATAAA TAAAGGATCC TATCACACAA AGAGGGTTTA GGACTTCCTT
28601 CCCCAACATT TTTGGGGTGA TATGCCTCTT TTCTACTGTA TATATGGGAG
28651 AGTGACTAAC TGAAATTCCA TCAGAATTAG AAACAAATAG CATCATTACC
28701 CATGAGTCAA TAAGGGCTGT GAGGATGGGC CCTTTCACTT GCCCTCACCT
28751 TCTTCCTCTT CCTGTCACAG ATAACCCATC TGTGCAAAGA AGAGAAAAAG
28801 AGGTTGGGTG TGGTGGCTCA CATCTGTAAT CCCAGCACTT TGGGAGGCTA
28851 AGGTGGAAGG ATTTTGAGCC CAGGAGTTTG AGACCAGCCT GGGCAACATA
28901 GTGAGACCCC ATTTCTACAA AAAAATACAA AGATTGGCCA GGCGCGGTGG
28951 CTCACGCCTG TAATCCCAGC ACTTGGGAGG CTGAGGCAGG CGGATCATGA
29001 GGTCAGGAGA TCGAGACCAT CCTGGCTAGG TGAAACCCCG TCTCTACTAA
29051 AAATGCAAAA AAATTAGCCG GGCGTGGTGG CGGGCGCCTG TAGTCCCAGC
29101 TACTCGGGAG GCTGAGGCAG GAGAATGGCG TGAACCCAGG AGGCGGAGCT
29151 TGCAGCGAGC CGAGATCGCA CCACTGCACT CCAGTCTGGG CGACAGAGGG
29201 AGACTCCATC TCAAAAAATA AAATAAAATT TAGCCAGGTT TGGTGTCCTG
29251 CACCTGTAGT CTCAGCTACT CTGGAGGCTG AAGCACGAGG ATCACTTGAG
29301 CCCAAGAGGT GGAGGTTGCA GTGAGCCGAG ATTACTGCAC TCCAGCCTGG
29351 GTGACAGAGC GAGATCCTGT TTCAAAAAGC AAAAAAAAGG GCCAGGCGCA
29401 GTGCTCACAC CTGTAATCCC ATCATTTTGG GAGGCTGAGG TGGGCGGATC
29451 ACTTGAGGTC AGGAGTTCAA GGTCAGCCTG GCCAACATGG TAAAACCCTG
```

FIGURE 3J

```
29501 TCCCTACTAA AAAATATAAA AATTAGCTGG GCATGGTGGT GGGTGCCTGT
29551 AATCCCAGTT ACTCAGGAGG CTGAGGCAGG AGAATTGCTT GAATCCAGAA
29601 GGTGGAGGTT GCAGTGAACC GAGATCATGC CATTGCACTC CAGCCTGCGT
29651 GACAAAGTGA GACTGTATCT CAAAAAAAAA AAAAAAAATG CTGGGCACAG
29701 TGGCTCTAGC ACTTTGGGGG GGCAAGACGG GTGGATTGCT TGAGGCCAGG
29751 ATTCCAAAAC CAGCCTGGCC AACATGGTGA AACCCCTTCT CTACTAAATA
29801 TACAAAAAAT TAGCCGGGCA TGGTGGCAGG CTCTTGTAAT CCCAGCTACT
29851 CGGTAGGCTG AGGCAGGATA ATCACCTGAA CCAGGCAGGC AGAGGTTGCA
29901 GTGAGTCGAG ATCGCTCCAC TGCACTCCGG CCTGGGCAAC AAGAGCAAAA
29951 TTCTGTCTGG AAAAAAAAAA AAAAGAAAAA GAAAAGGATT GTGAGGATGA
30001 AAAGAGAGGC GTGAGCTCTC TGTCAGCGTT GGAGTACAAT AGAGAGGATG
30051 AAATGAGCTG TAGGGCGAAC TGCTACATAG TCACAACCAC AATAATATGC
30101 CCACTTATGA GCTCCTACTC AGCAGAGAAC ATCAGCTATG GTCTTTACAT
30151 CTCATTGCAC TAATCGAGTT CTTTCTGTTG CAAGCGACCA AAAACCCAAT
30201 TCAAAGAGGC ATGTGCAAAA AAGGACATTT GTGGCTTATG CAGTTGAAAT
30251 GTCCAATGAG TAGGGCTTCA GGCACAGTTG CATCCAGGCA CTCATAAGAT
30301 GTCATCAGGG TTTTCTTGCT GTCTCTTTGC TCTGATTTGC TCTGAGAATG      (SEQ ID NO:3)
```

```
FEATURES:
Start:    3000
Exon:     3000-3032
Intron:   3033-3493
Exon:     3494-3607
Intron:   3608-5219
Exon:     5220-5443
Intron:   5444-5611
Exon:     5612-5665
Intron:   5666-6130
Exon:     6131-6342
Intron:   6343-15419
Exon:     15420-15562
Intron:   15563-15649
Exon:     15650-15865
Intron:   15866-16855
Exon:     16856-16959
Intron:   16960-17050
Exon:     17051-17135
Intron:   17136-19043
Exon:     19044-19100
Intron:   19101-19208
Exon:     19209-19295
Intron:   19296-19502
Exon:     19503-19535
Intron:   19536-19617
Exon:     19618-19739
Intron:   19740-21452
Exon:     21453-21548
Intron:   21549-21641
Exon:     21642-21710
Intron:   21711-21798
Exon:     21799-21895
Intron:   21896-24152
Exon:     24153-24305
Intron:   24306-24391
Exon:     24392-24506
Intron:   24507-27233
Exon:     27234-27349
Stop:     27350
```

FIGURE 3K

ALLELIC VARIANTS (SNPs):

| DNA Position | Major | Minor | Domain | Protein Position | Major | Minor |
|---|---|---|---|---|---|---|
| 1695 | A | C G | Beyond ORF(5') | | | |
| 4607 | T | C | Intron | | | |
| 5133 | G | C | Intron | | | |
| 6190 | A | C | Exon | 162 | H | P |
| 6196 | T | C | Exon | 164 | V | A |
| 7403 | T | G C | Intron | | | |
| 9981 | C | T | Intron | | | |
| 9998 | - | T | Intron | | | |
| 11050 | T | C | Intron | | | |
| 11772 | T | A G | Intron | | | |
| 12797 | T | - | Intron | | | |
| 12801 | T | - | Intron | | | |
| 12857 | T | C | Intron | | | |
| 17525 | C | T | Intron | | | |
| 17552 | G | A | Intron | | | |
| 17572 | T | G | Intron | | | |
| 18846 | G | A | Intron | | | |
| 18871 | T | C | Intron | | | |
| 18872 | C | A | Intron | | | |
| 19600 | T | C | Intron | | | |
| 21013 | A | G | Intron | | | |
| 22055 | A | G | Intron | | | |
| 22112 | T | C | Intron | | | |
| 22113 | T | C | Intron | | | |
| 22221 | C | T | Intron | | | |
| 22360 | T | C | Intron | | | |
| 22543 | G | A | Intron | | | |
| 23751 | A | T | Intron | | | |
| 23764 | C | T | Intron | | | |
| 23782 | G | A | Intron | | | |
| 24593 | C | T | Intron | | | |
| 24673 | C | T | Intron | | | |
| 24730 | T | C | Intron | | | |
| 24750 | A | G | Intron | | | |
| 24764 | A | G | Intron | | | |
| 24780 | A | T | Intron | | | |
| 24856 | A | G | Intron | | | |
| 26136 | A | G | Intron | | | |
| 26331 | C | G | Intron | | | |
| 28362 | A | G C | Beyond ORF(3') | | | |
| 28745 | T | C | Beyond ORF(3') | | | |

Context:

DNA Position
1695    ATCACTCAAGATCCGTTCCCAGAAATTAATCGAAAGTCACAAGAAGCACCGTCGCTCTCG
        GAGGTCCTAGACTCGTCCTGACACCCACCAGGCGGCCCCTTCGGAGCCCCCGAATCTCCG
        GGTCTAGCGCACGCCACGGGCGCTTCAGGGGCTGAACGCGGCCGGACCGGGAACGGAGGC
        GGCCAGCGGCGCCCGGAGGGGAGGAAGGGGCCGGGCCAGACGTTCCCACAGTAAATCTCC
        CCAGCTGGGTCCGCCCCGGCCTCAGAGTTGCGCAATAAATGTTACCGACCATGCCCCTGG
        [A,C,G]
        TATTCATCTGTTTTTTGACCCTGCACCACCCAAGAGACGGCTGTCCCTGAAAACCCAGGGC
        CACAGACTGCCTCCTCCAACCTGGGTCATGATGACTCCCATCAGCTAGTGACGCAGATGG

FIGURE 3L

```
        AGCTTAAAAATGGGAGATGGCCCGATGTAGTGGTTTTATGCCTGTAATCCCAGTATTTTG
        GGAGGCTGAGTTGGGAGGATCACTTGAGTCCAGGAGCTCCAGGCTGCAGTGAGCTATGAT
        CGTGCTACTGCACTCCAGCCTGGGCCACAGAGCCAGACCCTGTCTCAATAAATAAAATAA

4607    CCCAGCAGTGGTCCCAGCTACTCAGGAGGCTGGGGCAGAGGGACCGCTTGAGTCTAGGAC
        TTGGAGGCTGCAGTGAGCTATGATTGTGCCACTGCACCCCAGCCTGGGCAACAAAACAAG
        ACCTGTTTCTAAAAAAAAACAAACCAAAACAATAACTCCAAGAAGCCGGGAGACAGAGGAA
        TCACATGAAAGAATGGTGCTACAGGCGGGGCGAGGTGGCTCACGCCTGTAATCCCAGCAC
        TTTGGGAGGCCGAGGCAAGTGGATCATCAGGTCAGGAGTTCAAGACCAACCTGGCCAAGA
        [T,C]
        GGTGAAACACCGTCTCTACTAAAAATACGAAAAAACTAGCTGGGCTTGGTGGCGGGTGCC
        TGTAATCCCAGATACTTGGGAGGCTGAGGCAGAGAATTGCTTGAACCCAGGAGGCGGAGG
        TTGCAGTGAGCCAAGATCACGCCACTGAACTCCAGCCTAGGTGACAGAGTGAGATTCTGT
        CTCAAAAAAAAAAAAAAAAAAAGTGGTGCTAGGGGCTGGGCACGGTGGTTCACGCCTGTAA
        TCCTAGCCCTTTGGGAGACTTTGGGAGGCCAAGGGGGGCAGATTACTTGAGGTCAGGAGT

5133    GGTTCACGCCTGTAATCCTAGCCCTTTGGGAGACTTTGGGAGGCCAAGGGGGGCAGATTA
        CTTGAGGTCAGGAGTTCGAGACCAGTCTGACCAACATGGTGAAACCCTATCTCTACAAAA
        ATACAAAAATTAGCTGGGCTTGGTGGTGTGCGCCTGTAGTTTCAGCTACTTGGAGGCTGA
        GGAAGGAGGATTGCTTGAACCCAGGAGGCAGAAGTTGAAGTGACCCAAGATCGTGCCACT
        GCACTCCAGCCTGGGCAACAGAGTGAGACTCTGTCTCAAAAAAAAAAACAAAAAAAAAAA
        [G,C]
        AGTGGTGCTAGTGATGAATGTGACTAGAGAAGGGGTGCTGTGAGGACCACTCCTGCTCTC
        TCATGGCCACCTCTCCCCTCCTGCAGGCTCCCAGCCCCATTGCCAATACCTTCCTCCACT
        ATCGAACCAGCAAGGTGAGGGTGCTGAGGGCAGCGCGCCTGGAGCGGCTGGTGGGAGAGT
        TGGTGTTTGGAGACCGTGAGCAGGACCCCAGCTTCATGCCCGCCTTCCTGGCCACCTACC
        GGACCTTTGTACCCACTGCCTGCCTGCTGGGCTTTCTGCTGCCACCAATGCCACCGCCCC

6190    CTGTCTCTACTAAAAATACAACAACAACAAAAAAAGGTAGCTGGGTGTGGTGGCGCATGC
        CTGTAGTCCCAGCTACTCGGGAGGCTGAGGTTGCAGTGAGTCAAGATCAGGCCATTGCAC
        TGCAGCCTTGGTGACACAGTAAGACTCTATCTCAAAAAAAAAAAAAAAAAAAAAGGTACCA
        GGAGTCATATTCTATGTCCCCCACTCTGGACCCAGCTCTGAGACCCTGCCTCTCTGGCCA
        GGGCTGTGGTGTCAGTGCTGGGCTCCTGGCTGCAGGACCACCCTCAGGATTTCCGAGACC
        [A,C]
        CCCTGTCCATTCGGACCTGGGCAGTGTCCGAACCTTTCTGGGCTGGGCGGCCCCAGGGAG
        TGCTGAGGCTCAAAAAGCAGAGAAGCTTCTGGAAGATTTTTTTGGAGGAGGCTGAGCGAGA
        GCAGGAAGAGGAGCCGCCTCAGGTGTGGACAGGTGAGGGGTTTTCAGATCCAGTCGTGTT
        CTGAGAAGGCCTTTCCTGTCTGCTTCTTCCCACACAGGCTTTCTCTCCCCTCTCAGAGCT
        ACAAAACTTAAGCAAGATTTTAAACTCTAAGCCTCAATTTCTTCATCTTTACAATGGGGA

6196    CTACTAAAAATACAACAACAACAAAAAAAGGTAGCTGGGTGTGGTGGCGCATGCCTGTAG
        TCCCAGCTACTCGGGAGGCTGAGGTTGCAGTGAGTCAAGATCAGGCCATTGCACTGCAGC
        CTTGGTGACACAGTAAGACTCTATCTCAAAAAAAAAAAAAAAAAAAAAGGTACCAGGAGTC
        ATATTCTATGTCCCCCACTCTGGACCCAGCTCTGAGACCCTGCCTCTCTGGCCAGGGCTG
        TGGTGTCAGTGCTGGGCTCCTGGCTGCAGGACCACCCTCAGGATTTCCGAGACCACCCTG
        [T,C]
        CCATTCGGACCTGGGCAGTGTCCGAACCTTTCTGGGCTGGGCGGCCCCAGGGAGTGCTGA
        GGCTCAAAAAGCAGAGAAGCTTCTGGAAGATTTTTTTGGAGGAGGCTGAGCGAGAGCAGGA
        AGAGGAGCCGCCTCAGGTGTGGACAGGTGAGGGGTTTTCAGATCCAGTCGTGTTCTGAGA
        AGGCCTTTCCTGTCTGCTTCTTCCCACACAGGCTTTCTCTCCCCTCTCAGAGCTACAAAA
        CTTAAGCAAGATTTTAAACTCTAAGCCTCAATTTCTTCATCTTTACAATGGGGATAATAA

7403    TTAAATTTAATTTAATTTAATTTTATTTTTTTATCTATTTTTTTTTTTTAGACAGAGTCTC
        GCACTGTTACCCAGGCTGGAGTGCAGTGGCACAATCTTGGCTCACTGCAACCTCCACCTC
        CTGGGCTCAAGCCATTCTCCTGTCTCAGCCTCCTGAGTAGCTGGGACCACAGGCGCATGT
        CACCACGCCCGGCTAATTTTTTTGTAAAGGTGAGGTTGTGCCATGTTGCCCAGGCTGGTC
        TCAAACTCCTGAACTCAAGTGATCTGCCTGCCTTGGCCTCCCAAAATGCTGGGATTACAG
        [T,G,C]
        CATAAGCCATTGTGCATGCGTAGCCTCCTTACTTGATTATTGGCTTTTGCTCATCTCATA
```

FIGURE 3M

```
         GGCTGTGAGTGCATGAGAGGAGGACCTGTTGTTCTTGCTCCCAGCTCTGTCCCCAGGGGC
         AGGAACAACACAGATTAGTTTGCTGAATAATTGCATCCTGCTTAGGAAGTATCATCTTTC
         ACCCATCTGTATTTGATCTGATCCACATCACAAAAGCATCTCTATCCCTAATCCCCATCG
         CTTAATCTCCAGATTATAGAGGCCACCTTCCTGTCCAATTTACAAAGTAGCAGCCACTTC
```

9981
```
         CCTCCTGAGTAGCTAAGACTACACTTGCACCATGTAGTTTAGAAGAAAGTAGATGACCAC
         CATGCTCATCTATTTTATTTTTAACAACTTTATTTTGGGTTCACTTTTTGCTATGGAAAAT
         TTCAGACATATACAAAAGTAGAGAGAATAGTATGAAGAACATTCAGACATCCATCACCTA
         TCATCAACGATGATCAATTTCACAAAAAAATATTTTCAGGATGATTTTAAAACAAATCCC
         GGGCTTATGTCAATTCATACATAAATGTTTTGGGTACACATGTCTGACAACAGGCTTACT
         [C,T]
         TTTTTTTTTTTTTTTTTGAGACGGAGTTTCGCTCTTGTTGCCCAGGCTGGAGTGCAATGG
         CAGGATCTCAGCTCACCTCAACCTCTGCCTCCTGGGTTCAAGTGATTCTCCTGCCTCAGC
         CTCCCGAGTAGCTGGGATTACAGGCGTGCACCACCACACCCGGCTAATTTTCTATTTTTA
         GTAGAGAGGGGGGTTTCTCCATGTTTGTCAGGCTGGTCTCGAACTCCTGACCTCAGGTGA
         TCCGCCCACCTTGGCCTCCCAAAGTGTTGGTATTACAGGCGTGAGCCATGGCGCCCGGCC
```

9998
```
         ACTACACTTGCACCATGTAGTTTAGAAGAAAGTAGATGACCACCATGCTCATCTATTTTA
         TTTTAACAACTTTATTTTGGGTTCACTTTTTGCTATGGAAAATTTCAGACATATACAAAA
         GTAGAGAGAATAGTATGAAGAACATTCAGACATCCATCACCTATCATCAACGATGATCAA
         TTTCACAAAAAAATATTTTCAGGATGATTTTAAAACAAATCCCGGGCTTATGTCAATTCA
         TACATAAATGTTTTGGGTACACATGTCTGACAACAGGCTTACTTTTTTTTTTTTTTTTTT
         [-,T]
         GAGACGGAGTTTCGCTCTTGTTGCCCAGGCTGGAGTGCAATGGCAGGATCTCAGCTCACC
         TCAACCTCTGCCTCCTGGGTTCAAGTGATTCTCCTGCCTCAGCCTCCCGAGTAGCTGGGA
         TTACAGGCGTGCACCACCACACCCGGCTAATTTTCTATTTTTAGTAGAGAGGGGGGTTTC
         TCCATGTTTGTCAGGCTGGTCTCGAACTCCTGACCTCAGGTGATCCGCCCACCTTGGCCT
         CCCAAAGTGTTGGTATTACAGGCGTGAGCCATGGCGCCCGGCCCTTTTATTTTTATTTTT
```

11050
```
         ACTCCTGACCCTCCCACCTCAGCCTCCTGAGTAGCTGGGACCACAGGTGCCCACCATGGC
         ACCCAGCCCTAAATTTTCTTTTTGACAGTTGTTTCTGGCCAGGTGTTGTGGCACATGCCTA
         TAGTCCCAGCTACTTAGGATGCTGAGATGGGAGGATCTCTTGACTCCGGGAAATCAAAAG
         CTGCCGTGAGCTGTGAGCATGCCCCTGCACTCCAGGCGATAGAGCTGGGGGAAGGAGGAA
         TAGTTGTTTCTTCAAATTGAAATCCAAAGATCTACTCAAGGTATTTGGTTGTTTGCTTCT
         [T,C]
         TTTTTTTTTTTTTTTTTTTTTTTGAGATGGAGTCTCACTCTGTTGTCCAGGCTGGAGGGT
         AGTGGCGTGATCTTGGCTCACTGCAACCTCCGCCTCCTGGGTTCAAGCGATTCTCCTGGC
         TCAGCCTCCTGAGTAGCTGAGTTTACAGGTGCCCACCAACACGCCCAGCTAATTTTTGTA
         TTTTTAGTAGTGAGGGGGTTTCACCATGTTGGCCAGGCTGGTCTTGAACTCCTAACCTTT
         AGTGATCTGCCCACATCGGCCTCCCGAAGTGTCGGGATTACAGACATGAGTCACCACGCC
```

11772
```
         CATTTTTTTTTCCAGGGCCCACTTTTTTTTGGGGTGGGGGGAGGAGAGACAGTTTCTTGC
         TCTGTCACCCAGGCTGGAGTGCTATGGCATGATCACAGCTCACTGCAGCCTTGACCTCCT
         GGGCTCAAGAGATCCTCCCTCCTAAGCCTCTTGAGTAGGTGGGACAGCAGGTGTGCATCA
         GGATGCGCAACTTTAAAAATTTTTTTATGTAGACAT
         [T,A,G]
         GGGTCTCACTACGCCGCCCAGGCTGGTCTCAAACTCCTGGTCTCAAGCAATCCTCCTACC
         TCAACCTCCAAAAGTGCTGGGACTATAGGTGTGCCCAGCCCAGTACCCACTTCTAAAAAC
         TAATATTTTGCAATGCCACCTGTCCTAATTCAAGATGAAAGAGGTAATTACACAGATTTA
         CAAAGATTATTTTAAAATAATAGTATTGGGGCAGGG
```

12797
```
         CACAGTAGAGTGTCACGGTGCTGTTGTACTGACAGCAACAAGCACCAACGAACGCACAGG
         AGGGCACTGGTGAGGCAAAGACAGCAACATAGGTTCTGGGGACATCATTTTCCAAACTTG
         TGAACAACATTTGCAATTTGCAAACAAAACAAAGCCCAGACTTTCGTGGTCCTTGCATTC
         TTGGAGCCAAAAAAATTTGTGTTTATGAACAAAATAGTCAGGTTCTAGGTGCATATTATT
         GCAAACATGTTTTTCTTTTCTTTTTGTTTTGTTTGTTTGTTTGTTTTGTTTGTTTTGT
         [T,-]
         TTTTGAGATGGAGTCTCGCTCTGTCGCCCAGGCTGGAGTGCAGTGGCATGATCTCGGCTT
         ACTGCAAGCTCCGCCTCGCCGGTTCACGCCATTCTCCTGCCTCAGCCTCCTGGGTAGCTG
```

FIGURE 3N

```
              GGACTACAGGCGCCCGCCACCACGCCTGGCTAATTTTTTCTATTTTTTAGTAGAGACGGG
              GTTTCACCATGTTAGCCAGGATGGTCTCGATCTCCTGACCTCGTGATCTACCCGCCTTGG
              CCTCCCAAAGTGCTGGGATTACAGGCGTGAGCCACTGCCCCCGGCCTTCTTTTCTTTTCT

12801     GTAGAGTGTCACGGTGCTGTTGTACTGACAGCAACAAGCACCAACGAACGCACAGGAGGG
              CACTGGTGAGGCAAAGACAGCAACATAGGTTCTGGGGACATCATTTTCCAAACTTGTGAA
              CAACATTTGCAATTTGCAAACAAAACAAAGCCCAGACTTTCGTGGTCCTTGCATTCTTGG
              AGCCAAAAAAATTTGTGTTTATGAACAAAATAGTCAGGTTCTAGGTGCATATTATTGCAA
              ACATGTTTTTCTTTTCTTTTTGTTTTTGTTTGTTTGTTTGTTTTGTTTTGTTTTGTTTTT
              [T,-]
              GAGATGGAGTCTCGCTCTGTCGCCCAGGCTGGAGTGCAGTGGCATGATCTCGGCTTACTG
              CAAGCTCCGCCTCGCCGGTTCACGCCATTCTCCTGCCTCAGCCTCCTGGGTAGCTGGGAC
              TACAGGCGCCCGCCACCACGCCTGGCTAATTTTTTCTATTTTTTAGTAGAGACGGGGTTT
              CACCATGTTAGCCAGGATGGTCTCGATCTCCTGACCTCGTGATCTACCCGCCTTGGCCTC
              CCAAAGTGCTGGGATTACAGGCGTGAGCCACTGCCCCCGGCCTTCTTTTCTTTTTCTTTTT

12857     AGGGCACTGGTGAGGCAAAGACAGCAACATAGGTTCTGGGGACATCATTTTCCAAACTTG
              TGAACAACATTTGCAATTTGCAAACAAAACAAAGCCCAGACTTTCGTGGTCCTTGCATTC
              TTGGAGCCAAAAAAATTTGTGTTTATGAACAAAATAGTCAGGTTCTAGGTGCATATTATT
              GCAAACATGTTTTTCTTTTCTTTTTGTTTTTGTTTGTTTGTTTGTTTTGTTTTGTTTTGT
              TTTTTGAGATGGAGTCTCGCTCTGTCGCCCAGGCTGGAGTGCAGTGGCATGATCTCGGCT
              [T,C]
              ACTGCAAGCTCCGCCTCGCCGGTTCACGCCATTCTCCTGCCTCAGCCTCCTGGGTAGCTG
              GGACTACAGGCGCCCGCCACCACGCCTGGCTAATTTTTTCTATTTTTTAGTAGAGACGGG
              GTTTCACCATGTTAGCCAGGATGGTCTCGATCTCCTGACCTCGTGATCTACCCGCCTTGG
              CCTCCCAAAGTGCTGGGATTACAGGCGTGAGCCACTGCCCCCGGCCTTCTTTTCTTTTCT
              TTTTTTTTTTTTTTGAGACAAAGTCTCTGTCACCCAGGCTAGAGTGCCGTGGCGTGGAC

17525     TCAGGACACTCTGTCCTTCCCTACCGCTCAGCAATGACCTTATCCTTGTCCCTGGCGGGT
              TGCACGTTTTTCTTTCCTCTACTTCCTGCGTTATAGTTGACTGTCAGTGACTGCCCTATT
              TATTCACTCAGCAAAACACAAGAAGTCACAAAGAAAAGGTTACTTAAGGCCAGAGTCATA
              GCACAGGGTGGGAACAAAAAAAATGTTCTGAGGACTTTACCTTGATAAGCAAAACTAAAA
              AATGTGTGTCAAAAGTCTGGCTTATTTATAGGCAAGATTTAGATTCTCATTGCAATCAGG
              [C,T]
              GCTGGTTTTTAGAGTGAATCTAGAATGGATCCCTGGGCCTGGAACATTCTCCACCCCTCC
              AGGTTTGCATGCAACTTGCTCACTCACCTCCTTCTGGTCTCTGATTAAATGTCCCTGCCT
              CTGAGAGGCCTTCCCAGCCTCCATCATCCCCAAAACCACACATCTGGTTTTTTGTTGTTG
              TTGTTGTTGTCGTCATCATTTGTTTTTTTGTTTCTTGTTTGTTTGTATTGAGACAGAGT
              CTCGCTCTGTCACCCAGACTGGAGTGCAGTGGCACGATCTTGGCTCACTGCAACCTCCAC

17552     TCAGCAATGACCTTATCCTTGTCCCTGGCGGGTTGCACGTTTTTCTTTCCTCTACTTCCT
              GCGTTATAGTTGACTGTCAGTGACTGCCCTATTTATTCACTCAGCAAAACACAAGAAGTC
              ACAAAGAAAAGGTTACTTAAGGCCAGAGTCATAGCACAGGGTGGGAACAAAAAAAATGTT
              CTGAGGACTTTACCTTGATAAGCAAAACTAAAAAATGTGTGTCAAAAGTCTGGCTTATTT
              ATAGGCAAGATTTAGATTCTCATTGCAATCAGGCGCTGGTTTTTAGAGTGAATCTAGAAT
              [G,A]
              GATCCCTGGGCCTGGAACATTCTCCACCCCTCCAGGTTTGCATGCAACTTGCTCACTCAC
              CTCCTTCTGGTCTCTGATTAAATGTCCCTGCCTCTGAGAGGCCTTCCCAGCCTCCATCAT
              CCCCAAAACCACACATCTGGTTTTTTGTTGTTGTTGTTGTTGTCGTCATCATTTGTTTTT
              TTGTTTCTTTGTTTGTTTGTATTGAGACAGAGTCTCGCTCTGTCACCCAGACTGGAGTGC
              AGTGGCACGATCTTGGCTCACTGCAACCTCCACCTCCCAGGATCAAGCAATTCTCTCTGC

17572     GTCCCTGGCGGGTTGCACGTTTTTCTTTCCTCTACTTCCTGCGTTATAGTTGACTGTCAG
              TGACTGCCCTATTTATTCACTCAGCAAAACACAAGAAGTCACAAAGAAAAGGTTACTTAA
              GGCCAGAGTCATAGCACAGGGTGGGAACAAAAAAAATGTTCTGAGGACTTTACCTTGATA
              AGCAAAACTAAAAAATGTGTGTCAAAAGTCTGGCTTATTTATAGGCAAGATTTAGATTCT
              CATTGCAATCAGGCGCTGGTTTTTAGAGTGAATCTAGAATGGATCCCTGGGCCTGGAACA
              [T,G]
              TCTCCACCCCTCCAGGTTTGCATGCAACTTGCTCACTCACCTCCTTCTGGTCTCTGATTA
```

FIGURE 30

```
          AATGTCCCTGCCTCTGAGAGGCCTTCCCAGCCTCCATCATCCCCAAAACCACACATCTGG
          TTTTTTGTTGTTGTTGTTGTTGTCGTCATCATTTGTTTTTTGTTTCTTTGTTTGTTTGT
          ATTGAGACAGAGTCTCGCTCTGTCACCCAGACTGGAGTGCAGTGGCACGATCTTGGCTCA
          CTGCAACCTCCACCTCCCAGGATCAAGCAATTCTCTCTGCCTCAGCCTCCCATGTAGCTG

18846     CCTGCTGTTTATCTCCTCCCTACCCTCATCCAAGGTGGTCTGGCTTCTAGAGTGGGCCTT
          AACCCCTGGCTTCTTTTTTTTTTTTTTTTTTTTTTTTGAGATGGAGTTTTGGTCTTGTTGC
          CCAAGCTGGAGTGCAATGGTGCGATCTTGGCTCACTCCAACCTCCGCCTCCCGGGTTCAA
          GCGATTCTTCTGCCTCAGCCTCCCGAGTAGCTGGGATTACAGAAATATGCTACCATGCCC
          AGCTAGTTTTTTATATTCTTAGTAGAAACAGAGTTTCACTCTGTTAGCCAGGCTGGTCTC
          [G,A]
          AACTCCTTACCTCATGTGATCCACCAGCCTCGGCCTCCCAAGTGCTGGGATTACAGGCGT
          GAGCCATCGCACCTGGCCTACCACTGACTTTTGATTACTCAAAGCATGAAGGGTATATAT
          GATGGGTCTGCAGGCATCGTTCCTGAGGAATTGTCCAAGGAGACCCCAGACCTGGCTCAG
          TTTTTCTCTTCCCTCAGGAGGAGGCCACTGAGGGATCCCAAGAAGAGGACAACACCCCAG
          GCAGCCTGCCCTCAGTGAGTGATTACAGTTTGGGATGGGGACAAGTGGGACCTTCAGGGA

18871     TCATCCAAGGTGGTCTGGCTTCTAGAGTGGGCCTTAACCCCTGGCTTCTTTTTTTTTTTT
          TTTTTTTTTTTTGAGATGGAGTTTTGGTCTTGTTGCCCAAGCTGGAGTGCAATGGTGCGAT
          CTTGGCTCACTCCAACCTCCGCCTCCCGGGTTCAAGCGATTCTTCTGCCTCAGCCTCCCG
          AGTAGCTGGGATTACAGAAATATGCTACCATGCCCAGCTAGTTTTTTATATTCTTAGTAG
          AAACAGAGTTTCACTCTGTTAGCCAGGCTGGTCTCAAACTCCTTACCTCATGTGATCCAC
          [T,C]
          AGCCTCGGCCTCCCAAGTGCTGGGATTACAGGCGTGAGCCATCGCACCTGGCCTACCACT
          GACTTTTGATTACTCAAAGCATGAAGGGTATATATGATGGGTCTGCAGGCATCGTTCCTG
          AGGAATTGTCCAAGGAGACCCCAGACCTGGCTCAGTTTTTCTCTTCCCTCAGGAGGAGGC
          CACTGAGGGATCCCAAGAAGAGGACAACACCCCAGGCAGCCTGCCCTCAGTGAGTGATTA
          CAGTTTGGGATGGGGACAAGTGGGACCTTCAGGGAGGGTTGTGGATGGTGATGGGGTCAG

18872     CATCCAAGGTGGTCTGGCTTCTAGAGTGGGCCTTAACCCCTGGCTTCTTTTTTTTTTTTT
          TTTTTTTTTTGAGATGGAGTTTTGGTCTTGTTGCCCAAGCTGGAGTGCAATGGTGCGATC
          TTGGCTCACTCCAACCTCCGCCTCCCGGGTTCAAGCGATTCTTCTGCCTCAGCCTCCCGA
          GTAGCTGGGATTACAGAAATATGCTACCATGCCCAGCTAGTTTTTTATATTCTTAGTAGA
          AACAGAGTTTCACTCTGTTAGCCAGGCTGGTCTCAAACTCCTTACCTCATGTGATCCACC
          [C,A]
          GCCTCGGCCTCCCAAGTGCTGGGATTACAGGCGTGAGCCATCGCACCTGGCCTACCACTG
          ACTTTTGATTACTCAAAGCATGAAGGGTATATATGATGGGTCTGCAGGCATCGTTCCTGA
          GGAATTGTCCAAGGAGACCCCAGACCTGGCTCAGTTTTTCTCTTCCCTCAGGAGGAGGCC
          ACTGAGGGATCCCAAGAAGAGGACAACACCCCAGGCAGCCTGCCCTCAGTGAGTGATTAC
          AGTTTGGGATGGGGACAAGTGGGACCTTCAGGGAGGGTTGTGGATGGTGATGGGGTCAGT

19600     GACCCCTGACCCTTGACCCCTGACCCCAGCTCCACTTGCCCCCAGCACAATGGGCCTCCC
          AATATCCACCCTTGATCCTACCTGTACTCCTGACACCACCCCACACTCCCTTACTACAGT
          GGGGCTCCTGACATCCCAGCCCCTGACCTTGACCCTTGACCCTTGACCCTGGGTGCTGCA
          ATTCAGACACACTTTGCCCCCAGGGGGATCTCATTAACTTTGAGAAGAGGAGGAAGGTGA
          GTGGAGGCTACAGTGGGTGTGGTGGTGCCTGAGGGTGGGGGTGGGGCAGGGGTAGGGTCT
          [T,C]
          AGAGGCTCGTCCTCCAGGAGTGGGAGATCCTGGCCCGCATCCAGCAGCTGCAGAGGCGCT
          GTCAGAGCTACACCCTGAGCCCCCACCCGCCCATCCTGGCTGCCCTGCATGCCCAGAACC
          AGCTCACCGAGGAGCAGAGGTGACCACCCTGTAGCCTGTCCCAGCCCCACCCCAGCTGAG
          CCTGGGTCACCAACTGGATTCCACCCACTCCATACACACCTCCAGCTCCTCCCAAGACCC
          CCTCTTGAGCCCTGATCCCCCACTACAAACCTGTGACCTTGCAGTATCTCCAGTCGAATCA

21013     TGAGTAACTGACTCCAACTTTTATGTTTGACTGTCCAGCTTGACTATGACAACTGTGTCC
          TTTCTTTCTATATAACTGTGACCCTAACCATTGACCCCAATGGTGACCTGACCCCAGTCT
          GACCCTGACTTTATTTTATTTTATTTATTTATTTATTTATTTATTTATTTATTTATTTATT
          TTTGAGACAGAGTCTGGCTCTGTTTCCCAGGCTGGAGTGCAGTGGAGTGATCTCGGCTCA
          CTGTAGCCCCCGCCTCCCAGGTTCAAGCAATTCTACTGCCTCAGCCTCCCCGGTAGCCGC
          [A,G]
```

FIGURE 3P

```
        ATTACAGGCGCGAGCTACCACACCTGGCTAATTTTTTTTGTATTTTTAGTAGAGACGGGG
        TTTCACTATATTGGCCAGGCTGGTTTCGAACTCTTGACCCGAAGCAATCCTCTCGCCTCA
        GCCTCCCAAAGTGCTAGGATTACAGGCGTGAGCCACTGCACCCAGTCCTGACCCTGACTT
        TAATCCTGACCCAATTTGATTCCTTAGTGCCACCCTGTGAATCTCTTTGTGACCTCCTGA
        CCAGCCATCCTGTCCCATCTCTGATAAGACCTTGATGCTCAATGACCCTCATTTACCACC

22055   GAGTCAGCACAGCCACCCCACCTCAGCCTCTGCATCTCCCCCAGTGTGTCCCCAGGGTCA
        CCCCCCTCAAGTCCTAGAAGCAGAGATGCTCCTGCTGGCAGTCCCCCGGCCTCTCCAGGG
        CCCCAGGGCCCCAGCACCAAGGTACCAAGACGGCTTGTGTGTGCATGCGGGCCTGCGGGC
        ACCCAGGCTCTGTGTGTGTGCACGTGTGTGTGCATGCACATGTGTACACACAGGATTGTG
        GGGCCAGGAGTGTATACAGGAGGCACACTGAGCGCCCGGGGTATCCATCCAGGGGATTGC
        [A,G]
        TGCATCTGCACGGCCCTGTTTGGGTGATCACTCATAAATCCGACTCGTGCTCAGATTTGG
        ACCTGTGTAACTGCTTGCCCATGGGTCATCTAGGGTGCAATCACATCACACCCCTTTTTA
        TTTGAAACAGGGTCTTCTTGCTCTGTCACCCAGGCTGAAGTGCAGCGGTGCAATCTCAGC
        TCACCGCAACTTCCACCCCTCCCCCAGGCTCAAGCAATCCTTCCACCTCAGCCTCCCAAG
        TAGCTAGGACCACAGGTGTGCACCACCATGCCCTGCTATTTTTTTTATTTAGTAGAGATG

22112   TCACCCCCCTCAAGTCCTAGAAGCAGAGATGCTCCTGCTGGCAGTCCCCCGGCCTCTCCA
        GGGCCCCAGGGCCCCAGCACCAAGGTACCAAGACGGCTTGTGTGTGCATGCGGGCCTGCG
        GGCACCCAGGCTCTGTGTGTGTGCACGTGTGTGTGCATGCACATGTGTACACACAGGATT
        GTGGGGCCAGGAGTGTATACAGGAGGCACACTGAGCGCCCGGGGTATCCATCCAGGGGAT
        TGCATGCATCTGCACGGCCCTGTTTGGGTGATCACTCATAAATCCGACTCGTGCTCAGAT
        [T,C]
        TGGACCTGTGTAACTGCTTGCCCATGGGTCATCTAGGGTGCAATCACATCACACCCCTTT
        TTATTTGAAACAGGGTCTTCTTGCTCTGTCACCCAGGCTGAAGTGCAGCGGTGCAATCTC
        AGCTCACCGCAACTTCCACCCCTCCCCCAGGCTCAAGCAATCCTTCCACCTCAGCCTCCC
        AAGTAGCTAGGACCACAGGTGTGCACCACCATGCCCTGCTATTTTTTTTATTTAGTAGAG
        ATGAGGTTTCGCCATGTTGCCCAGGTGGGTTTCGAACTCCTGAGCTCAAACAATGCACTC

22113   TCCTGCTGGCAGTCCCCCGGCCTCTCCAGGGCCCCAGGGCCCCAGCACCAAGGTACCAAG
        ACGGCTTGTGTGTGCATGCGGGCCTGCGGGCACCCAGGCTCTGTGTGTGTGCACGTGTGT
        GTGCATGCACATGTGTACACACAGGATTGTGGGGCCAGGAGTGTATACAGGAGGCACACT
        GAGCGCCCGGGGTATCCATCCAGGGGATTGCATGCATCTGCACGGCCCTGTTTGGGTGAT
        CACTCATAAATCCGACTCGTGCTCAGATT
        [T,C]
        GGACCTGTGTAACTGCTTGCCCATGGGTCATCTAGGGTGCAATCACATCACACCCCTTTT
        TATTTGAAACAGGGTCTTCTTGCTCTGTCACCCAGGCTGAAGTGCAGCGGTGCAATCTCA
        GCTCACCGCAACTTCCACCCCTCCCCCAGGCTCAAGCAATCCTTCCACCTCAGCCTCCCA
        AGTAGCTAGGACCACAGGTGTGCACCACCATGCCCTGCTATTTTTTTTATTTAGTAGAGA
        TGAGGTTTCGCCATGTTGCCCAGGTGGGT

22221   GCGGGCCTGCGGGCACCCAGGCTCTGTGTGTGTGCACGTGTGTGTGCATGCACATGTGTA
        CACACAGGATTGTGGGGCCAGGAGTGTATACAGGAGGCACACTGAGCGCCCGGGGTATCC
        ATCCAGGGGATTGCATGCATCTGCACGGCCCTGTTTGGGTGATCACTCATAAATCCGACT
        CGTGCTCAGATTTGGACCTGTGTAACTGCTTGCCCATGGGTCATCTAGGGTGCAATCACA
        TCACACCCCTTTTTATTTGAAACAGGGTCTTCTTGCTCTGTCACCCAGGCTGAAGTGCAG
        [C,T]
        GGTGCAATCTCAGCTCACCGCAACTTCCACCCCTCCCCCAGGCTCAAGCAATCCTTCCAC
        CTCAGCCTCCCAAGTAGCTAGGACCACAGGTGTGCACCACCATGCCCTGCTATTTTTTTT
        ATTTAGTAGAGATGAGGTTTCGCCATGTTGCCCAGGTGGGTTTCGAACTCCTGAGCTCAA
        ACAATGCACTCACCTCGGCCTCCCAAAGTGCTGGGATTACAGGTGTGAGCCACCGCACCC
        AGCCTACACTTTTTTGAGGACATGTATGTCCCTAAGAATCTGCATACCATGGCAGACACG

22360   TCTGCACGGCCCTGTTTGGGTGATCACTCATAAATCCGACTCGTGCTCAGATTTGGACCT
        GTGTAACTGCTTGCCCATGGGTCATCTAGGGTGCAATCACATCACACCCCTTTTTATTTG
        AAACAGGGTCTTCTTGCTCTGTCACCCAGGCTGAAGTGCAGCGGTGCAATCTCAGCTCAC
        CGCAACTTCCACCCCTCCCCCAGGCTCAAGCAATCCTTCCACCTCAGCCTCCCAAGTAGC
        TAGGACCACAGGTGTGCACCACCATGCCCTGCTATTTTTTTTATTTAGTAGAGATGAGGT
```

FIGURE 3Q

[T,C]
TCGCCATGTTGCCCAGGTGGGTTTCGAACTCCTGAGCTCAAACAATGCACTCACCTCGGC
CTCCCAAAGTGCTGGGATTACAGGTGTGAGCCACCGCACCCAGCCTACACTTTTTTGAGG
ACATGTATGTCCCTAAGAATCTGCATACCATGGCAGACACGGTGGCTATTGCCTGTGATC
CCGGCACTTTGGGAAGCCAAAGTGGGAGGATTGCTTGAGGCCGGGAGTTCAAGACCAGCC
TGGGCAACATAGTGAGACCCTATTTCTATTAAAAGTCAAAAAAATTAGCTGGGTGTAGTC

22543    AACTTCCACCCCTCCCCCAGGCTCAAGCAATCCTTCCACCTCAGCCTCCCAAGTAGCTAG
GACCACAGGTGTGCACCACCATGCCCTGCTATTTTTTTTATTTAGTAGAGATGAGGTTTC
GCCATGTTGCCCAGGTGGGTTTCGAACTCCTGAGCTCAAACAATGCACTCACCTCGGCCT
CCCAAAGTGCTGGGATTACAGGTGTGAGCCACCGCACCCAGCCTACACTTTTTTGAGGAC
ATGTATGTCCCTAAGAATCTGCATACCATGGCAGACACGGTGGCTATTGCCTGTGATCCC
[G,A]
GCACTTTGGGAAGCCAAAGTGGGAGGATTGCTTGAGGCCGGGAGTTCAAGACCAGCCTGG
GCAACATAGTGAGACCCTATTTCTATTAAAAGTCAAAAAAATTAGCTGGGTGTAGTCCCA
GCTACTCAGCAGGCTGAGGTGGAAGGATCGCTTGAGTTTGAGGCTGCAGTGAGCTACGAT
CATGCCACGGCACTCTAGCCTGCATGATAGAGCGAGATCCTGTTTATGAAGAAAAAGAGA
CTGGGCACGGTGGCTCACGCCTGTAATCCCAGCACTCTGGGAGGCCGAGGTGGGCGGATC

23751    TTCATGAGATCATGTGTGGGGTTGTTCATTGGCATGGGCTGTGGGTGTATAACCGCTGTC
AGCATATGTATGTACACAGGATTTCTTGTGTATGAGCATGGGTTGTGTGTATATGGACAC
TGTTCATGTCTGTTTCTATAACAGGTAACCAAAGTCTGTATATGGTAGGGTGGTGTATAT
GCAGGCTTGTGAATGTACTCCAGTTGCATGTCCCAGGCTCTGCATGTGTAGGGGGTAGTA
GTATGTTTTCTTGAGATTTTATTTTATTTTATTATTTATTTATTTATTTTTGAGATGGAG
[A,T]
CTTGCTCTGTCACGCAGGCTGGAGTGCAGTAGCGTGATCTTGGCTCACTGCAACCTCTGC
CTCTCAAGTTCAAGTGATTCTCCTGCCTCGGCCTCCCAAGTAGCTGGGATTACAGGCATG
CGCCACCAGGCCCTGCTAATTTTTGTATTTTTAGTAGAGACGGAGTTTCACCACGTTGGC
CAGGCTGGTCTTGAACTCCCGACCTCAAGTGATCCGCCCACCTCGGCCTCCCAAAATGCT
GAGATTACAGGCATGAGCCACTGCGCCCAGCCAATGTTTTCTTGAGATTTTAAATGTGGG

23764    GTGTGGGGTTGTTCATTGGCATGGGCTGTGGGTGTATAACCGCTGTCAGCATATGTATGT
ACACAGGATTTCTTGTGTATGAGCATGGGTTGTGTGTATATGGACACTGTTCATGTCTGT
TTCTATAACAGGTAACCAAAGTCTGTATATGGTAGGGTGGTGTATATGCAGGCTTGTGAA
TGTACTCCAGTTGCATGTCCCAGGCTCTGCATGTGTAGGGGGTAGTAGTATGTTTTCTTG
AGATTTTATTTTATTTTATTATTTATTTATTTATTTTTGAGATGGAGTCTTGCTCTGTCA
[C,T]
GCAGGCTGGAGTGCAGTAGCGTGATCTTGGCTCACTGCAACCTCTGCCTCTCAAGTTCAA
GTGATTCTCCTGCCTCGGCCTCCCAAGTAGCTGGGATTACAGGCATGCGCCACCAGGCCC
TGCTAATTTTTGTATTTTTAGTAGAGACGGAGTTTCACCACGTTGGCCAGGCTGGTCTTG
AACTCCCGACCTCAAGTGATCCGCCCACCTCGGCCTCCCAAAATGCTGAGATTACAGGCA
TGAGCCACTGCGCCCAGCCAATGTTTTCTTGAGATTTTAAATGTGGGGCTATTGAATGCA

23782    GCATGGGCTGTGGGTGTATAACCGCTGTCAGCATATGTATGTACACAGGATTTCTTGTGT
ATGAGCATGGGTTGTGTGTATATGGACACTGTTCATGTCTGTTTCTATAACAGGTAACCA
AAGTCTGTATATGGTAGGGTGGTGTATATGCAGGCTTGTGAATGTACTCCAGTTGCATGT
CCCAGGCTCTGCATGTGTAGGGGGTAGTAGTATGTTTTCTTGAGATTTTATTTTATTTTA
TTATTTATTTATTTATTTTTGAGATGGAGTCTTGCTCTGTCACGCAGGCTGGAGTGCAGT
[G,A]
GCGTGATCTTGGCTCACTGCAACCTCTGCCTCTCAAGTTCAAGTGATTCTCCTGCCTCGG
CCTCCCAAGTAGCTGGGATTACAGGCATGCGCCACCAGGCCCTGCTAATTTTTGTATTTT
TAGTAGAGACGGAGTTTCACCACGTTGGCCAGGCTGGTCTTGAACTCCCGACCTCAAGTG
ATCCGCCCACCTCGGCCTCCCAAAATGCTGAGATTACAGGCATGAGCCACTGCGCCCAGC
CAATGTTTTCTTGAGATTTTAAATGTGGGGCTATTGAATGCACCAGTGGTGGCTGGGGTG

24593    TCGAAGCATCTTGGTGAGGGGCTGGGCTGGGGGTCTGCTGGAGGCTGCCCTGCCCTTGGG
GCCGGGGCCCTCACCTCACCTCCCGCCCCTCTCTTCCAGCTGACCAGTCAGGACAAAGCC
CCCAGCGTGGTCCGGCGAGCCTTGCAGAAGCACAATGTGCCCCAGCCCTGGGCCTGTGAC
TATCAGCTCTTTCAAGTCCTTCCTGGGGACCGGGGTGAGCAGGGATGGGTTGGAGCTCAG

FIGURE 3R

```
              GATAGGGGGCAGCGGGGAGGCGAGCAGACTGACCACGCCCAAGGATGGAGCCCAAGGTTA
              [C,T]
              CCGGGTTCACAGGGCTGTGAGGTGCTTCAGGCAGAGAGTAGGGGTAAGATAATCAGTGGA
              GGTAAGAGGACATAAAATACCTGTAACCCAACGATGTAGGGTCATGAGATTGTCTTGGCT
              CAGTGTGAGAGAGAGGTACCAAAGGTCATCTTCCTAAAATTTAAAAGACAATAAGATTGT
              CCAGGGTCCGGCCAGGCGCAGTGGCTCATGTCTGTAATCCCAGCACTTTGGGAGGTCAAG
              CTGGGCGGATCACTTGAGGTCAGGAGTTTGAGACCAGGCTGACCAACGTGGTGAAACCCC

24673     TCCCGCCCCTCTCTTCCAGCTGACCAGTCAGGACAAAGCCCCCAGCGTGGTCCGGCGAGC
              CTTGCAGAAGCACAATGTGCCCCAGCCCTGGGCCTGTGACTATCAGCTCTTTCAAGTCCT
              TCCTGGGGACCGGGGTGAGCAGGGATGGGTTGGAGCTCAGGATAGGGGGCAGCGGGGAGG
              CGAGCAGACTGACCACGCCCAAGGATGGAGCCCAAGGTTACCCGGGTTCACAGGGCTGTG
              AGGTGCTTCAGGCAGAGAGTAGGGGTAAGATAATCAGTGGAGGTAAGAGGACATAAAATA
              [C,T]
              CTGTAACCCAACGATGTAGGGTCATGAGATTGTCTTGGCTCAGTGTGAGAGAGAGGTACC
              AAAGGTCATCTTCCTAAAATTTAAAAGACAATAAGATTGTCCAGGGTCCGGCCAGGCGCA
              GTGGCTCATGTCTGTAATCCCAGCACTTTGGGAGGTCAAGCTGGGCGGATCACTTGAGGT
              CAGGAGTTTGAGACCAGGCTGACCAACGTGGTGAAACCCCGTCTCTACGAAACATACAAA
              AATTAGTCGGGTGTGGTGGCACACTCCTGTAGTCCCAGCTACTCAGGAGGCTGAGGCAGG

24730     AGCCTTGCAGAAGCACAATGTGCCCCAGCCCTGGGCCTGTGACTATCAGCTCTTTCAAGT
              CCTTCCTGGGGACCGGGGTGAGCAGGGATGGGTTGGAGCTCAGGATAGGGGGCAGCGGGG
              AGGCGAGCAGACTGACCACGCCCAAGGATGGAGCCCAAGGTTACCCGGGTTCACAGGGCT
              GTGAGGTGCTTCAGGCAGAGAGTAGGGGTAAGATAATCAGTGGAGGTAAGAGGACATAAA
              ATACCTGTAACCCAACGATGTAGGGTCATGAGATTGTCTTGGCTCAGTGTGAGAGAGAGG
              [T,C]
              ACCAAAGGTCATCTTCCTAAAATTTAAAAGACAATAAGATTGTCCAGGGTCCGGCCAGGC
              GCAGTGGCTCATGTCTGTAATCCCAGCACTTTGGGAGGTCAAGCTGGGCGGATCACTTGA
              GGTCAGGAGTTTGAGACCAGGCTGACCAACGTGGTGAAACCCCGTCTCTACGAAACATAC
              AAAAATTAGTCGGGTGTGGTGGCACACTCCTGTAGTCCCAGCTACTCAGGAGGCTGAGGC
              AGGAGAATAATTGCTTGAATCTGGGAGGCGGAGGTTGCAGTGAGCCGAGATCATACCACT

24750     TGCCCCAGCCCTGGGCCTGTGACTATCAGCTCTTTCAAGTCCTTCCTGGGGACCGGGGTG
              AGCAGGGATGGGTTGGAGCTCAGGATAGGGGGCAGCGGGGAGGCGAGCAGACTGACCACG
              CCCAAGGATGGAGCCCAAGGTTACCCGGGTTCACAGGGCTGTGAGGTGCTTCAGGCAGAG
              AGTAGGGGTAAGATAATCAGTGGAGGTAAGAGGACATAAAATACCTGTAACCCAACGATG
              TAGGGTCATGAGATTGTCTTGGCTCAGTGTGAGAGAGAGGTACCAAAGGTCATCTTCCTA
              [A,G]
              AATTTAAAAGACAATAAGATTGTCCAGGGTCCGGCCAGGCGCAGTGGCTCATGTCTGTAA
              TCCCAGCACTTTGGGAGGTCAAGCTGGGCGGATCACTTGAGGTCAGGAGTTTGAGACCAG
              GCTGACCAACGTGGTGAAACCCCGTCTCTACGAAACATACAAAAATTAGTCGGGTGTGGT
              GGCACACTCCTGTAGTCCCAGCTACTCAGGAGGCTGAGGCAGGAGAATAATTGCTTGAAT
              CTGGGAGGCGGAGGTTGCAGTGAGCCGAGATCATACCACTGCACTTCAGCCTGGGCAGCA

24764     GCCTGTGACTATCAGCTCTTTCAAGTCCTTCCTGGGGACCGGGGTGAGCAGGGATGGGTT
              GGAGCTCAGGATAGGGGGCAGCGGGGAGGCGAGCAGACTGACCACGCCCAAGGATGGAGC
              CCAAGGTTACCCGGGTTCACAGGGCTGTGAGGTGCTTCAGGCAGAGAGTAGGGGTAAGAT
              AATCAGTGGAGGTAAGAGGACATAAAATACCTGTAACCCAACGATGTAGGGTCATGAGAT
              TGTCTTGGCTCAGTGTGAGAGAGAGGTACCAAAGGTCATCTTCCTAAAATTTAAAAGACA
              [A,G]
              TAAGATTGTCCAGGGTCCGGCCAGGCGCAGTGGCTCATGTCTGTAATCCCAGCACTTTGG
              GAGGTCAAGCTGGGCGGATCACTTGAGGTCAGGAGTTTGAGACCAGGCTGACCAACGTGG
              TGAAACCCCGTCTCTACGAAACATACAAAAATTAGTCGGGTGTGGTGGCACACTCCTGTA
              GTCCCAGCTACTCAGGAGGCTGAGGCAGGAGAATAATTGCTTGAATCTGGGAGGCGGAGG
              TTGCAGTGAGCCGAGATCATACCACTGCACTTCAGCCTGGGCAGCAGAGCGAGACTCTGT

24780     TCTTTCAAGTCCTTCCTGGGGACCGGGGTGAGCAGGGATGGGTTGGAGCTCAGGATAGGG
              GGCAGCGGGGAGGCGAGCAGACTGACCACGCCCAAGGATGGAGCCCAAGGTTACCCGGGT
              TCACAGGGCTGTGAGGTGCTTCAGGCAGAGAGTAGGGGTAAGATAATCAGTGGAGGTAAG
```

FIGURE 3S

```
          AGGACATAAAATACCTGTAACCCAACGATGTAGGGTCATGAGATTGTCTTGGCTCAGTGT
          GAGAGAGAGGTACCAAAGGTCATCTTCCTAAAATTTAAAAGACAATAAGATTGTCCAGGG
          [A,T]
          CCGGCCAGGCGCAGTGGCTCATGTCTGTAATCCCAGCACTTTGGGAGGTCAAGCTGGGCG
          GATCACTTGAGGTCAGGAGTTTGAGACCAGGCTGACCAACGTGGTGAAACCCCGTCTCTA
          CGAAACATACAAAAATTAGTCGGGTGTGGTGGCACACTCCTGTAGTCCCAGCTACTCAGG
          AGGCTGAGGCAGGAGAATAATTGCTTGAATCTGGGAGGCGGAGGTTGCAGTGAGCCGAGA
          TCATACCACTGCACTTCAGCCTGGGCAGCAGAGCGAGACTCTGTTTAAAAAAAAAAAAAA

24856     GCAGACTGACCACGCCCAAGGATGGAGCCCAAGGTTACCCGGGTTCACAGGGCTGTGAGG
          TGCTTCAGGCAGAGAGTAGGGGTAAGATAATCAGTGGAGGTAAGAGGACATAAAATACCT
          GTAACCCAACGATGTAGGGTCATGAGATTGTCTTGGCTCAGTGTGAGAGAGAGGTACCAA
          AGGTCATCTTCCTAAAATTTAAAAGACAATAAGATTGTCCAGGGTCCGGCCAGGCGCAGT
          GGCTCATGTCTGTAATCCCAGCACTTTGGGAGGTCAAGCTGGGCGGATCACTTGAGGTCA
          [A,G]
          GAGTTTGAGACCAGGCTGACCAACGTGGTGAAACCCCGTCTCTACGAAACATACAAAAAT
          TAGTCGGGTGTGGTGGCACACTCCTGTAGTCCCAGCTACTCAGGAGGCTGAGGCAGGAGA
          ATAATTGCTTGAATCTGGGAGGCGGAGGTTGCAGTGAGCCGAGATCATACCACTGCACTT
          CAGCCTGGGCAGCAGAGCGAGACTCTGTTTAAAAAAAAAAAAAAAAAAAAAAAGACTGTCCA
          CGGACAAGTGACAGAAGGGAGTGTTTCTGACCTTCAATTTGTAGGATGGGCTGGGCATGG

26136     ATGGTGGCTCACGCCTGTAATCCCAGCACTTTGGGAGGCCGAGGCGGGTGGATCACGAAG
          TCAAGAGATCGAGACCATCCTGGCCAACATGGTGAAGCCTCGTCTCTACTAAAAATACAA
          AAAATTAGCCAGGCATGGTGGCAGGCGCCTATAGTCCCAGCTACTCAGGAGGCTGAGGCA
          GAAGAATCACTTGAACCCAGGAGGTGAAGGTTGCAGTGAGCCAAGATTGCGCCACTGCAC
          TCCAGCCTGGCGACAGAGTGAGACTCCGTCTCAAAAAAAAAAGAAAAAATAGATTGTCTAG
          [A,G]
          GTCGAGTGAGAGAAGGGAGTGTAGAAGTTTGTCTGATCTTAAGTTTGTAGCATCATGAGA
          TTGTTCAGGCTCAACCTGATGGGATGGGAGACTAAAGGGCATCTGGGCTTAGATTTGTGA
          GAACTAAGTTTGTTCACCACTGGGACCCTGAAGTTATCTGAACTTGGGACGGGAGAGAGG
          CAAATGGATAGCCGCGGAAGCATGAGATTGTCCTGTCTGACAGGGAGAAGCAAGGGATTG
          AGCGTATTCACGCTGAAGTACATGGCATGAGGTTGGCTGGATATTAGGAAAGGATGCTTG

26331     CCCAGGAGGTGAAGGTTGCAGTGAGCCAAGATTGCGCCACTGCACTCCAGCCTGGCGACA
          GAGTGAGACTCCGTCTCAAAAAAAAAAGAAAAAATAGATTGTCTAGGGTCGAGTGAGAGAA
          GGGAGTGTAGAAGTTTGTCTGATCTTAAGTTTGTAGCATCATGAGATTGTTCAGGCTCAA
          CCTGATGGGATGGGAGACTAAAGGGCATCTGGGCTTAGATTTGTGAGAACTAAGTTTGTT
          CACCACTGGGACCCTGAAGTTATCTGAACTTGGGACGGGAGAGAGGCAAATGGATAGCCG
          [C,G]
          GGAAGCATGAGATTGTCCTGTCTGACAGGGAGAAGCAAGGGATTGAGCGTATTCACGCTG
          AAGTACATGGCATGAGGTTGGCTGGATATTAGGAAAGGATGCTTGTGGTTGTTCAGGTGT
          TGAGTGTGAGGCCACAAGCTCGTGCAGGCTGGAAGTGGGAAGTTATTCAAGTTCATGGTG
          ACAGCAGCATGGGATTGGCTGGGAGTGGTTGTGGGGAGGGGTAGGGTGAGCAGGAAGTT
          GTTTGGCGGGGGGTGGTCTAGGGTGGTCTAAGTTTGCCCAAACTTTTACTGCAGGTTGTC

28362     CTGAGGCAGGAGAATTGCTTGAACCCGGAAGGTGGAGGTTGCAGTGAGTGGAAATCACAC
          CACTGTACTCCAGCCTGGGTGACAGAGCAAGACCCTATCTCAAAAACAAACAAACAAACA
          AATGAACAAACAAAAAATTTTCTGAGTGTGGTGATATGAGACTGTAATCCTACCTACTTG
          GGAGGCTGAGCTGGGAGAATCACCAGAGCCCTGGGAGGTTGAAGCTGCAGTGAGCAGTGA
          CTGGGCCCCTGCACTCCAACCTGGAGGACAGAGGGAGATCCTGTCTCAAAAACAAAAAAA
          [A,G,C]
          TAAGAGCCCTAAGAAAGGTGTTGAGTCGGGTATGACACTCAACCCAGATGCCAGAGAGGA
          TCCTGTCTGGCCGGACACAGTGGCTCAGGAGGGTAATCCCAGTACTTTGGGAGGCTGAGG
          TAAGAGGATTGCTTAAGTTCAGGAGTCCGAGAGCAGCCTGGGCAATACAGTGAGATCACA
          TCTCACTAAATAAATAAATAAAGGATCCTATCACACAAAGAGGGTTTAGGACTTCCTTCC
          CCAACATTTTTGGGGTGATATGCCTCTTTTCTACTGTATATATGGGAGAGTGACTAACTG

28745     GCTCAGGAGGGTAATCCCAGTACTTTGGGAGGCTGAGGTAAGAGGATTGCTTAAGTTCAG
          GAGTCCGAGAGCAGCCTGGGCAATACAGTGAGATCACATCTCACTAAATAAATAAATAAA
```

FIGURE 3T

```
GGATCCTATCACACAAAGAGGGTTTAGGACTTCCTTCCCCAACATTTTTGGGGTGATATG
CCTCTTTTCTACTGTATATATGGGAGAGTGACTAACTGAAATTCCATCAGAATTAGAAAC
AAATAGCATCATTACCCATGAGTCAATAAGGGCTGTGAGGATGGGCCCTTTCACTTGCCC
[T,C]
CACCTTCTTCCTCTTCCTGTCACAGATAACCCATCTGTGCAAAGAAGAGAAAAAGAGGTT
GGGTGTGGTGGCTCACATCTGTAATCCCAGCACTTTGGGAGGCTAAGGTGGAAGGATTTT
GAGCCCAGGAGTTTGAGACCAGCCTGGGCAACATAGTGAGACCCCATTTCTACAAAAAAA
TACAAAGATTGGCCAGGCGCGGTGGCTCACGCCTGTAATCCCAGCACTTGGGAGGCTGAG
GCAGGCGGATCATGAGGTCAGGAGATCGAGACCATCCTGGCTAGGTGAAACCCCGTCTCT
```

FIGURE 3U

US 6,773,904 B2

ISOLATED HUMAN RAS-LIKE PROTEINS, NUCLEIC ACID MOLECULES ENCODING THESE HUMAN RAS-LIKE PROTEINS, AND USES THEREOF

This application claims the benefit of U.S. provisional patent application No. 60/282,460, filed Apr. 10, 2001.

FIELD OF THE INVENTION

The present invention is in the field of Ras-like proteins that are related to the RalGEF-like proteins subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the RalGEF-like proteins subfamilies, are a major target for drug action and development. Accordingly, it is valuable to the field of pharmaceutical development to identify and characterize previously unknown members of this subfamily of Ras-like proteins. The present invention advances the state of the art by providing a previously unidentified human Ras-like proteins that have homology to members of the RalGEF-like proteins subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal-transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF), insulin, an interleukin (IL), granulocyte colony-stimulating factor (G-CSF), granulocyte/macrophage colony-stimulating factor (GM-CSF).

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) that regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-Like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal-transducing proteins are members of the Ras superfamily.

The Ras superfamily is a class of low molecular weight (LMW) GTP-binding proteins that consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization that is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK. The lysine residue is essential in interacting with the beta.- and gamma.-phosphates of GTP. Motif II, III, and IV contain highly conserved sequences of DTAGQ, NKXD, and EXSAX, respectively. Specifically, Motif II regulates the binding of gamma-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with $Ca^{2+}$-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX motif that binds a prenyl group and either a palmitoylation site or a basic amino acid-rich region, suggesting their role in membrane-associated functions. In particular, RhoD is a protein that functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10: 1793–1798). Rin and Rit are characterized as membrane-binding, Ras-like proteins without the lipid-binding CAAX motif and carboxy terminal cysteine (Lee, C. -H. J. et al. (1996) J. Neurosci. 16: 6784–6794). Further, Rin is shown to localize in neurons and have calcium-dependant calmodulin-binding activity.

RalGEF-Like Proteins

The novel human protein, and encoding gene, provided by the present invention is related to the family of RalGEF-like proteins (also referred to as RalGDS-like proteins) and shows the highest degree of similarity to RalGEF-like protein 3 (RGL3).

RGL3 shares 35% sequence identity with other known RalGEFs (Ral guanine nucleotide exchange factors). RGL3 is an exchange factor for Ral (a small GTPase) and acts as a downstream effector for both Ras and Rit, which is important in that most known Ras effector proteins do not interact with Rit whereas RGL3 is able to interact with both Ras and Rit. RGL3 exhibits guanine nucleotide exchange activity towards Ral that is stimulated in vivo by both Rit and Ras. RGL3 interacts in a GTP- and effector loop-dependent manner with Rit and Ras via a C-terminal 99 amino acid domain. Rit is a small GTPase closely related to Ras that, when constitutively active, can stimulate oncogenic transformation (Shao et al., *J. Biol. Chem.* 275 (35), 26914–26924 (2000)).

Due to their importance in regulating Rit, which can stimulate oncogenic transformation, novel human RalGEF-like proteins/genes, such as provided by the present invention, are valuable as potential targets for the development of therapeutics to treat cancer. Furthermore, SNPs in RalGEF genes, such as provided by the present invention, may serve as valuable markers for the diagnosis, prognosis, prevention, and/or treatment of cancer.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

The discovery of new human Ras-like proteins and the polynucleotides that encode them satisfies a need in the art by providing new compositions that are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the RalGEF-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample.

DESCRIPTION OF THE FIGURE SHEETS

FIGS. 1A–1B provides the nucleotide sequence of a cDNA molecule or transcript sequence that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample.

FIGS. 2A–2E provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIGS. 3A–3U provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 41 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the RalGEF-like proteins subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the RalGEF-like proteins subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the RalGEF-like proteins subfamily and the expression pattern observed. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known RalGEF-like proteins family or subfamily of Ras-like proteins.

Specific Embodiments

Peptide Molecules

The present invention provides nucleic acid sequences that encode protein molecules that have been identified as being members of the Ras-like protein family and are related to the RalGEF-like proteins subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG.

2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-termiinus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. SNPs were identified at 41 different nucleotide positions, including non-synonymous coding SNPs at positions 6190 and 6196 (protein positions 162 and 164). Changes in the amino acid sequence caused by these SNPs are indicated in FIG. 3 and can readily be determined using the universal genetic code and the protein sequence provided in FIG. 2 as a reference. Some of the SNPs that are located outside the ORF and in introns may affect gene transcription.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypepticle, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis. A large percentage of pharmaceutical agents are being developed that modulate the activity of Ras-like proteins, particularly members of the RalGEF-like proteins subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in bocio tumors, head/neck tissue, breast, parathyroid tumors, uterus papillary carcinomas, colon tumors, and a pooled melanocyte/ fetal heart/pregnant uterus sample. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the RalGEF-like proteins subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis.

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, RalGEF-like proteins or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising RalGEF-like proteins may be administered to a subject to prevent or treat a disorder associated with increased apoptosis including, but not limited to, those listed above.

In still another embodiment, an agonist which is specific for RalGEF-like proteins may be administered to prevent or treat a disorder associated with increased apoptosis including, but not limited to, those listed above.

In a further embodiment, a vector capable of expressing RalGEF-like proteins, or a fragment or a derivative thereof, may be used to prevent or treat a disorder associated with increased apoptosis including, but not limited to, those listed above.

In cancer, where RalGEF-like proteins promotes cell proliferation, it is desirable to decrease its activity. Therefore, in one embodiment, an antagonist of RalGEF-like proteins may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for RalGEF-like proteins may be used directly as an antagonist, or indirectly as a targeting or delivery mechanism for bringing a pharmaceutical agent to cells or tissue which express RalGEF-like proteins.

In another embodiment, a vector expressing the complement of the polynucleotide encoding RalGEF-like proteins may be administered to a subject to prevent or treat a cancer including, but not limited to, the types of cancer listed above.

In inflammation, where RalGEF-like proteins promotes cell proliferation, it is desirable to decrease its activity. Therefore, in one embodiment, an antagonist of RalGEF-like proteins may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for RalGEF-like proteins may be used directly as an antagonist, or indirectly as a targeting or delivery mechanism for bringing a pharmaceutical agent to cells or tissue which express RalGEF-like proteins.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sept 10(9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., Cell 72:223–232 (1993); Madura et al., J. Biol. Chem. 268:12046–12054 (1993); Bartel et al., Biotechniques 14:920–924 (1993); Iwabuchi et al., Oncogene 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding RNA) in a cell, tissue, or organism. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, p-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in bocio tumors, head/neck tissue, breast, parathyroid tumors, uterus papillary carcinomas, colon tumors, and a pooled melanocytelfetal heart/pregnant uterus sample. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in bocio tumors, head/neck tissue, breast, parathyroid tumors, uterus papillary carcinomas, colon tumors, and a pooled melanocytelfetal heart/pregnant uterus sample. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of RNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence.

FIG. 3 provides information on SNPs that have been found in the gene encoding the Ras-like protein of the present invention. SNPs were identified at 41 different nucleotide positions, including non-synonymous coding SNPs at positions 6190 and 6196 (protein positions 162 and 164). Changes in the amino acid sequence caused by these SNPs are indicated in FIG. 3 and can readily be determined using the universal genetic code and the protein sequence provided in FIG. 2 as a reference. Some of the SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2× SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 41 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of RNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis.

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as RNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein RNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of RNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in bocio tumors, head/neck tissue, breast, parathyroid tumors, uterus papillary carcinomas, colon tumors, and a pooled melanocyte/fetal heart/pregnant uterus sample.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as RNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. SNPs were identified at 41 different nucleotide positions, including non-synonymous coding SNPs at positions 6190 and 6196 (protein positions 162 and 164). Changes in the amino acid sequence caused by these SNPs are indicated in FIG. 3 and can readily be determined using the universal genetic code and the protein sequence provided in FIG. 2 as a reference. Some of the SNPs that are located outside the ORF and in introns may affect gene transcription. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. SNPs were identified at 41 different nucleotide positions, including non-synonymous coding SNPs at positions 6190 and 6196 (protein positions 162 and 164). Changes in the amino acid sequence caused by these SNPs are indicated in FIG. 3 and can readily be determined using the universal genetic code and the protein sequence provided in FIG. 2 as a reference. Some of the SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of RNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the RNA that attenuate the ability of the RNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that Ras-like proteins of the present invention are expressed in bocio tumors, head/neck tissue, breast, parathyroid tumors, uterus papillary carcinomas, colon tumors, and a pooled melanocyte/fetal heart/pregnant uterus sample, as indicated by virtual northern blot analysis. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The RNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. SNPs were identified at 41 different nucleotide positions, including non-synonymous coding SNPs at positions 6190 and 6196 (protein positions 162 and 164). Changes in the amino acid sequence caused by these SNPs are indicated in FIG. 3 and can readily be determined using the universal genetic code and the protein sequence provided in FIG. 2 as a reference. Some of the SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing RNA transcription. These include, but are not limited to, the left promoter from bacteriophage λ, the lac, TRP, and TAC promoters from *E coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., Gene 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., Gene 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39(1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:

(a) a nucleotide sequence that encodes a polypeptide having an amino acid sequence comprising SEQ ID NO:2;

(b) a nucleotide sequence consisting of SEQ ID NO:1;

(c) a nucleotide sequence consisting of SEQ ID NO:3; and (d) a nucleotide sequence that is complementary to a nucleotide sequence of (a)–(c).

2. A vector comprising the nucleic acid molecule of claim 1.

3. The vector of claim 2, wherein said vector is selected from the group consisting of a plasmid, a virus, and a bacteriophage.

4. The vector of claim 2, wherein said isolated nucleic acid molecule is inserted into said vector in proper orientation and correct reading frame such that a polypeptide comprising SEQ ID NO:2 is expressed by a cell transformed with said vector.

5. The vector of claim 4, wherein said isolated nucleic acid molecule is operatively linked to a promoter sequence.

6. A host cell containing the vector of claim 2.

7. A process for producing a polypeptide comprising culturing the host cell of claim 6 under conditions sufficient for the production of said polypeptide, and recovering said polypeptide.

8. An isolated polynucleotide consisting of SEQ ID NO:1.

9. An isolated polynucleotide consisting of SEQ ID NO:3.

* * * * *

SEQUENCE LISTING

<160> NUMBER OF SEQ ID NOS: 5

<210> SEQ ID NO 1
<211> LENGTH: 2133
<212> TYPE: DNA
<213> ORGANISM: Homo sapiens

<400> SEQUENCE: 1

```
atggagcgca cagcaggcaa agagctggcc ctggcaccgc tgcaggactg gggtgaagag      60
accgaggacg gcgcggtgta cagtgtctcc ctgcggcggc agcgcagtca gcgcaggagc     120
ccggcggagg gccccggggg cagccaggct cccagcccca ttgccaatac cttcctccac     180
tatcgaacca gcaaggtgag ggtgctgagg gcagcgcgcc tggagcggct ggtgggagag     240
ttggtgtttg gagaccgtga gcaggacccc agcttcatgc ccgccttcct ggccacctac     300
cggacctttg tacccactgc ctgcctgctg ggctttctgc tgccaccaat gccaccgccc     360
ccacctcccg gggtagagat caagaagaca gcggtacaag atctgagctt caacaagaac     420
ctgagggctg tggtgtcagt gctgggctcc tggctgcagg accaccctca ggatttccga     480
gaccaccctg tccattcgga cctgggcagt gtccgaacct ttctgggctg gcggccccca     540
gggagtgctg aggctcaaaa agcagagaag cttctggaag attttttgga ggaggctgag     600
cgagagcagg aagaggagcc gcctcaggtg tggacaggac ctcccagagt tgcccaaact     660
tctgacccag actcttcaga ggcctgcgcg gaggaagagg aagggctcat gcctcaaggt     720
ccccagctcc tggacttcag cgtggacgag gtggccgagc agctgaccct catagacttg     780
gagctcttct ccaaggtgag gctctacgag tgcttgggct ccgtgtggtc gcagagggac     840
cggccggggg ctgcaggcgc ctcccccact gtgcgcgcca ccgtggccca gttcaacacc     900
gtgaccggct gtgtgctggg ttccgtgctc ggagcaccgg gcttggccgc cccgcagagg     960
```

-continued

```
gcgcagcggc tggagaagtg gatccgcatc gcccagcgct gccgagaact gcggaacttc    1020
tcctccttgc gcgccatcct gtccgccctg caatctaacc ccatctaccg gctcaagcgc    1080
agctgggggg cagtgagccg ggaaccgcta tctactttca ggaaactttc gcagattttc    1140
tccgatgaga acaaccacct cagcagcaga gagattcttt ccaggagga ggccactgag     1200
ggatcccaag aagaggacaa caccccaggc agcctgccct caaaaccacc cccaggccct    1260
gtcccctacc ttggcacctt ccttacggac ctggttatgc tggacacagc cctgccggat    1320
atgttggagg gggatctcat taactttgag aagaggagga aggagtggga gatcctggcc    1380
cgcatccagc agctgcagag gcgctgtcag agctacaccc tgagccccca cccgcccatc    1440
ctggctgccc tgcatgccca gaaccagctc accgaggagc agagctaccg gctctcccgg    1500
gtcattgagc accagctgc ctcctgcccc agctccccac gcatccgacg gcggatcagc     1560
ctcaccaagc gtctcagtgc gaagcttgcc cgagagaaaa gctcatcacc tagtgggagt    1620
cccgggacc cctcatcccc cacctccagt gtgtccccag ggtcaccccc ctcaagtcct     1680
agaagcagag atgctcctgc tggcagtccc ccggcctctc cagggcccca gggcccagc     1740
accaagctgc ccctgagcct ggacctgccc agccccggc ccttcgcttt gcctctgggc     1800
agccctcgaa tccccctccc ggcgcagcag agctcggagg cccgtgtcat ccgcgtcagc    1860
atcgacaatg accacgggaa cctgtatcga agcatcttgc tgaccagtca ggacaaagcc    1920
cccagcgtgg tccggcgagc cttgcagaag cacaatgtgc cccagccctg ggcctgtgac    1980
tatcagctct ttcaagtcct tcctggggac cgggtgctcc tgattcctga caatgccaac    2040
gtcttctatg ccatgagtcc agtcgccccc agagacttca tgctgcggcg gaaagagggg    2100
acccggaaca ctctgtctgt ctccccaagc tga                                 2133
```

<210> SEQ ID NO 2
<211> LENGTH: 710
<212> TYPE: PRT
<213> ORGANISM: Homo sapiens

<400> SEQUENCE: 2

```
Met Glu Arg Thr Ala Gly Lys Glu Leu Ala Leu Ala Pro Leu Gln Asp
 1               5                  10                  15

Trp Gly Glu Thr Glu Asp Gly Ala Val Tyr Ser Val Ser Leu Arg
            20                  25                  30

Arg Gln Arg Ser Gln Arg Arg Ser Pro Ala Glu Gly Pro Gly Gly Ser
        35                  40                  45

Gln Ala Pro Ser Pro Ile Ala Asn Thr Phe Leu His Tyr Arg Thr Ser
    50                  55                  60

Lys Val Arg Val Leu Arg Ala Ala Arg Leu Glu Arg Leu Val Gly Glu
65                  70                  75                  80

Leu Val Phe Gly Asp Arg Glu Gln Asp Pro Ser Phe Met Pro Ala Phe
                85                  90                  95

Leu Ala Thr Tyr Arg Thr Phe Val Pro Thr Ala Cys Leu Leu Gly Phe
            100                 105                 110

Leu Leu Pro Pro Met Pro Pro Pro Pro Gly Val Glu Ile Lys
        115                 120                 125

Lys Thr Ala Val Gln Asp Leu Ser Phe Asn Lys Asn Leu Arg Ala Val
    130                 135                 140

Val Ser Val Leu Gly Ser Trp Leu Gln Asp His Pro Gln Asp Phe Arg
145                 150                 155                 160

Asp His Pro Val His Ser Asp Leu Gly Ser Val Arg Thr Phe Leu Gly
```

-continued

```
                165                 170                 175
Trp Ala Ala Pro Gly Ser Ala Glu Ala Gln Lys Ala Glu Lys Leu Leu
            180                 185                 190
Glu Asp Phe Leu Glu Glu Ala Glu Arg Glu Gln Glu Glu Glu Pro Pro
            195                 200                 205
Gln Val Trp Thr Gly Pro Pro Arg Val Ala Gln Thr Ser Asp Pro Asp
            210                 215                 220
Ser Ser Glu Ala Cys Ala Glu Glu Glu Gly Leu Met Pro Gln Gly
225                 230                 235                 240
Pro Gln Leu Leu Asp Phe Ser Val Asp Glu Val Ala Glu Gln Leu Thr
                245                 250                 255
Leu Ile Asp Leu Glu Leu Phe Ser Lys Val Arg Leu Tyr Glu Cys Leu
            260                 265                 270
Gly Ser Val Trp Ser Gln Arg Asp Arg Pro Gly Ala Ala Gly Ala Ser
            275                 280                 285
Pro Thr Val Arg Ala Thr Val Ala Gln Phe Asn Thr Val Thr Gly Cys
            290                 295                 300
Val Leu Gly Ser Val Leu Gly Ala Pro Gly Leu Ala Ala Pro Gln Arg
305                 310                 315                 320
Ala Gln Arg Leu Glu Lys Trp Ile Arg Ile Ala Gln Arg Cys Arg Glu
                325                 330                 335
Leu Arg Asn Phe Ser Ser Leu Arg Ala Ile Leu Ser Ala Leu Gln Ser
            340                 345                 350
Asn Pro Ile Tyr Arg Leu Lys Arg Ser Trp Gly Ala Val Ser Arg Glu
            355                 360                 365
Pro Leu Ser Thr Phe Arg Lys Leu Ser Gln Ile Phe Ser Asp Glu Asn
            370                 375                 380
Asn His Leu Ser Ser Arg Glu Ile Leu Phe Gln Glu Glu Ala Thr Glu
385                 390                 395                 400
Gly Ser Gln Glu Glu Asp Asn Thr Pro Gly Ser Leu Pro Ser Lys Pro
                405                 410                 415
Pro Pro Gly Pro Val Pro Tyr Leu Gly Thr Phe Leu Thr Asp Leu Val
            420                 425                 430
Met Leu Asp Thr Ala Leu Pro Asp Met Leu Glu Gly Asp Leu Ile Asn
            435                 440                 445
Phe Glu Lys Arg Arg Lys Glu Trp Glu Ile Leu Ala Arg Ile Gln Gln
            450                 455                 460
Leu Gln Arg Arg Cys Gln Ser Tyr Thr Leu Ser Pro His Pro Pro Ile
465                 470                 475                 480
Leu Ala Ala Leu His Ala Gln Asn Gln Leu Thr Glu Glu Gln Ser Tyr
                485                 490                 495
Arg Leu Ser Arg Val Ile Glu Pro Ala Ala Ser Cys Pro Ser Ser
            500                 505                 510
Pro Arg Ile Arg Arg Ile Ser Leu Thr Lys Arg Leu Ser Ala Lys
            515                 520                 525
Leu Ala Arg Glu Lys Ser Ser Ser Pro Ser Gly Ser Pro Gly Asp Pro
            530                 535                 540
Ser Ser Pro Thr Ser Ser Val Ser Pro Gly Ser Pro Ser Ser Pro
545                 550                 555                 560
Arg Ser Arg Asp Ala Pro Ala Gly Ser Pro Pro Ala Ser Pro Gly Pro
                565                 570                 575
Gln Gly Pro Ser Thr Lys Leu Pro Leu Ser Leu Asp Leu Pro Ser Pro
            580                 585                 590
```

-continued

```
Arg Pro Phe Ala Leu Pro Leu Gly Ser Pro Arg Ile Pro Leu Pro Ala
            595                 600                 605
Gln Gln Ser Ser Glu Ala Arg Val Ile Arg Val Ser Ile Asp Asn Asp
        610                 615                 620
His Gly Asn Leu Tyr Arg Ser Ile Leu Leu Thr Ser Gln Asp Lys Ala
625                 630                 635                 640
Pro Ser Val Val Arg Arg Ala Leu Gln Lys His Asn Val Pro Gln Pro
                645                 650                 655
Trp Ala Cys Asp Tyr Gln Leu Phe Gln Val Leu Pro Gly Asp Arg Val
            660                 665                 670
Leu Leu Ile Pro Asp Asn Ala Asn Val Phe Tyr Ala Met Ser Pro Val
        675                 680                 685
Ala Pro Arg Asp Phe Met Leu Arg Arg Lys Glu Gly Thr Arg Asn Thr
    690                 695                 700
Leu Ser Val Ser Pro Ser
705                 710

<210> SEQ ID NO 3
<211> LENGTH: 30350
<212> TYPE: DNA
<213> ORGANISM: Homo sapiens

<400> SEQUENCE: 3
gtccccgccc cacctccctg gggaagctct cactccccaa ggaagcccaa gacgtcagag      60
accctgtccc gtctcaagct ccgcctccaa gggaaagaag tcccaccctg tccccgaaaa     120
gctcggagac ctatctgcag ttctggagca gcccgagaca aagacctat cctgcccgca     180
gcagagggca atttcttcag gaggccatcc acaatggcc tccctcgaat ccttactgtt     240
cccaagaggc ctccccgaaa cctttacata tagagttaga gttcagaggc tcccccatca     300
cagacgtggc cttgacctaa gtccccgccc ccaatggcta ggatcgaccc tgcaggtggg     360
cccttacctc ctaggccccg ccccgaaag aaaagccccg ccctgggtg gagccttcca       420
agaggcccca cccctctcgg ctgacccggc tctaccctgg ccgcaggagg acggccgctt    480
cgcgggaaag gagctggatc cccaggcaga taactatgtg ccaaacctgc tgggcctcgt    540
ggaggaaaag ctgctgaaac tgcaggcgca gctccaggc cacgacgtgc aggagatgct    600
gtgccacatc gctaaccgcg aggtgccctg cagccatggg gcagagctcc agagatctag    660
gagtagggct gggtcggaaa accagggaac cggggggcaac ttcgggagac cagattgcag   720
gctgatcagc caggaagggg tctcggggac aacgggcgag gtttgacgag ccagggggtga  780
gcccgagcca cgagggaaga aaccagaaga ggtgcaggcg gtcctgtga ggctagagga    840
cgcggctggg gtatccggat ggggagaggc ctagtggcag ggccccagag accaggggcg    900
gacctgagtg atgaggggt gaagctgggt atcaaggtgc ctgcttaagg agggatggga    960
gtgggcagtg gtctccagtt ggaactaggg catatctcgg aatgggtag ggaggagggg  1020
gaacgtgact tctcggtggc ccctggcccc gcccaccttc ctctctcgct tcccatcccc   1080
gcttagttcc tcgccagctt agagggaagg ctgcccgaat acaacacccg catcgccctg  1140
ccccttgcca cttccaagga caagttttt ggtcagtatg ggtgggggga tgaagggtg    1200
cggttgggc cccaagctgg gtagcaggag gttgtcagat accctgttca gggccaaggt   1260
ggggtggag tgggtggta aagggaaggg gagccaggga tggggacctg gatcccacat    1320
cgctccctgc tcatccccc acccccctta gacgaagaga gtgaggagga ggacaacgag   1380
```

```
gtagtgaccc gcgcatcact caagatccgt tcccagaaat taatcgaaag tcacaagaag    1440
caccgtcgct ctcggaggtc ctagactcgt cctgacaccc accaggcggc cccttcggag    1500
cccccgaatc tccgggtcta gcgcacgcca cgggcgcttc aggggctgaa cgcggccgga    1560
ccgggaacgg aggcggccag cggcgcccgg aggggaggaa ggggccgggc cagacgttcc    1620
cacagtaaat ctccccagct gggtccgccc cggcctcaga gttgcgcaat aaatgttacc    1680
gaccatgccc ctgggtattc atctgttttt gaccctgcac cacccaagag acggctgtcc    1740
ctgaaaaccc agggcacag actgcctcct ccaacctggg tcatgatgac tcccatcagc    1800
tagtgacgca gatggagctt aaaaatggga gatggcccga tgtagtggtt ttatgcctgt    1860
aatcccagta ttttgggagg ctgagttggg aggatcactt gagtccagga gctccaggct    1920
gcagtgagct atgatcgtgc tactgcactc cagcctgggc cacagagcca gaccctgtct    1980
caataaataa aataagggcg gggtgcagtg gctcattcat acctatattc ccagcacttt    2040
gggaggctga gctgggtgtg tcgcttgagc ccagggggttc cagactagcc tgggcaacat    2100
ggtgaaaacc agtttttacc aaaaaaaaa aaaaaaaaa aagctgagca tggtggcata    2160
tgcctgtagt cccagctact tgggagactg aggcaggaga atggattgaa cccaggaggc    2220
ggagattgca gtgagccaag atcaagccac tgcactgcag ccttggcaac aggagtgaga    2280
ccctgtctct aaaaataat aaggctgggc gccgtggttc atgcctgtaa tcccagcatt    2340
ttgggaggct gaggtgggcg aatctcttga ggccaggagt ttgagaccag cctggcaagt    2400
atggcaaaac cccgcctcta caaaaatac aaaaattagc tgagcatggt ggcggcacct    2460
gtaatcctag ctacttggga ggctgaggca caagaatcct ttgaatctgg gaggcggagg    2520
ttgcagtgag ttaagatcaa gccactgtac tccagcatgg gtgacagaac gagactccat    2580
ctcaaaataa tagcaataat aataaaaagt ggaagatgcc cccacacttg atcaagctag    2640
ccccttccac tggaggacag aggactctgg tctggggaca cacacatgcc cccacacagg    2700
agctccccca catctgggga tacaaaaaag accccttggg gacagatatg tcctttcttc    2760
tggggacaga ttgataggca cccagcggaa gagccaggac ctctcctggg ctggcgctgg    2820
gtccggctgg aggcacccag aggctgggtc cggcctgccc tgccccgccc cgccccagca    2880
gctcggccgc tccgcccctc tggcctcagc gcccggccac tgcccgccgc cgccacccg    2940 ccacccgccg gcccttccgc tcactcagc ggcgccactg agagggacgg gcgccggcca    3000
tggagcgcac agcaggcaaa gagctggccc tggtaagggg acaagggatc cccgaccccc    3060
gcatccctgg tgacccgcag gtccagaaac tccaagcgcc cgcccgtcgg acggtatctg    3120
ctcccaatct gaacttgccc tggagtcccc tcctggggac tcgcggccct tgacccagtg    3180
aagcgactgg ttcctcttag ggatgggggc gcgagtctct gagcgcagtc ggcagaaaga    3240
gctagagaca ggttctatta gactgggccc tgggacatcc ccaaatgcca ccccatgtcc    3300
tcaggacctg ggaggagggg acccgcagcg aggagggac tagcctggga ccccagccct    3360
agtctcgcag cttctggccg ggaaggggcg tggggatgca gcaggaggac tcggcccgag    3420
tccgagcggc caaggaggct gaggcccag gacctgtgcc cctttggtgc cctgagtccg    3480
cctgtgcgtc caggcaccgc tgcaggactg gggtgaagag accgaggacg gcgcggtgta    3540
cagtgtctcc ctgcggcggc agcgcagtca gcgcaggagc ccggcggagg gccccgggg    3600 cagccaggtg aggagggggt ttggtgggtg gcgcggggcc ggaagcgacc agttgagggc    3660
ggagctggag agccgagcac aggccgccag gtgcagtggg cggaaggaag ggagggggctc    3720 ggaggcgacc agatgaggcg accaggtaga aaggggactg ggggcggcca ggtaagtggg    3780
```

-continued

```
gggagatcca gggaatgggg tggggccagg cgatggccgc gcagttcccg agaggagcct      3840
agggacaact tggtaaggac agaactggac ggcagagttg ggaaaggcag gtttagaggg      3900
ccggggctgg aaggtggaat ggggttggtt tagcaagtgg ctaggtgagg gcggatgggg      3960
cagccagtga agcgcgacag gagggctgag ggaagccctg ggtggaaaag agtgtgtggg      4020 gcggggggcgg ggggtgggg ggaggggacg ggaggggggag gggacgggag agggagtagg     4080
ggacagggca tgggagaggg agggtttcca gggcaagttg caggagctat ttgtggatgg      4140
ggaggaacaa taacttcaag cgggcaggga gtggggcaca cacctataat ccctgcgctt      4200
cgagagacca aggcagaagg ccaggaattg agaccagcc tggacaacac agcaagattc       4260
tctctaataa aaataaaaat taaaaaacta gctgtgcgtg atgatgccca gcagtggtcc      4320
cagctactca ggaggctggg gcagagggac cgcttgagtc taggacttgg aggctgcagt     4380
gagctatgat tgtgccactg caccccagcc tgggcaacaa acaagacct gtttctaaaa       4440 aaaacaaacc aaaacaataa ctccaagaag ccgggagaca gaggaatcac atgaaagaat     4500
ggtgctacag gcggggcgag gtggctcacg cctgtaatcc cagcactttg ggaggccgag     4560
gcaagtggat catcaggtca ggagttcaag accaacctgg ccaagacggt gaaacaccgt     4620
ctctactaaa aatacgaaaa aactagctgg gcttggtggc gggtgcctgt aatcccagat     4680
acttgggagg ctgaggcaga gaattgcttg aacccaggag gcggaggttg cagtgagcca    4740
agatcacgcc actgaactcc agcctaggtg acagagtgag attctgtctc aaaaaaaaaa     4800
aaaaaaaagt ggtgctaggg gctgggcacg gtggttcacg cctgtaatcc tagccctttg    4860
ggagactttg ggaggccaag gggggcagat tacttgaggt caggagttcg agaccagtct    4920
gaccaacatg gtgaaaccct atctctacaa aaatacaaaa attagctggg cttggtggtg     4980
tgcgcctgta gtttcagcta cttggaggct gaggaaggag gattgcttga acccaggagg    5040
cagaagttga agtgacccaa gatcgtgcca ctgcactcca gcctgggcaa cagagtgaga     5100
ctctgtctca aaaaaaaaaa caaaaaaaaa aagagtggtg ctagtgatga atgtgactag    5160
agaaggggtg ctgtgaggac cactcctgct ctctcatggc cacctctccc ctcctgcagg     5220
ctcccagccc cattgccaat accttcctcc actatcgaac cagcaaggtg agggtgctga    5280
gggcagcgcg cctggagcgg ctggtgggag agttggtgtt tggagaccgt gagcaggacc    5340
ccagcttcat gcccgccttc ctggccacct accggacctt tgtacccact gcctgcctgc    5400
tgggcttcct gctgccacca atgccaccgc ccccacctcc cgggtcagta gcgaaccata    5460
acctccgtat tctccaccct agaaccccaa ctgggcaccc ccctccacct cctcaggtgt     5520
ggaacctgga aacacctccc agacccagag ccctcttcct aagcccctc taggttcccc     5580 cttcttcacc tgctgggggg cctcttccca gggtagagat caagaagaca gcggtacaag     5640
atctgagctt caacaagaac ctgaggtggg tccttcatcc agatagggga gtgcggggag     5700
ggaaatccaa gaggtcaaag gttagcagtc ggactggggt tttgaaaatt gcaggttggg    5760
taataagaga ctgggagtca ggtggggcgt ggtggctcat gcctgtaatc ccaacacttt    5820
gggaggccga ggcaggtgga tcactggagg tcaggagtta gagaccatcc tggccaatat    5880
ggcgaaaccc tgtctctact aaaaatacaa caacaacaaa aaaggtagc tgggtgtggt     5940 ggcgcatgcc tgtagtccca gctactcggg aggctgaggt tgcagtgagt caagatcagg    6000
ccattgcact gcagccttgg tgacacagta agactctatc tcaaaaaaaa aaaaaaaaa     6060 aaggtaccag gagtcatatt ctatgtcccc cactctggac ccagctctga gaccctgcct    6120
```

```
ctctggccag ggctgtggtg tcagtgctgg gctcctggct gcaggaccac cctcaggatt    6180
tccgagacca ccctgtccat tcggacctgg gcagtgtccg aacctttctg ggctgggcgg    6240
ccccagggag tgctgaggct caaaaagcag agaagcttct ggaagatttt ttggaggagg    6300
ctgagcgaga gcaggaagag gagccgcctc aggtgtggac aggtgagggg ttttcagatc    6360
cagtcgtgtt ctgagaaggc ctttcctgtc tgcttcttcc cacacaggct ttctctcccc    6420
tctcagagct acaaaactta agcaagattt taaactctaa gcctcaattt cttcatcttt    6480
acaatgggga taataattct ttgtcagccg ggcgtggtgg ctcacgcctg tatcccagca    6540
gtttgggagg ccaaggatgg tgtatcacct gaggtcagga gtttgagacc agtctgacaa    6600
acatggagaa accccatccc tactaaaaat acaaaattag ccgggcgtgg tgggcatgt     6660 ctataatccc agctattcgg gaggctgagg caggagaatc gtttgaaccc gggaggcgga    6720
ggttgcggtg agtcgagatc gtgccattgc actctcgcct ggacaaccag agcgaaactc    6780
cgtctaaaaa aaaaaacaaa ttctttgtct gaagtattag catgtgtcta atacttttcc    6840
ctccttggtg ccgttgggtc aggatgctct gtgtttctag ctacaaacca ttgccttgat    6900
acttgtcttt attttctttt ttttgagtca gggtcttgct ccgttgctca ggctggagtg    6960
cagtgtctcc atcatggctc agtgcaggct caacatcctg gactcaggtg atcctcccgc    7020
ctgggtctcc aaaactgctg gcattacagg cgcgagccac tatcctagc ctgtaaaatt     7080 tttcttattt ttgaatttct ttttaaattt aatttaattt aattttattt ttttatctat    7140
tttttttttt agacagagtc tcgcactgtt acccaggctg gagtgcagtg gcacaatctt    7200
ggctcactgc aacctccacc tcctgggctc aagccattct cctgtctcag cctcctgagt    7260
agctgggacc acaggcgcat gtcaccacgc ccggctaatt ttttgtaaa ggtgaggttg      7320 tgccatgttg cccaggctgg tctcaaactc ctgaactcaa gtgatctgcc tgccttggcc    7380
tcccaaaatg ctgggattac agccataagc cattgtgcat gcgtagcctc cttacttgat    7440
tattggcttt tgctcatctc ataggctgtg agtgcatgag aggaggacct gttgttcttg    7500
ctcccagctc tgtccccagg ggcaggaaca acacagatta gtttgctgaa taattgcatc    7560
ctgcttagga agtatcatct ttcacccatc tgtatttgat ctgatccaca tcacaaaagc    7620
atctctatcc ctaatcccca tcgcttaatc tccagattat agaggccacc ttcctgtcca    7680
atttacaaag tagcagccac ttctctatcc ctggtgacaa agtctcagtt atttatatat    7740
atataaaggt atatatatat atatatatat atatatatat atacatga aggtgtatat      7800 atatatatat atatgaaggt atatatatat atgtatatat atgaaggtat atatataa      7860 aggtatatat ataaaggt atatatctaa aggtatatat atatataaag gtatatataa      7920
gggtatatat ataaaaggt atatatatat atatgaaggt atatatatat atgtatatat     7980
atgaaggtat atatataa aggtatatat ataaaaggt atatatataa aggtatatat      8040
atatataaag gtatatatat ataaaggtat atatatatat aaaggtatat atatataggt    8100
gtatatatat atatatatat atatatatat atatatatat atatgatttc tccagctgat    8160
tccaagtcat tagagctcca tagttcactg tggtatccac tagcacctgt cgctatttaa    8220
attaattaaa attggctggg cgcggcggct catgcctata atcccagcac tttgggaggc    8280 cgacggggc ggatcccaag gttcggagat cgagaccatc ctggctaaca tggtgaaacc     8340
ccgtctctac taaaaataca aaaaatatt agccgggcgt ggtggcgagc gcctgtagtc     8400
ccagctactc gggaggctga ggcaggagaa tggcgcgaac ctgggaggcg gagcttgcag    8460
tgagctgaga tcaagccact gaactccaac ctgggtgaca cagcgagact ctgcctaaaa    8520
```

-continued

```
aaaaaaaacc aaaaaacaaa attataataa taattaatta attaattaaa attaaataaa    8580
attcaggtct tttcttttta gagatggggt cttgccatgt tgcccaggct ggtctcgaac    8640
tcctgggctt aagcaatcct ccagcatcaa cctctcagag tgctgggatt gtaagtgtga    8700
gctactgtgc ctgaccctgc cttttttttt tttttttttt ttttgagacg gagcctcgct    8760
ctgtcaccca ggctggagtg cagtggcgcc atctcggcac actgcaacct cctcctccca    8820
ggttcaaaag attctcctgc cttagcctcc caagtagctg ggattatagg cacctgccac    8880
cacacccagc taattttgta ttttattag agacagcgtt tcactatgtt ggtcagtctg     8940
gtcttgaact cctgacctca ggtgatccac ccacctcggt ctcccaaagt gctgggatta    9000
caggcgtgag ctaccatgcc tggcccgctt tttttttttt tttttttctt tttcaaaatc    9060
cagtcaagca aaggcaaaaa ttcaggtctt caatcccact acccacattt tgagtgctca    9120
gccaccacac tggacatagc agatagataa ttttccacc attgcagaga attatatgga     9180
aagtgctgcc ctagtttctt tgaggtcaga ggagaaaatt aacatttgtt taagaccttc    9240
tatgtgctag gccctgggac acactttatt tcattttatt ttattttatt tattttact    9300
tttattttat tttgagacag agtctcgctc tgtcgcctag gctggagtgc aatggcgcga    9360
tcttggctta ctgcaacctc cacctcctgg gttcaagtga ttctcctgcc tcagcctcct    9420
gagtagctgg tactacaggc gcccgccacc aggcccagct aatttttgt agttttagta     9480
gagacgggt ttcaccgtgc tagccaagat ggtctcgatc tcctgatctc gtgatccgct     9540
tgcctcggtc tcccaaagtg ctgggattac aggcgtgagc caccgcaccc gactatgaat    9600
tttatttta gatacagggt cttgctctgt tgcccaggct ggactcgaac tcctgggctc     9660
aagtgagcct cctacctcag cctcctgagt agctaagact acacttgcac catgtagttt    9720
agaagaaagt agatgaccac catgctcatc tattttattt taacaacttt attttgggtt    9780
cacttttgc tatggaaaat ttcagacata tacaaaagta gagagaatag tatgaagaac     9840
attcagacat ccatcaccta tcatcaacga tgatcaattt cacaaaaaaa tattttcagg    9900
atgattttaa aacaaatccc gggcttatgt caattcatac ataaatgttt tgggtacaca    9960
tgtctgacaa caggcttact tttttttttt ttttttttga gacggagttt cgctcttgtt   10020
gcccaggctg gagtgcaatg gcaggatctc agctcacctc aacctctgcc tcctgggttc   10080
aagtgattct cctgcctcag cctcccgagt agctgggatt acaggcgtgc accaccacac   10140
ccggctaatt ttctattttt agtagagagg ggggtttctc catgtttgtc aggctggtct   10200
cgaactcctg acctcaggtg atccgcccac cttggcctcc caaagtgttg gtattacagg   10260
cgtgagccat ggcgcccggc cctttatttt ttattttta ataaccttca tgttcatact    10320
taaaaaaaa tcagaaatat ttgatataaa aaaaatccaa tccaggccag atgcagaggc    10380
tcctgctggc gatcccagca ttttgggagg ccaaggcagg tggatgggct ttgagcccag   10440
gagattgaga ctagcctggg caacatgttg aaactttgtg tctacaaata attagctggg   10500
catggtggtg actgcctata gtcccagctg cttgggaggc tgaggcaaga ggatcatttt   10560
agcctgggat ggtcaaggct gcagtgagcc gtgattatgc cactgtactc cagcctaggt   10620
gacagagcga gaccctgcct caaaaacaga aaaataccc agtctatatt caaatattca     10680
aatccctgt tgtgcctga acctttttt ggacactggg ttttcctatt tgcctgggc       10740
tgggcttgaa ctcctgaccc tcccacctca gcctcctgag tagctgggac acaggtgcc    10800
caccatggca cccagcccta aattttcttt tgacagttgt ttctggccag gtgttgtggc   10860
```

| | |
|---|---|
| acatgcctat agtcccagct acttaggatg ctgagatggg aggatctctt gactccggga | 10920 |
| aatcaaaagc tgccgtgagc tgtgagcatg cccctgcact ccaggcgata gagctggggg | 10980 |
| aaggaggaat agttgtttct tcaaattgaa atccaaagat ctactcaagg tatttggttg | 11040 |
| tttgcttctc tttttttttt tttttttttt tttgagatgg agtctcactc tgttgtccag | 11100 |
| gctggagggt agtggcgtga tcttggctca ctgcaacctc cgcctcctgg gttcaagcga | 11160 |
| ttctcctggc tcagcctcct gagtagctga gtttacaggt gcccaccaac acgcccagct | 11220 |
| aattttttgta ttttttagtag tgaggggggtt tcaccatgtt ggccaggctg gtcttgaact | 11280 |
| cctaaccttt agtgatctgc ccacatcggc ctcccgaagt gtcgggatta cagacatgag | 11340 |
| tcaccacgcc ctaccggtcg tttgttcata agtctctttt attctgtaac agatcccct | 11400 |
| tgcctcttgt ttgaagccat tagagggcaa aaaaaatggg tcattttttcc tgaggtatgt | 11460 |
| ctcacattct tttcgactta cctcatggtt tcatgcagca tgtttctcta tccccataat | 11520 |
| tgctgtaaga tttaaaggtt tgattagatg tagggcattt tttttttccag ggcccacttt | 11580 |
| tttttgggt gggggaggga gagacagttt cttgctctgt cacccaggct ggagtgctat | 11640 |
| ggcatgatca cagctcactg cagccttgac ctcctgggct caagagatcc tccctcctaa | 11700 |
| gcctcttgag taggtgggac agcaggtgtg catcaggatg cgcaaccttta aaattttttt | 11760 |
| tatgtagaca tggggtctca ctacgccgcc caggctggtc tcaaactcct ggtctcaagc | 11820 |
| aatcctccta cctcaacctc caaaagtgct gggactatag gtgtgcccag cccagtaccc | 11880 |
| acttctaaaa actaatatttt tgcaatgcca cctgtcctaa ttcaagatga aagaggtaat | 11940 |
| tacacagatt tacaaagatt attttaaaat aatagtattg gggcagggtg ctatggctca | 12000 |
| tgcctgtaat cccagcacgt tgggaagccg aggcaggagg atcacctgag gtcaggagtt | 12060 |
| cgagaccagt ccggccaaca tggtgaaacc ccatctctac taaaaaaaat aaaaaataaa | 12120 |
| ataaaataaa ataaaaaata aataaataat aaaaaaatat atatatattt aaattagctg | 12180 |
| gctgggcata gtggcacctc ctgtagtccc agttgctcag gaggctgagg caggagaatt | 12240 |
| gcttgaaccc tggaggcaga ggttgcagtg agccgagatc gagccactgc actccagcct | 12300 |
| gggcgacaga gcaagactcc atcacaaaat aaaaaaataa aataaaataa tagtatgatg | 12360 |
| ccataactag tacaaaggag aaggaaagtg agagtaactt acacagcaat aaaccatgtt | 12420 |
| ttcaatgggt aatgcttggg tatgccccac taggacacat gatgaggttg tcccgtgtct | 12480 |
| ttgcctgtcc tagcgtcaca gtagagtgtc acggtgctgt tgtactgaca gcaacaagca | 12540 |
| ccaacgaacg cacaggaggg cactggtgag gcaaagacag caacataggt tctggggaca | 12600 |
| tcatttttcca aacttgtgaa caacatttgc aatttgcaaa caaaacaaag cccagacttt | 12660 |
| cgtggtcctt gcattcttgg agccaaaaaa atttgtgttt atgaacaaaa tagtcaggtt | 12720 |
| ctaggtgcat attattgcaa acatgttttt cttttcttttt tgttttttgtt tgtttgtttg | 12780 |
| ttttgttttg ttttgttttt tgagatggag tctcgctctg tcgcccaggc tggagtgcag | 12840 |
| tggcatgatc tcggcttact gcaagctccg cctcgccggt tcacgccatt ctcctgcctc | 12900 |
| agcctcctgg gtagctggga ctacaggcgc ccgccaccac gcctggctaa ttttttctat | 12960 |
| tttttagtag agacggggtt tcaccatgtt agccaggatg gtctcgatct cctgacctcg | 13020 |
| tgatctaccc gccttggcct cccaaagtgc tgggattaca ggcgtgagcc actgcccccg | 13080 |
| gccttctttt cttttcttttt ttttttttttt ttgagacaaa gtctctgtca cccaggctag | 13140 |
| agtgccgtgg cgtggacctg gctcactgca acctccacct tctaggttga ggtgattctc | 13200 |
| tagccttagc ctcccgagct gggattacag gcacttgcca ccatgctcag ctgattttttg | 13260 |

```
tattttttagt agagacaggg tttcgccatg ttggcccgac tggtctcgaa ctccttgacct    13320 caagtgattc gcctgccttg gcctcccaaa gtgctgggat tacatgtgtg agccactgtg    13380
ccagacccct tcttcctttc ttaaagacaa gtcaagtgca gtagtgagaa gggggggaaag    13440 agtagaacaa ggagttcgat ctgtaactgt gaacaatcaa ttgagataag tcactacctt    13500
gggaccagcc acaaacaggt ttttcaaaga cacaaatgtc tggagataca tttggaggct    13560
agagggcaca attcaggatc ccagtttcca aagtttcccc tccagggtgc caccatcaaa    13620
atccactaaa gtaaaattat tcatatttgt tcagcacttt atagcagtct ggtagcatga    13680
tctttttttt tttttttgag atggagtctc gctctgtcgc caggctggag tgcagtgaca    13740
cgatgtcggc tcactgcaag ctccgtctcc agggttcaag cgattctcct gcctcagccc    13800
cccgagtagc tgggattaca ggcgcgtgcc atcacgcccg gctaattttt gtattttttt    13860
ttagtagaga cggggtttca ccgtgttggc cacgctggtc tcgaactcct gacctcaggt    13920
gatccacccg cctcggcctc ccaaagtgct gggattacag gcgtgagcca gcgcccgg    13980 cagcatgatc ttaaacgaaa acaaaaacga atccacagc caggcgcact ggctcacacc    14040
cgcaatccca aaactttggg aagccaagag ggaggatcgc ttgagcccag gtgtttgaga    14100
ccagcctggc aacataatga gaccctgtct ctacaaaaaa taaaaaatta gctgggcatg    14160
gtggtgtgtg cctatagtcc cagcaactca ggaggctgag gcaggaggat cactggagcc    14220
caaaaggttg aggctgcagt gaactgtgat cacaccactg tactccagcc tgggtgacca    14280
agggagagcc tgtttcaaaa agaaggcaca gcttacccct gcaatcccag cacttttggga    14340 agtcgaggca ggcagatccc ttgaggtcag gagttcaaga ccagcctggc cgacatggtg    14400
aaaccctgtc tctacaaaaa tacaaaagtt agctgggcgt ggtggctcag tgcctgtaat    14460
cccagctact tgggagactg aggcaggaga attggttgaa acctggaggc ggaggttgca    14520
gtgagccaag atcacgccat tgcattccag cctgggcgac agagtcagac tccgtcttaa    14580
aaaaaaaaaa aaaaaggcac agagaggtta aaatacatgc tctacacagc aagctagtgg    14640
acgagtttgc atctgagttt gagactttct gacaatagcc ttccctgaac caggaagtcg    14700
tatcacctct ttccaaaaaa aagaggtcag attaatctta tcctaataca tgttaaaaat    14760
cataaagctc tattttcttc tctggccttt gagtacccgg cttcaaaccc ctgccctgcc    14820
atttaccaaa ggtgtgacaa attgttcttt gcctcccttt ccttaattgt aaaaggtgga    14880
taaataatag tacctcccct actggactca cagtaactca gtggtgagtt actgagtaaa    14940
tccacactag ctgcttagtg aacattactg ttgctgttac atccttaaaa acactcaggg    15000
ccaggcgtgg tggctcacac ctgtaatgcc agcactttgg gaggccaagg cgggcagatc    15060
acttgaggtc aggagtttga ccagcctgg ccaacatgg tgaaagcccg tctctattaa    15120
aaatacaaaa attagccggg catggtggca catgcctgta atcccagcta ctcagaaggc    15180
tgaggcagga gaatcacttg aacccaggag gcggaggttg tggtcagctg agattgcgcc    15240
attgtactcc agcttgggca acagagtaag actgtctcaa aaaaaaaaa aaatttaaga    15300 gagctctccg ttttacaaat gaggaaagtg agcctcagag agggacaggg actcacccaa    15360
ggtcacacag ccagtcttgg attcaaactt gagagtttgt aacccttttct aatgatcagg    15420 acctcccaga gttgcccaaa cttctgaccc agactcttca gaggcctgcg cggaggaaga    15480
ggaagggctc atgcctcaag gtccccagct cctggacttc agcgtggacg aggtggccga    15540
gcagctgacc ctcatagact tggtgaggat cccggacagg gtcgggatga gccacagtga    15600
```

```
ggggacaggt tctgctaagc accaatccca caccccteec ctggcccagg agctcttctc   15660
caaggtgagg ctctacgagt gcttgggctc cgtgtggtcg cagagggacc ggccgggggc   15720
tgcaggcgcc tcccccactg tgcgcgccac cgtggcccag ttcaacaccg tgaccggctg   15780
tgtgctgggt tccgtgctcg gagcaccggg cttggccgcc ccgcagaggg cgcagcggct   15840
ggagaagtgg atccgcatcg cccaggtgtg ttgcgggcgc ggagagggga tgcggggggcg   15900 ggccctgggg caagggaaa aaatgagggc tccggagaga gatagggggcg agtctaggcg   15960 agggagggaa cggggtggaa agttgatacc tagggtgaga cttgggttca gggaggaggg   16020
tctgggtcct gcagagaggc cgcgggcacg actaggtccc aagggagctg ggagaagtag   16080
ggagcccgga ccggagaagt caaggtcgga ggcaggggct ggaggggcag ctggggaggg   16140
gctggagccc gagggaggag ggaggaaggg aatcctaggg aataagtggg agtcttggta   16200
gcttgtcgga tgtgagacaa cacccagggg tccgacctgg cgtcacaagt cacgggatca   16260
ggctgggcga agtgactcac gcctgtaatc ccagcacttt ggggagaggg aggatcgctt   16320
gagcccttga gtttgagacc agcctaggca acatagtgag accaatgttt ctagaaaaaa   16380 aaaaaaatt aaaaaaatta aaatgagac ttacaaaaaa attagccggg tgtggtggtg   16440
tgcccctgta attcccagct acttgggagg ctgaggcagg ataatcactt gaacccggga   16500
ggcggaggtt gcagtgactc gagatcgggc cactgcattc cagcctgggg gataaagcga   16560
gactctgtcc aaataattaa taataataat aataataagc catgcatgat ggcgcgcgcc   16620
tgtagtccca gctactgagg caggaggctg aggcatgtgg atcgcttaag cccaggaatt   16680
ccaggcagca agtgagctat gatcgagccc ctgcactcca gcctgggcca cagaccctat   16740
ttttcaaaaa aaaaaaaaaa aaaaaaaaaa aaaaaaaaa aaaaaaagat gaagaagttt   16800
caggatgaaa ggtggataat gcctgggtct gacctgcgtc cccaccgcct ggcagcgctg   16860
ccgagaactg cggaacttct cctccttgcg cgccatcctg tccgccctgc aatctaaccc   16920
catctaccgg ctcaagcgca gctgggggc agtgagccgg tgagctgggg cgggacctgt   16980 tcccagccc atcccaggtc tgaccctccc aagccactga cccctgacca cccttctcct   17040
gtccttccag ggaaccgcta tctactttca ggaaactttc gcagattttc tccgatgaga   17100
acaaccacct cagcagcaga gagattcttt tccaggtaga gatggatgca gactccaggg   17160
attttaggcc cgggaagtcg gggagggggac ttggggccag gcagggtaa tctccctgct   17220 atagtcagga cactctgtcc ttccctaccg ctcagcaatg accttatcct tgtccctggc   17280
gggttgcacg tttttctttc ctctacttcc tgcgttatag ttgactgtca gtgactgccc   17340
tatttattca ctcagcaaaa cacaagaagt cacaaagaaa aggttactta aggccagagt   17400
catagcacag ggtgggaaca aaaaaaatgt tctgaggact ttaccttgat aagcaaaact   17460
aaaaaatgtg tgtcaaaagt ctggcttatt tataggcaag atttagattc tcattgcaat   17520
caggcgctgg tttttagagt gaatctagaa tggatccctg ggcctggaac attctccacc   17580
cctccaggtt tgcatgcaac ttgctcactc acctccttct ggtctctgat taaatgtccc   17640
tgcctctgag aggccttccc agcctccatc atccccaaaa ccacacatct ggttttttgt   17700
tgttgttgtt gttgtcgtca tcatttgttt ttttgtttct ttgtttgttt gtattgagac   17760
agagtctcgc tctgtcaccc agactggagt gcagtggcac gatcttggct cactgcaacc   17820
tccacctccc aggatcaagc aattctctct gcctcagcct cccatgtagc tgggattaca   17880
ggcacccacc acgacgcttg gctaattttt gtatttggta gagacggggt tttgccgtgt   17940
tggccaggct ggtctcgaat ccctgacctg aggtgatcca cctgccttgg cttcccaaag   18000
```

-continued

```
tgctgggatt acaggcgtga gccatcactc ccagccaaat tcacctggc taacagagtg    18060
aaaccctgtt ttcctgccca gcacctagaa cagcacgtga gctgggctca gtgactcacg    18120
cctataatcc caacactttg ggaggccaag gtgagaggat cacttgagcc caggagttca    18180
agaccaacct gggcaacatg gcaaaacccc atctctgcaa aaatacaac aattagctgg    18240
gcgtttgtgg tgcacgtctg tagtcccagc tattcaggag gctgaggagg gaggatcgct    18300
tgaacttggg cggtcaagcc ttcagtgagc caagatcagg ccactgcact ccagcctgag    18360
tgacaaagtg agactccatc tcaaaataaa atgaaataaa agtaagtaa acaacagcaa    18420
attcaggata cccaggagat ccctggcagg cctgtgccat ccagctgcgg acaaggattc    18480
tctccttgtt aaggccagcc ctgggggcca ctacccacaa gccccacctc tcatggggcc    18540
tgctccctgc tgtttatctc ctccctaccc tcatccaagg tggtctggct tctagagtgg    18600
gccttaaccc ctggcttctt ttttttttt ttttttttt tgagatggag ttttggtctt    18660
gttgcccaag ctggagtgca atggtgcgat cttggctcac tccaacctcc gcctcccggg    18720
ttcaagcgat tcttctgcct cagcctcccg agtagctggg attacagaaa tatgctacca    18780
tgcccagcta gttttttata ttcttagtag aaacagagtt tcactctgtt agccaggctg    18840
gtctcaaact ccttacctca tgtgatccac cagcctcggc ctcccaagtg ctggattac    18900
aggcgtgagc catcgcacct ggcctaccac tgacttttga ttactcaaag catgaagggt    18960
atatatgatg ggtctgcagg catcgttcct gaggaattgt ccaaggagac cccagacctg    19020
gctcagtttt tctcttccct caggaggagg ccactgaggg atcccaagaa gaggacaaca    19080
ccccaggcag cctgccctca gtgagtgatt acagtttggg atggggacaa gtgggacctt    19140
caggagggt tgtggatggt gatggggtca gtaatggccc caagtgactg gagctttggg    19200
ggctgcagaa accacccca ggccctgtcc cctaccttgg caccttcctt acggacctgg    19260
ttatgctgga cacagccctg ccggatatgt tggaggtctg accctgacc cttgaccct    19320
gaccccagct ccacttgccc ccagcacaat gggcctccca atatccaccc ttgatcctac    19380
ctgtactcct gacaccaccc cacactccct tactacagtg gggctcctga catcccagcc    19440
cctgaccttg acccttgacc cttgaccctg ggtgctgcaa ttcagacaca ctttgccccc    19500
aggggatct cattaacttt gagaagagga ggaaggtgag tggaggctac agtgggtgtg    19560
gtggtgcctg agggtggggg tggggcaggg gtagggtctt agaggctcgt cctccaggag    19620
tgggagatcc tggcccgcat ccagcagctg cagaggcgct gtcagagcta caccctgagc    19680
ccccacccgc ccatcctggc tgccctgcat gcccagaacc agctcaccga ggagcagagg    19740
tgaccaccct gtagcctgtc ccagccccac cccagctgag cctgggtcac caactggatt    19800
ccacccactc catacacacc tccagctcct cccaagaccc cctcttgagc cctgatcccc    19860
cactacaacc tgtgacccttg cagtatctcc agtcgaatca aatagactgg gcctggtggt    19920
ttactcgtgt aatcccagca cttgggaggc caaggtgggt ggatcacttg agcccaggat    19980
ttcgagacca gcctgggcaa catggcgaaa ccccatatct acaaaaaaat acaaaaatta    20040
gctgaacgtg gctgggcacg gtggctcaca cctgtaatcc cagcactttg ggaggccgag    20100
gcgggtgaat cacatgaggt aaggagtttg agaccagcct ggctaacaga gtgaaacccc    20160
gtctctacta aaaatacaaa aaaaaatta gccaggtgta gtggcaggcg cctgtagtcc    20220
cagctacttg ggaggctgag gcaggagaat ggcgtgaacc cgggaggcag agcttgcagg    20280
gagccgagat ggtgccactg cactccagcc tgggcaacag agcgagactc cgtctcaaaa    20340
```

```
aaaaaaaaaa aaaattagct gaatgtggtg ttgagtgccg ttggtcccaa ctacttggga    20400
ggctgaggtg ggaggattgc tggagcctgg gaggcagagg ttggagtgag ccaaaatcac    20460
gccactgcag ttccagtcta ggtgacagag tgagaccctg tctcaaaaaa aaaaaaaaaa    20520
aaatagtcac aattgacctc tgacctcaat ttcaacccca tctgattttc tgacctcaac    20580
tttagcattc agctggccat tcaactcaac tgtcccatct gttgacttcc ccatctttgg    20640
tcctatctga cccatgacct tattcatgac ccctcatctg actctctgac cccaaccctt    20700
gaccctcagt tctgagtaac tgactccaac ttttatgttt gactgtccag cttgactatg    20760
acaactgtgt cctttctttc tatataactg tgaccctaac cattgacccc aatggtgacc    20820
tgacccagt ctgaccctga ctttatttta tttatttatt tatttattta tttatttatt    20880
tatttattta tttttgagac agagtctggc tctgtttccc aggctggagt gcagtggagt    20940
gatctcggct cactgtagcc cccgcctccc aggttcaagc aattctactg cctcagcctc    21000
cccggtagcc gcaattacag gcgcgagcta ccacacctgg ctaattttt ttgtattttt    21060
agtagagacg gggtttcact atattggcca ggctggtttc gaactcttga cccgaagcaa    21120
tcctctcgcc tcagcctccc aaagtgctag gattacaggc gtgagccact gcacccagtc    21180
ctgaccctga ctttaatcct gacccaattt gattccttag tgccaccctg tgaatctctt    21240
tgtgacctcc tgaccagcca tcctgtccca tctctgataa gaccttgatg ctcaatgacc    21300
ctcatttacc accctgaccc tggcatgtgg ggtgccacct ctggctgctc cccctttacac   21360
cccaaaccca cctcccaact gattccaact cttatctctc catccctgt atttcctgcc    21420
cccaccacct catccacata ttgacccctc agctaccggc tctcccgggt cattgagcca    21480
ccagctgcct cctgccccag ctccccacgc atccgacggc ggatcagcct caccaagcgt    21540
ctcagtgcgt gagtctcggg gtgtgtgtag gggcggtgat gtgggcagat atcagcaagg    21600
gctgctcctg ccttagcctc atccctgtc cccatcctta ggaagcttgc ccgagagaaa    21660
agctcatcac ctagtgggag tcccggggac ccctcatccc ccacctccag gtgagcattc    21720
tgcttggtga tgggactggg gatcatggga tcaggagtca gcacagccac cccacctcag    21780
cctctgcatc tccccagtg tgtccccagg gtcaccccc tcaagtccta gaagcagaga    21840
tgctcctgct ggcagtcccc cggcctctcc agggccccag ggcccagca caaggtacc    21900
aagacggctt gtgtgtgcat gcgggcctgc gggcacccag gctctgtgtg tgtgcacgtg    21960
tgtgtgcatg cacatgtgta cacacaggat tgtggggcca ggagtgtata caggaggcac    22020
actgagcgcc cggggtatcc atccagggga ttgcatgcat ctgcacggcc ctgtttgggt    22080
gatcactcat aaatccgact cgtgctcaga tttggacctg tgtaactgct tgcccatggg    22140
tcatctaggg tgcaatcaca tcacaccct ttttatttga acagggtct tcttgctctg    22200
tcacccaggc tgaagtgcag cggtgcaatc tcagctcacc gcaacttcca ccctcccc    22260
aggctcaagc aatccttcca cctcagcctc ccaagtagct aggaccacag gtgtgcacca    22320
ccatgccctg ctatttttt tatttagtag agatgaggtt tcgccatgtt gcccaggtgg    22380
gtttcgaact cctgagctca acaatgcac tcacctcggc ctcccaaagt gctgggatta    22440
caggtgtgag ccaccgcacc cagcctacac ttttttgagg acatgtatgt ccctaagaat    22500
ctgcatacca tggcagacac ggtggctatt gcctgtgatc ccggcacttt gggaagccaa    22560
agtgggagga ttgcttgagg ccgggagttc aagaccagcc tgggcaacat agtgagaccc    22620
tatttctatt aaaagtcaaa aaattagct gggtgtagtc ccagctactc agcaggctga    22680
ggtggaagga tcgcttgagt ttgaggctgc agtgagctac gatcatgcca cggcactcta    22740
```

```
gcctgcatga tagagcgaga tcctgtttat gaagaaaaag agactgggca cggtggctca   22800
cgcctgtaat cccagcactc tgggaggccg aggtgggcgg atcacgaggt caagagatcg   22860
agaccatcct ggccaacgtg gtgaaaccct gtctctactg aaaatagaaa aattagctgg   22920
gtatggtcgc gcacacctgt agtcccagct acttgggagg ctgaggcagg agaatcactt   22980
gaacccagga gacggaggtt gcagtgagct gagatggtgc cactgcactc catccagcct   23040
ggtgacagag cgaggctccc tctaaaagaa aaacaaaaaa agaaaaggaa atgaaggaaa   23100
tgaaggctgg gcatggtagc tcatgcctgt aatcccagca cttttgggagg ccgaggccag   23160
tggatcactt gaggccagga atttgagacc agcctagcca acatggtgaa accccgtctc   23220
tactaaaaat aaaaacatta gctgggcata gtggcacagg cctgtaatcc cagctacttg   23280
ggagggtgag gcatgagaat tgcttgaacc tgggaggcag aggttgcagt gagctgagat   23340
ggcaccactg cattccagcc tgggtgacag agcaagactc tgtctcaaaa aaaaaagaaa   23400
agaaaaagaa aagaatctgt gtaccagaag aggaaatgtg ggcctgagta ttcatgagat   23460
catgtgtggg gttgttcatt ggcatgggct gtgggtgtat aaccgctgtc agcatatgta   23520
tgtacacagg atttcttgtg tatgagcatg ggttgtgtgt atatggacac tgttcatgtc   23580
tgtttctata acaggtaacc aaagtctgta tatggtaggg tggtgtatat gcaggcttgt   23640
gaatgtactc cagttgcatg tcccaggctc tgcatgtgta gggggtagta gtatgttttc   23700
ttgagatttt attttatttt attatttatt tatttatttt tgagatggag tcttgctctg   23760
tcacgcaggc tggagtgcag tagcgtgatc ttggctcact gcaacctctg cctctcaagt   23820
tcaagtgatt ctcctgcctc ggcctcccaa gtagctggga ttacaggcat gcgccaccag   23880
gccctgctaa ttttttgtatt tttagtagag acggagtttc accacgttgg ccaggctggt   23940
cttgaactcc cgacctcaag tgatccgccc acctcggcct cccaaaatgc tgagattaca   24000
ggcatgagcc actgcgccca gccaatgttt tcttgagatt ttaaatgtgg ggctattgaa   24060
tgcaccagtg gtggctgggg tgttcgtgct tttctagccc tcagcatctg cagatgggcc   24120
aagctgtagc ctccacccct tactgcctgc agctgcccct gagcctggac ctgcccagcc   24180
cccggcccct cgctttgcct ctgggcagcc ctcgaatccc cctcccggcg cagcagagct   24240
cggaggcccg tgtcatccgc gtcagcatcg acaatgacca cgggaacctg tatcgaagca   24300
tcttggtgag gggctgggct gggggtctgc tggaggctgc cctgcccttg ggccggggc   24360
cctcacctca cctcccgccc ctctcttcca gctgaccagt caggacaaag cccccagcgt   24420
ggtccggcga gccttgcaga agcacaatgt gccccagccc tgggcctgtg actatcagct   24480
ctttcaagtc cttcctgggg accggggtga gcagggatgg gttggagctc aggataggg   24540
gcagcgggga ggcgagcaga ctgaccacgc ccaaggatgg agcccaaggt tacccgggtt   24600
cacagggctg tgaggtgctt caggcagaga gtaggggtaa gataatcagt ggaggtaaga   24660
ggacataaaa tacctgtaac ccaacgatgt agggtcatga gattgtcttg gctcagtgtg   24720
agagagaggt accaaaggtc atcttcctaa aatttaaaag acaataagat tgtccagggt   24780
ccggccaggc gcagtggctc atgtctgtaa tcccagcact ttgggaggtc aagctgggcg   24840
gatcacttga ggtcaggagt ttgagaccag gctgaccaac gtggtgaaac cccgtctcta   24900
cgaaacatac aaaaattagt cgggtgtggt ggcacactcc tgtagtccca gctactcagg   24960
aggctgaggc aggagaataa ttgcttgaat ctgggaggcg gaggttgcag tgagccgaga   25020
tcataccact gcacttcagc ctgggcagca gagcgagact ctgtttaaaa aaaaaaaaaa   25080
```

```
aaaaaaagac tgtccacgga caagtgacag aagggagtgt ttctgacctt caatttgtag    25140
gatgggctgg gcatggtggc tcacaactgt aatcccagcc ctttgggagg tcaaggtggg    25200
tggattgtct gagctcagga gtttgagacc agcctgggca acatgaggag accccatcta    25260
tacaaaaaat agagaaattg gctgggtgcg gtggctcaac gcctgtaatc ccggcacttt    25320
gggaggccaa agcgggtgga tcacttgagg tcaggagttc gagaccagcc tggccaacat    25380
ggtgaagccc cgtctctact aaaaatacaa aaaattagc tgggcatggt ggcacatgcc    25440
tgtagtctca gctactcggg aggctgaggc agaagaatcg cttgaaccca ggaggcggag    25500
gttgcagtga gccgagatcg caccactgca ctccagcctg gcgactgagc aagactctgt    25560
ctcaaaaaaa aaaaaaaaaa aaaaaaaaaa aaaagccaat atatatatat atatatagag    25620
agagagagag agagagagag agagagagag agattagctg agcatggtgg catgtgcctg    25680
tattcccaac tccaactact ggggaggctg aggtgggagg atcacttgag cctaggaggt    25740
ggaggctgca gcgagctgag atcacgccac tgcactccag cctgggtgac agagcaagac    25800
cctgtctcaa ttaaaaaaaa aaagggggc cgggcatggt ggctcacgcc tgtaatccca    25860
gcactttggg aggccgaggc gggtggatca cgaagtcaag agatcgagac catcctggcc    25920
aacatggtga agcctcgtct ctactaaaaa tacaaaaaat agccaggca tggtggcagg    25980 cgcctatagt cccagctact caggaggctg aggcagaaga atcacttgaa cccaggaggt    26040
gaaggttgca gtgagccaag attgcgccac tgcactccag cctggcgaca gagtgagact    26100
ccgtctcaaa aaaaagaaa aaatagattg tctagggtcg agtgagagaa gggagtgtag    26160
aagtttgtct gatcttaagt ttgtagcatc atgagattgt tcaggctcaa cctgatggga    26220
tgggagacta aagggcatct gggcttagat ttgtgagaac taagtttgtt caccactggg    26280
accctgaagt tatctgaact tgggacggga gagaggcaaa tggatagccg cggaagcatg    26340
agattgtcct gtctgacagg gagaagcaag ggattgagcg tattcacgct gaagtacatg    26400
gcatgaggtt ggctggatat taggaaagga tgcttgtggt tgttcaggtg ttgagtgtga    26460
ggccacaagc tcgtgcaggc tggaagtggg aagttattca agttcatggt gacagcagca    26520
tgggattggc tgggagtggt tgtggggag gggtagggtg agcaggaagt tgtttggcgg    26580
ggggtggtct agggtggtct aagtttgccc aaacttttac tgcaggttgt cggttttgtt    26640 tgttttttgtt tttttttttt tgagatggag tctcgtgctg ttgcccaggc tggagtgcaa    26700
tggcaggatc tcggctcacc gcaacatcca cctcctgggt tcaagagatt ctcctgcctc    26760
agccttccga gtagctggga ttacaggcat gtgccaccat gcctagctca ttttttttggt    26820 attttttagta aagacggggt ttcaccatgt tggccagact ggtctcgaat tcctgacctc    26880
aagtgatcca cccacttcgg cctcccaaag cgctgggatt acaggcacga gcatcgcgc    26940 ccggccagtt tgctcaaact tttactgcag gttgccttgt ctctatggtg aggggagaa    27000 tattaggagg ttgcccaggc ttatgataag ggaaggcatg aggtggtgca agttttcaag    27060
tgagaagtcg tccaggttcc cagtgacagc agaatgagct tggcttggca gtagctgcag    27120
agggacccat ggctgttcag gttcgcgggt gagtggcagg aggctcccgg gtcctctgtg    27180
ggggtgacac aaggttgtga gggcctatta ccaccatctc cactcctgac cagtgctcct    27240
gattcctgac aatgccaacg tcttctatgc catgagtcca gtcgccccca gagacttcat    27300
gctgcggcgg aaagagggga cccggaacac tctgtctgtc tccccaagct gaggcagccc    27360
tgtcctctcc acaagacaca agtcccacag gcaagcttgc gactcttctc ctggaaagct    27420
gccatccccc agtagaggcc actgtgctgt gtatcccagg accaccaccc aactgtagcc    27480
```

-continued

```
cattggaccc catctctttt tctgactctg ttggtactag atccatattc caaagacatc    27540
agcccatggg tggctggtgg agagctcaat cccataaatg tagaaagagg tggggcatgg    27600
atacgtcaaa tccctcccca gagaaatctt ataaatgtta gagacgcatc agaagtgaca    27660
gatgcggatg aaaatagtga ccagagttat gaaacaggtg tcagtcttgt ttattttgcg    27720
cctgtgtgcc atgttcaccc tttatcaaga taaaggaaaa cagctaccac acacacaccc    27780
acacacacac acacaaacac acagagagag agaaacctaa gagccaagac cagcccgggc    27840
aacataacga gatcctgtct ctacaaaaaa tacaaaaatt tggctgggcg tggtgactca    27900
cgcctgtaat cccagcgttt tgggaggcca aggcaggcag atcgcctgag gtcaggagtt    27960
cgagaccagc ctggccgaca tggcaaaacc ccatcttcta aaagtacaaa aaattagccg    28020
ggcgtggtgt catgcacctg taatcccagc tactgggag gctgaggcag gagaattgct    28080
tgaacccgga aggtggaggt tgcagtgagt ggaaatcaca ccactgtact ccagcctggg    28140
tgacagagca agaccctatc tcaaaaacaa acaaacaaac aaatgaacaa acaaaaaatt    28200
ttctgagtgt ggtgatatga gactgtaatc ctacctactt gggaggctga gctgggagaa    28260
tcaccagagc cctgggaggt tgaagctgca gtgagcagtg actgggcccc tgcactccaa    28320
cctggaggac agagggagat cctgtctcaa aaacaaaaaa actaagagcc ctaagaaagg    28380
tgttgagtcg ggtatgacac tcaacccaga tgccagagag gatcctgtct ggccggacac    28440
agtggctcag gagggtaatc ccagtacttt gggaggctga ggtaagagga ttgcttaagt    28500
tcaggagtcc gagagcagcc tgggcaatac agtgagatca catctcacta aataaataaa    28560
taaaggatcc tatcacacaa agagggttta ggacttcctt ccccaacatt tttggggtga    28620
tatgcctctt ttctactgta tatatgggag agtgactaac tgaaattcca tcagaattag    28680
aaacaaatag catcattacc catgagtcaa taagggctgt gaggatgggc cctttcactt    28740
gccctcacct tcttcctctt cctgtcacag ataacccatc tgtgcaaaga agagaaaaag    28800
aggttgggtg tggtggctca catctgtaat cccagcactt tgggaggcta aggtggaagg    28860
attttgagcc caggagtttg agaccagcct gggcaacata gtgagacccc atttctacaa    28920
aaaaatacaa agattggcca ggcgcggtgg ctcacgcctg taatcccagc acttgggagg    28980
ctgaggcagg cggatcatga ggtcaggaga tcgagaccat cctggctagg tgaaacccccg    29040 tctctactaa aaatgcaaaa aaattagccg ggcgtggtgg cgggcgcctg tagtcccagc    29100
tactcgggag gctgaggcag gagaatggcg tgaacccagg aggcggagct tgcagcgagc    29160
cgagatcgca ccactgcact ccagtctggg cgacagaggg agactccatc tcaaaaaata    29220
aaataaaatt tagccaggtt tggtgtcctg cacctgtagt ctcagctact ctggaggctg    29280
aagcacgagg atcacttgag cccaagaggt ggaggttgca gtgagccgag attactgcac    29340
tccagcctgg gtgacagagc gagatcctgt ttcaaaaagc aaaaaaaagg gccaggcgca    29400
gtgctcacac ctgtaatccc atcattttgg gaggctgagg tgggcggatc acttgaggtc    29460
aggagttcaa ggtcagcctg gccaacatgg taaaaccctg tccctactaa aaatataaaa    29520
aattagctgg gcatggtggt gggtgcctgt aatcccagtt actcaggagg ctgaggcagg    29580
agaattgctt gaatccagaa ggtggaggtt gcagtgaacc gagatcatgc cattgcactc    29640
cagcctgcgt gacaaagtga gactgtatct caaaaaaaaa aaaaaaatg ctgggcacag    29700 tggctctagc actttgggg ggcaagacgg gtggattgct tgaggccagg attccaaaac    29760
cagcctggcc aacatggtga aacccccttct ctactaaata tacaaaaaat tagccgggca    29820
```

```
tggtggcagg ctcttgtaat cccagctact cggtaggctg aggcaggata atcacctgaa    29880
ccaggcaggc agaggttgca gtgagtcgag atcgctccac tgcactccgg cctgggcaac    29940
aagagcaaaa ttctgtctgg aaaaaaaaaa aaaagaaaaa gaaaaggatt gtgaggatga    30000
aaagagaggc gtgagctctc tgtcagcgtt ggagtacaat agagaggatg aaatgagctg    30060
tagggcgaac tgctacatag tcacaaccac aataatatgc ccacttatga gctcctactc    30120
agcagagaac atcagctatg gtctttacat ctcattgcac taatcgagtt ctttctgttg    30180
caagcgacca aaaacccaat tcaaagaggc atgtgcaaaa aaggacattt gtggcttatg    30240
cagttgaaat gtccaatgag tagggcttca ggcacagttg catccaggca ctcataagat    30300
gtcatcaggg ttttcttgct gtctctttgc tctgatttgc tctgagaatg                30350
```

<210> SEQ ID NO 4
<211> LENGTH: 709
<212> TYPE: PRT
<213> ORGANISM: Mus musculus

<400> SEQUENCE: 4

```
Met Glu Arg Thr Ala Gly Lys Glu Leu Ala Leu Ala Pro Leu Gln Asp
 1               5                  10                  15

Trp Gly Glu Thr Glu Asp Gly Ala Val Tyr Ser Val Ser Leu Arg
                20                  25                  30

Arg Gln Arg Ser Gln Arg Ser Thr Pro Glu Arg Ser Gly Glu Gly Gln
             35                  40                  45

Thr Pro Ile Pro Ala Thr Asp Thr Phe Leu His Tyr Arg Thr Ser Lys
 50                  55                  60

Val Arg Ala Leu Arg Ala Ala Arg Leu Glu Arg Leu Val His Glu Leu
 65                  70                  75                  80

Val Ser Gly Asp Arg Glu Gln Asp Pro Gly Phe Val Pro Ala Phe Leu
                 85                  90                  95

Ala Thr His Arg Ala Phe Val Pro Thr Ala Arg Val Leu Gly Phe Leu
            100                 105                 110

Leu Pro Pro Pro Pro Pro Pro Pro Pro Ala Gly Val Asp Ser
        115                 120                 125

Lys Arg Thr Glu Gly Gln Asp Leu Asn Phe Ser Lys Asn Leu Arg Ala
130                 135                 140

Val Val Ser Val Leu Gly Ser Trp Leu Arg Asn His Pro Gln Asp Phe
145                 150                 155                 160

Arg Asp Pro Pro Asp His Gln Asn Leu Gly Asn Val Arg Ile Phe Leu
                165                 170                 175

Gly Trp Val Ala Pro Gly Gly Ala Glu Ala Arg Glu Ala Glu Lys Leu
            180                 185                 190

Leu Glu Asp Phe Leu Lys Glu Ala Lys Gly Glu Gln Thr Glu Glu Glu
        195                 200                 205

Lys Arg Leu Ala Trp Ser Gly Pro Pro Arg Ile Ala Gln Thr Pro Gly
    210                 215                 220

Ser Glu Phe Ala Glu Asp Cys Val Glu Glu Gly Pro Ser Ser Glu
225                 230                 235                 240

Gly Pro Glu Leu Leu Asp Phe Ser Val Asp Val Ala Glu Gln Leu
                245                 250                 255

Thr Leu Met Asp Val Glu Leu Phe Leu Arg Val Arg Ser Cys Glu Cys
            260                 265                 270

Leu Gly Ser Met Trp Ser Gln Arg Asp Arg Pro Gly Ala Ala Gly Ile
        275                 280                 285
```

```
Ser Pro Thr Val Arg Ala Thr Val Ala Gln Phe Asn Thr Val Thr Gly
    290                 295                 300
Cys Val Leu Gly Ser Val Leu Ala Ala Pro Gly Leu Ala Ala Ser Gln
305                 310                 315                 320
Arg Ala Gln Arg Ile Glu Lys Trp Ile Arg Ile Ala Gln Arg Cys Arg
                325                 330                 335
Glu Leu Arg Asn Phe Ser Ser Leu Arg Ala Ile Leu Ser Ala Leu Gln
            340                 345                 350
Ser Asn Pro Ile Tyr Arg Leu Lys Arg Ser Trp Gly Ala Val Ser Arg
        355                 360                 365
Glu Pro Leu Ser Val Phe Arg Lys Leu Ser Gln Ile Phe Ser Asp Glu
    370                 375                 380
Asp Asn His Leu Ser Ser Arg Ala Ile Leu Ser Gln Glu Glu Thr Thr
385                 390                 395                 400
Glu Asp Asp Asp Cys Pro Ser Gly Ser Leu Pro Ser Lys Leu Pro Pro
                405                 410                 415
Gly Pro Val Pro Tyr Leu Gly Thr Phe Leu Thr Asp Leu Val Met Leu
            420                 425                 430
Asp Thr Ala Leu Pro Asp Thr Leu Lys Gly Asn Leu Ile Asn Phe Glu
        435                 440                 445
Lys Arg Arg Lys Glu Trp Glu Ile Leu Ala Arg Ile Gln Gln Leu Gln
    450                 455                 460
Gln Arg Cys Gln Arg Tyr Ser Leu Ser Pro Arg Pro Ile Leu Ala
465                 470                 475                 480
Ala Leu Arg Ala Gln Arg Gln Leu Ser Glu Glu Gln Ser Tyr Arg Val
                485                 490                 495
Ser Arg Val Ile Glu Pro Ala Ala Ser Cys Pro Ser Ser Pro Arg
            500                 505                 510
Ile Arg Arg Arg Ile Ser Leu Thr Lys Arg Leu Ser Ala Lys Leu Ser
        515                 520                 525
Arg Glu Lys Asn Ser Ser Pro Gly Gly Ser Pro Gly Asp Pro Ser Ser
    530                 535                 540
Pro Thr Ser Ser Val Ser Pro Gly Ser Pro Pro Ser Ser Pro Arg Asn
545                 550                 555                 560
Arg Glu Pro Pro Pro Gly Ser Pro Ala Ser Pro Gly Pro Gln
                565                 570                 575
Ser Pro Ser Thr Lys Leu Ser Leu Thr Met Asp Pro Pro Gly Pro Trp
            580                 585                 590
Pro Val Thr Leu Thr Pro Ser Ser Arg Val Pro Leu Leu Gly Gln
        595                 600                 605
Gln Thr Ser Glu Ala Arg Val Ile Arg Val Ser Ile Asn Asn Asn His
    610                 615                 620
Gly Asn Leu Tyr Arg Ser Ile Leu Leu Thr Cys Gln Asp Lys Ala Pro
625                 630                 635                 640
Ser Val Val Gln Arg Ala Leu Glu Lys His Asn Val Pro Gln Pro Trp
                645                 650                 655
Ala Arg Asp Tyr Gln Leu Phe Gln Val Leu Pro Gly Asp Arg Glu Leu
            660                 665                 670
Leu Ile Pro Asp Gly Ala Asn Val Phe Tyr Ala Met Ser Pro Ala Ala
        675                 680                 685
Pro Gly Asp Phe Leu Leu Arg Arg Lys Glu Gly Thr Gly His Thr Leu
    690                 695                 700
```

-continued

Ser Ala Ser Pro Thr
705

<210> SEQ ID NO 5
<211> LENGTH: 725
<212> TYPE: PRT
<213> ORGANISM: Homo sapiens

<400> SEQUENCE: 5

```
Met Ser Ser Ile Gln Asp Trp Gly Glu Val Glu Glu Gly Ala Val
 1               5                  10                  15

Tyr His Val Thr Leu Lys Arg Val Gln Ile Gln Gln Ala Ala Asn Lys
                20                  25                  30

Gly Ala Arg Trp Leu Gly Val Glu Gly Asp Gln Leu Pro Pro Gly His
            35                  40                  45

Thr Val Ser Gln Tyr Glu Thr Cys Lys Ile Arg Thr Ile Lys Ala Gly
        50                  55                  60

Thr Leu Glu Lys Leu Val Glu Asn Leu Leu Thr Ala Phe Gly Asp Asn
65                  70                  75                  80

Asp Phe Thr Tyr Ile Ser Ile Phe Leu Ser Thr Tyr Arg Gly Phe Ala
                85                  90                  95

Ser Thr Lys Glu Val Leu Glu Leu Leu Leu Asp Arg Tyr Gly Asn Leu
                100                 105                 110

Thr Ser Pro Asn Cys Glu Glu Asp Gly Ser Gln Ser Ser Ser Glu Ser
            115                 120                 125

Lys Met Val Ile Arg Asn Ala Ile Ala Ser Ile Leu Arg Ala Trp Leu
            130                 135                 140

Asp Gln Cys Ala Glu Asp Phe Arg Glu Pro Pro His Phe Pro Cys Leu
145                 150                 155                 160

Gln Lys Leu Leu Asp Tyr Leu Thr Arg Met Met Pro Gly Ser Asp Pro
                165                 170                 175

Glu Arg Arg Ala Gln Asn Leu Leu Glu Gln Phe Gln Lys Gln Glu Val
            180                 185                 190

Glu Thr Asp Asn Gly Leu Pro Asn Thr Ile Ser Phe Ser Leu Glu Glu
            195                 200                 205

Glu Glu Glu Leu Glu Gly Gly Glu Ser Ala Glu Phe Thr Cys Phe Ser
        210                 215                 220

Glu Asp Leu Val Ala Glu Gln Leu Thr Tyr Met Asp Ala Gln Leu Phe
225                 230                 235                 240

Lys Lys Val Val Pro His His Cys Leu Gly Cys Ile Trp Ser Arg Arg
                245                 250                 255

Asp Lys Lys Glu Asn Lys His Leu Ala Pro Thr Ile Arg Ala Thr Ile
            260                 265                 270

Ser Gln Phe Asn Thr Leu Thr Lys Cys Val Val Ser Thr Ile Leu Gly
            275                 280                 285

Gly Lys Glu Leu Lys Thr Gln Gln Arg Ala Lys Ile Ile Glu Lys Trp
        290                 295                 300

Ile Asn Ile Ala His Glu Cys Arg Leu Leu Lys Asn Phe Ser Ser Leu
305                 310                 315                 320

Arg Ala Ile Val Ser Ala Leu Gln Ser Asn Ser Ile Tyr Arg Leu Lys
                325                 330                 335

Lys Thr Trp Ala Ala Val Pro Arg Asp Arg Met Leu Met Phe Glu Glu
            340                 345                 350

Leu Ser Asp Ile Phe Ser Asp His Asn Asn His Leu Thr Ser Arg Glu
            355                 360                 365
```

```
Leu Leu Met Lys Glu Gly Thr Ser Lys Phe Ala Asn Leu Asp Ser Ser
        370             375             380

Val Lys Glu Asn Gln Lys Arg Thr Gln Arg Arg Leu Gln Leu Gln Lys
385             390             395                         400

Asp Met Gly Val Met Gln Gly Thr Val Pro Tyr Leu Gly Thr Phe Leu
                405             410                 415

Thr Asp Leu Thr Met Leu Asp Thr Ala Leu Gln Asp Tyr Ile Glu Gly
            420             425             430

Gly Leu Ile Asn Phe Glu Lys Arg Arg Arg Glu Phe Glu Val Ile Ala
            435             440             445

Gln Ile Lys Leu Leu Gln Ser Ala Cys Asn Ser Tyr Cys Met Thr Pro
450             455             460

Asp Gln Lys Phe Ile Gln Trp Phe Gln Arg Gln Gln Leu Leu Thr Glu
465             470             475                         480

Glu Glu Ser Tyr Ala Leu Ser Cys Glu Ile Glu Ala Ala Ala Asp Ala
            485             490             495

Ser Thr Thr Ser Pro Lys Pro Arg Lys Ser Met Val Lys Arg Leu Ser
            500             505             510

Leu Leu Phe Leu Gly Ser Asp Met Ile Thr Ser Pro Thr Pro Thr Lys
            515             520             525

Glu Gln Pro Lys Ser Thr Ala Ser Gly Ser Ser Gly Glu Ser Met Asp
            530             535             540

Ser Val Ser Val Ser Ser Cys Glu Ser Asn His Ser Glu Ala Glu Glu
545             550             555                         560

Gly Ser Ile Thr Pro Met Asp Thr Pro Asp Glu Pro Gln Lys Lys Leu
                565             570             575

Ser Glu Ser Ser Ser Cys Ser Ser Ile His Ser Met Asp Thr Asn
            580             585             590

Ser Ser Gly Met Ser Ser Leu Ile Asn Pro Leu Ser Ser Pro Pro Ser
            595             600             605

Cys Asn Asn Asn Pro Lys Ile His Lys Arg Ser Val Ser Val Thr Ser
610             615             620

Ile Thr Ser Thr Val Leu Pro Pro Val Tyr Asn Gln Gln Asn Glu Asp
625             630             635                         640

Thr Cys Ile Ile Arg Ile Ser Val Glu Asp Asn Gly Asn Met Tyr
                645             650             655

Lys Ser Ile Met Leu Thr Ser Gln Asp Lys Thr Pro Ala Val Ile Gln
            660             665             670

Arg Ala Met Leu Lys His Asn Leu Asp Ser Asp Pro Ala Glu Glu Tyr
            675             680             685

Glu Leu Val Gln Val Ile Ser Glu Asp Lys Glu Leu Val Ile Pro Asp
            690             695             700

Ser Ala Asn Val Phe Tyr Ala Met Asn Ser Gln Val Asn Phe Asp Phe
705             710             715             720

Ile Leu Arg Lys Lys
                725
```